US012559517B2

(12) United States Patent
Yamashita et al.

(10) Patent No.: US 12,559,517 B2
(45) Date of Patent: Feb. 24, 2026

(54) OLIGONUCLEOTIDE MANUFACTURING METHOD

(71) Applicant: AJINOMOTO CO., INC., Tokyo (JP)

(72) Inventors: Ken Yamashita, Kawasaki (JP); Kunihiro Hirai, Kawasaki (JP); Satoshi Katayama, Kawasaki (JP); Taisuke Ichimaru, Kawasaki (JP); Daisuke Takahashi, Kawasaki (JP); Naoko Hirose, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 901 days.

(21) Appl. No.: 17/654,700

(22) Filed: Mar. 14, 2022

(65) Prior Publication Data

US 2022/0235090 A1 Jul. 28, 2022

Related U.S. Application Data

(63) Continuation of application No. 16/014,536, filed on Jun. 21, 2018, now abandoned, which is a continuation of application No. PCT/JP2016/088580, filed on Dec. 22, 2016.

(30) Foreign Application Priority Data

Dec. 22, 2015 (JP) ................................ 2015-250665

(51) Int. Cl.
*C07H 21/04* (2006.01)

(52) U.S. Cl.
CPC .............. *C07H 21/04* (2013.01); *Y02P 20/55* (2015.11)

(58) Field of Classification Search
CPC ................................ C07H 21/04; Y02P 20/55
USPC ...................................................... 536/25.31
See application file for complete search history.

(56) References Cited

U.S. PATENT DOCUMENTS

| | | | |
|---|---|---|---|
| 4,415,732 | A | 11/1983 | Caruthers et al. |
| 5,571,902 | A | 11/1996 | Ravikumar et al. |
| 5,734,041 | A | 3/1998 | Just et al. |
| 5,792,615 | A | 8/1998 | Arnold, Jr. et al. |
| 5,837,856 | A | 11/1998 | Arnold, Jr. et al. |
| 5,945,521 | A | 8/1999 | Just et al. |
| 5,955,597 | A | 9/1999 | Arnold, Jr. et al. |
| 5,986,083 | A | 11/1999 | Dwyer et al. |
| 6,028,188 | A | 2/2000 | Arnold, Jr. et al. |
| 6,031,092 | A | 2/2000 | Just et al. |
| 6,060,456 | A | 5/2000 | Arnold, Jr. et al. |
| 6,090,937 | A | 7/2000 | Takamatsu et al. |
| 6,160,109 | A | 12/2000 | Just et al. |
| 6,211,354 | B1 | 4/2001 | Horie et al. |
| 6,262,036 | B1 | 7/2001 | Arnold, Jr. et al. |
| 6,340,749 | B1 | 1/2002 | Zhang et al. |
| 6,476,216 | B1 | 11/2002 | Just et al. |
| 6,500,946 | B1 | 12/2002 | Takamatsu et al. |
| 6,596,857 | B1 | 7/2003 | Just et al. |
| 7,217,805 | B2 | 5/2007 | Imanishi et al. |
| 7,994,145 | B2 | 8/2011 | Imanishi et al. |
| 8,586,728 | B2 | 11/2013 | Sproat |
| 8,691,970 | B2 | 4/2014 | Ohgi et al. |
| 8,846,885 | B2 | 9/2014 | Hirai et al. |
| 9,029,528 | B2 | 5/2015 | Hirai et al. |
| 9,284,344 | B2 | 3/2016 | Kim et al. |
| 9,371,353 | B2 | 6/2016 | Hirai et al. |
| 9,914,746 | B2 | 3/2018 | Sproat |
| 10,464,966 | B2 | 11/2019 | Hirai et al. |
| 2003/0114660 | A1 | 6/2003 | Just et al. |
| 2003/0229219 | A1 | 12/2003 | Just et al. |

(Continued)

FOREIGN PATENT DOCUMENTS

| | | | |
|---|---|---|---|
| EP | 2 816 053 | A1 | 12/2014 |
| JP | 9-505306 | A | 5/1997 |

(Continued)

OTHER PUBLICATIONS

Lavergne et al. Optimized Fluoride Ions Treatment for Release of Base-Sensitive 2'-O-Modified Oligoribonucleotides from Various Solid Supports. Nucleic Acids Symposium Series No. 52 321-322, 2008. (Year: 2008).*

Theodora W. Greene, et al., "Silyl Ethers", Protective Groups in Organic Synthesis, 1998, pp. 77-86 and cover page.

Kevin J. Fettes, et al., "Synthesis and nucleic acid-binding properties of sulfamide—and 3'-W-sulfamate-modified DNA", Journal of the Chemical Society, Perkin Transactions 1, vol. 4, 2002, pp. 485-495.

Sholaku Kim, et al., "Liquid-Phase RNA Synthesis by Using Alkyl-Chain-Soluble Support", Chemistry—A European Journal, vol. 19, No. 26, 2013, pp. 8615-8620.

Takao Shoji, et al., "Synthesis of Conjugated Oligonucleotide in Solution Phase Using Alkyl-chain-soluble Support", Chemistry Letters, vol. 43, No. 8. 2014, pp. 1251-1253.

(Continued)

*Primary Examiner* — Yih-Horng Shiao
(74) *Attorney, Agent, or Firm* — Oblon, McClelland, Maier & Neustadt, L.L.P.

(57) ABSTRACT

The present invention aims to provide a more stable and efficient method for producing oligonucleotide, particularly, oligonucleotide having various functional groups linked to the 3'-terminal and the like. Efficient production of oligonucleotide becomes possible by a production method of an oligonucleotide represented by the formula (Ia-2) (each symbol is as defined in the DESCRIPTION) and having a functional group at 3'-terminal, the method including a step of subjecting an oligonucleic acid with 3'-terminal protected by a silyl-protecting group to 3'-terminal-selective deprotection under desilylation conditions that do not affect protecting groups other than the silyl group, subjecting same to phosphitylation conditions with a phosphoramidite reagent that do not affect protecting groups on the oligonucleic acid to give a 3'-terminal-phosphoramidited oligonucleotide represented by the formula (Ia-1) (each symbol is as defined in the DESCRIPTION), and linking a functional group to 3'-terminal of 3'-terminal phosphoramidited oligonucleotide directly or via a linker, and the like.

8 Claims, No Drawings

Specification includes a Sequence Listing.

(56) References Cited

U.S. PATENT DOCUMENTS

| | | | |
|---|---|---|---|
| 2004/0143114 A1 | 7/2004 | Imanishi et al. | |
| 2007/0249049 A1 | 10/2007 | Swayze et al. | |
| 2008/0206851 A1* | 8/2008 | Dellinger | C07H 21/02 536/25.31 |
| 2009/0005550 A1 | 1/2009 | Heindl et al. | |
| 2009/0012279 A1 | 1/2009 | Heindl | |
| 2011/0269821 A1 | 11/2011 | Swayze et al. | |
| 2011/0294124 A1 | 12/2011 | Wada et al. | |
| 2011/0313019 A1 | 12/2011 | Swayze et al. | |
| 2012/0059045 A1 | 3/2012 | Prakash et al. | |
| 2012/0142101 A1 | 6/2012 | Manoharan et al. | |
| 2012/0296074 A1 | 11/2012 | Hirai et al. | |
| 2013/0131147 A1 | 5/2013 | Seth et al. | |
| 2013/0267697 A1 | 10/2013 | Hirai et al. | |
| 2014/0107330 A1 | 4/2014 | Freier et al. | |
| 2014/0258926 A1 | 9/2014 | Damha et al. | |
| 2014/0303235 A1 | 10/2014 | Oestergaard et al. | |
| 2014/0309279 A1 | 10/2014 | Oestergaard et al. | |
| 2014/0323707 A1 | 10/2014 | Seth et al. | |
| 2015/0051389 A1 | 2/2015 | Seth et al. | |
| 2015/0112053 A1 | 4/2015 | Kim et al. | |
| 2015/0126725 A1 | 5/2015 | Swayze et al. | |
| 2015/0167006 A1 | 6/2015 | Swayze et al. | |
| 2015/0315229 A1 | 11/2015 | Nonogawa | |
| 2017/0044526 A1 | 2/2017 | Wan et al. | |
| 2017/0320904 A1 | 11/2017 | Hirai et al. | |

FOREIGN PATENT DOCUMENTS

| | | | |
|---|---|---|---|
| JP | 9-505307 A | 5/1997 |
| JP | 11-322783 A | 11/1999 |
| JP | 2001-89496 A | 4/2001 |
| JP | 2002-255990 A | 9/2002 |
| JP | 2008-163024 A | 7/2008 |
| JP | 2009-516521 A | 4/2009 |
| JP | 2009-524695 A | 7/2009 |
| JP | 2010-275254 A | 12/2010 |
| JP | 2012-506701 A | 3/2012 |
| JP | 2012-510460 A | 5/2012 |
| JP | 2012-111728 A | 6/2012 |
| WO | WO 00/00499 A1 | 1/2000 |
| WO | WO 2005/070859 A1 | 8/2005 |
| WO | WO 2011/005861 A1 | 1/2011 |
| WO | WO 2011/061114 A1 | 5/2011 |
| WO | WO 2011/156202 A1 | 12/2011 |
| WO | WO 2012/024776 A1 | 3/2012 |
| WO | WO 2012/157723 A1 | 11/2012 |
| WO | WO 2013/022966 A1 | 2/2013 |
| WO | WO 2013/122236 A1 | 8/2013 |
| WO | WO 2013/179412 A1 | 12/2013 |
| WO | WO 2014/077292 A1 | 5/2014 |
| WO | WO 2015/168172 A1 | 11/2015 |
| WO | WO 2016/117863 A1 | 7/2016 |
| WO | WO 2017/086397 A1 | 5/2017 |
| WO | WO 2017/104836 A1 | 6/2017 |

OTHER PUBLICATIONS

Chih-Hau Chen, et al., "Convergent Solution Phase Synthesis of Chimeric Oligonucleotides by a 2+2 and 3+3 Phosphoramidite Strategy", Aust, J. Chem., vol. 63, 2010, pp. 227-235.

Matthaus Janczyk, et al., "A new and convenient approach for the preparation of β-cyanoethyl protected trinucleotide phosphoramidites", Organic & Biomolecular Chemistry, vol. 10, 2012, 40 pages.

V.A.Efimove, et al., "Rapid synthesis of long-chain deoxyribooligonucleotides by the N-methylimidazolide phosphotriester method", Nucleic Acids Research, vol. 11, No. 23, 1983, pp. 8369-8387.

Ravi Gukathasan, et al., "Large-scale synthesis of high purity "Phos reagent" useful for oligonucleotide therapeutics", Journal of Organometallic Chemistry, vol. 690, 2005, pp. 2603-2607.

Yogesh S. Sanghvi, et al., :Improved and Process for the Preparation of Nucleosidic Phosphoramidites Using a Safer and Cheaper Activator, Organic Process Research & Development, vol. 4, 2000, pp. 175-181.

Akihiro Ohkubo, et al., "Efficient synthesis of functionalized oligodeoxyribonucleotides with base-labile groups using a new silyl linker", Bioorganic & Medicinal Chemistry, vol. 18, 2008, pp. 5345-5351.

Chooyu Xie, et al., "Nucleosidic Phosphoramidite Synthesis via Phosphitylation: Activator Selection and Process Development", Organic Process Research & Development, vol. 9, 2005, pp. 730-737.

Didier Gasparutto, et al., "Chemical synthesis of a biologically active natural tRNA with its minor bases", Nucleic Acids Research, vol. 20, No. 19, 1992, pp. 5159-5166.

* cited by examiner

OLIGONUCLEOTIDE MANUFACTURING METHOD

CROSS REFERENCE TO RELATED APPLICATIONS

This application is a continuation of U.S. application Ser. No. 16/014,536, filed on Jun. 21, 2018, which is a continuation of international patent application PCT/JP2016/088580, filed on Dec. 22, 2016, the text of which is incorporated by reference, and claims foreign priority to Japanese Patent Application No. 2015-250665, filed on Dec. 22, 2015, the entire contents of which are incorporated herein by reference.

TECHNICAL FIELD

The present invention relates to a production method of an oligonucleotide. More particularly, the present invention relates to a method for producing an oligonucleotide by utilizing a silyl-protecting group, a method for producing an oligonucleotide by utilizing a phosphitylating agent, and a method for producing an oligonucleotide by fragment condensation and the like.

BACKGROUND ART

The synthesis method of oligonucleotide includes a phosphate triester method, an H-phosphonate method, a phosphoramidite method and the like, and solid phase synthesis (solid phase method) using a phosphoramidite method is most widely used at present (non-patent document 1). Oligonucleotides consisting of several nucleotides can be synthesized by sequentially linking nucleotides to be the starting material. When synthesizing oligonucleotides of about 20 mer or more, a blockmer synthesis method including preparing a building block group of 2 to 3 nucleotides in advance and repeating linkage thereof to obtain a product with a desired chain length, a unit coupling (fragment condensation) synthesis method including linking oligonucleotides of about 10 bases or more to give an oligonucleotide and the like are utilized. The fragment condensation method requires special care for ensuring solubility, selective deprotection and activation of the reaction sites and the like.

In the Examples of patent document 2 and in non-patent document 2, oligomers in which the phosphate of the internucleotide is protected by a cyanoethyl group is obtained by adopting levulinyl ester as a protecting group capable of selective deprotection of the 3'-hydroxyl group of an oligonucleic acid fragment, and performing elongation by a phosphoramidite method. The deprotection requires use of hydrazine having safety problems. In addition, non-patent document 2 describes that falling off of the base protecting group may proceed under deprotection conditions.

Non-patent document 3 describes a blockmer synthesis method for synthesizing oligonucleic acid by using 3-mer amidite. However, cleavage of phosphate and elimination of cyanoethyl as a protecting group pose problems in the reaction process. While a protective group, which is difficult to be eliminated, is used in patent document 1, the protecting group is special and cannot be utilized directly to conventional reaction conditions and the like.

While non-patent document 4 describes a method of synthesizing oligonucleotides by fragment condensation using a triester method, the triester method is hardly used practically at present.

On the other hand, a method for synthesizing a longer-chain oligonucleotide by using a 3'-terminal phosphoramidited oligonucleotide prepared using a phosphitylating agent is known. For phosphitylation of nucleosides, 2-cyanoethyl-N,N-diisopropylchlorophosphoramidite has conventionally been used. In patent document 2, it is combined with N-methylimidazole to perform phosphitylation of the deprotected 3'-terminal of oligonucleic acid. However, 2-cyanoethyl-N,N-diisopropylchlorophosphoramidite is inferior in preservation stability and the market value is high.

2-Cyanoethyl-N,N,N',N'-tetraisopropylphosphordiamidite is used as an economical and stable substitute for the aforementioned reagents (non-patent document 5). The reactivity of the agent itself is poor, and an activator is required for the phosphitylation of nucleoside. Diisopropylammonium tetrazolide is used as a conventional method in the phosphitylation of nucleoside monomers not having a fragile protecting group. However, it is known that a cyanoethyl group vulnerable to base, which is on the phosphoric acid moiety of internucleotide, markedly falls off when the aforementioned ammonium salt is used for phosphitylation of the 3'-hydroxyl group of an oligonucleic acid fragment by cyanoethyl-N,N,N',N'-tetraisopropylphosphordiamidite (non-patent document 3). In addition, it has been reported that a strong acid such as trifluoromethanesulfonic acid and base salt is used as an activator, phosphite and pentavalent phosphorus compound are by-produced due to excessive activity (non-patent document 6 and 7). During the synthesis process of oligonucleotide, a silyl-protecting group is used as a protecting group of the 2'-position hydroxyl group. For its deprotection, namely, desilylation, a salt of hydrogen fluoride:triethylamine=3:1 (3HF-TEA) is generally used (non-patent document 8). 3HF-TEA is an acidic salt, 4,4'-dimethoxytriethylamine, which is commonly used as a 5'-terminal protecting group in oligonucleic acid synthesis, is promoted in elimination under acidic condition. To prevent unpreferable falling off of the dimethoxytrityl group, a salt with an acid:amine=1:1 molar ratio, which is 3HF-TEA further added with triethylamine, is used for cleavage of 3'-terminal silyl-protecting group (up to linker) in non-patent document 9. In addition, when triethylamine is used for desilylation of the 3'-terminal of oligonucleic acid having a cyanoethyl-protected phosphoric acid moiety, problems such as falling off of the cyanoethyl protecting group can be mentioned occur.

DOCUMENT LIST

Patent Documents patent document 1: U.S. Pat. No. 5,571,902 patent document 2: WO 2014/077292

Non-Patent Documents non-patent document 1: S. L. Beaucage et al., Current Protocols in Nucleic Acid Chemistry; John Wiley & Sons (2000)

non-patent document 2: Chen, C.-H. et al., Aust. J. Chem. 2010, 63, 227-235 non-patent document 3: Muller, S. et al., Org. Biomol. Chem. 2012, 10, 1510-1513 non-patent document 4: Chekhmakhcheva, O. G. et al., A Nucleic Acid Res. 1983, 11, 8369-8387 non-patent document 5: Gukathasan, R. et al., J. Organomet. Chem. 2005, 690, 2603-2607 non-patent document 6: Yogesh S. Sanghvi et al., Org. Proc. Res. Dev. 2000, 4, 175-181 non-patent document 7: Xie, C. et al., Org. Proc. Res. Dev. 2005, 9, 730-737 non-patent document 8: Gasparutto D. et al., Nucleic Acid Res. 1992, 20 (19), 5159-5166 non-patent document 9: Ohkubo, A. et al., Bioorg. Med. Chem. 2008, 16, 5345-5351

SUMMARY OF THE INVENTION

Problems to be Solved by the Invention

The problem of the present invention is to provide a method for producing a 3'-terminal-phosphoramidited oligonucleotide by a phosphitylation reaction using a phosphitylating agent more superior in preservation stability, while suppressing excessive activation of a phosphitylating agent and falling off of a protecting group on phosphoric acid, a method for producing an oligonucleotide by enabling desilylation without accompanying falling off of a cyanoethyl-protecting group, and a method for more efficiently producing oligonucleotide, a method for producing an oligonucleotide with various functional groups linked to the 3'-terminal and the like, each using the above methods.

Means of Solving the Problems

The present inventors have conducted intensive studies and found that the above-mentioned problem can be solved by utilizing diamidite as a phosphitylating agent and performing an activating method using a particular activator of the phosphitylating agent, and conducting phosphitylation in the presence of a particular base. Furthermore, the present inventor have conducted intensive studies and found a particular silyl-protecting group capable of suppressing decyanoethylation and the deprotection conditions thereof.

The present invention includes the following.

[1] A method for producing n-mer (n is any integer of two or more) oligonucleotide wherein a 5'-position hydroxyl group or 5'-position phosphoric acid group is protected and a 3'-position hydroxyl group or 3'-position amino group is not protected, the method comprising a step of reacting an n-mer oligonucleotide wherein a 5'-position hydroxyl group or 5'-position phosphoric acid group is protected and a 3'-position hydroxyl group or 3'-position amino group is protected by a silyl-protecting group with a fluoride ion source in a solvent in the presence of 1 or not less than 2 kinds of organic bases, wherein the fluoride ion source is a salt of at least one kind of the 1 or not less than 2 kinds of organic bases and hydrogen fluoride.

[2] The method of the above-mentioned [1], wherein the n-mer oligonucleotide wherein a 5'-position hydroxyl group or 5'-position phosphoric acid group is protected and a 3'-position hydroxyl group or 3'-position amino group is protected by a silyl-protecting group has the following structure (I);

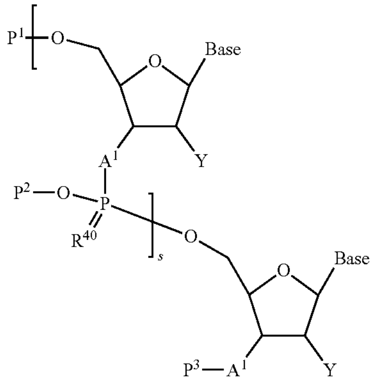

(I)

wherein $A^1$ in the number of s+1 are each independently an oxygen atom or —NH—, Base in the number of s+1 are each independently an optionally protected nucleic acid base, P' is a hydroxyl-protecting group or a phosphoric acid group as —O—$P^1$ in which one of the hydroxyl groups is replaced by —OL$''^1$-OH wherein L$''^1$ is an organic group and hydroxyl group is protected, $P^2$ in the number of s are each independently a phosphoric acid-protecting group, $R^{40}$ in the number of s are each independently an oxygen atom or a sulfur atom, Y in the number of s+1 are each independently a hydrogen atom, an optionally protected hydroxyl group, a halogen atom or an organic group that crosslinks to the 4-position carbon atom, $P^3$ is a silyl-protecting group, and s is any integer of one or more.

[3] The method of the above-mentioned [1] or [2], wherein the organic base is used in an amount of not less than 1 molar equivalent relative to the fluoride ion source.

[4] The method of any of the above-mentioned [1]-[3], wherein the organic base is a mixture of a strong base and a weak base, a mixture of not less than 2 kinds of weak bases or a single weak base.

[5] The method of the above-mentioned [4], wherein the strong base is pKa≥8 and the weak base is 4≤pKa<8.

[6] The method of any of the above-mentioned [1]-[5], wherein the strong base as the organic base is used at not more than ⅓ molar equivalents.

[7] The method of any of the above-mentioned [1]-[6], wherein one or more kinds selected from methylamine, dimethylamine, trimethylamine, ethylamine, diethylamine, triethylamine, propylamine, isopropylamine, diisopropylamine, diisopropylethylamine, butylamine, isobutylamine, tert-butylamine, 1,4-diazabicyclo [2.2.2] octane (DABCO) and morpholine is (are) used as the organic base.

[8] The method of any of the above-mentioned [1]-[7], wherein one or more kinds selected from pyridine, 2,6-dimethylpyridine, 2,4,6-trimethylpyridine, piperazine, piperidine, imidazole, N-methylimidazole, N-methylmorpholine, N-ethylmorpholine, aniline, toluidine, dimethylaniline, ethylaniline, diethylaniline, ethylmethylaniline and anisidine is (are) used as organic base.

[9] The method of any of the above-mentioned [1]-[8], wherein a mixture of triethylamine and pyridine is used as the organic base.

[10] The method of any of the above-mentioned [1]-[9], wherein the fluoride ion source is one or more kinds selected from triethylamine pentahydrofluoride, triethylamine trihydrofluoride and pyridine hydrofluoride.

[11] The method of any of the above-mentioned [1]-[10], wherein the silyl-protecting group is a silyl-protecting group in which 3 substituents on silicon are selected from an alkyl group, an aryl group, an aralkyl group, an alkoxy group, an aryloxy group, an aralkyloxy group, an alkylthio group and an arylthio group, and at least one of them is selected from an aryl group, an alkoxy group, an aryloxy group and an aralkyloxy group.

[12] The method of any of the above-mentioned [1]-[11], wherein at least one of Base in the number of s+1 is protected by a protecting group represented by the formula: -L-$Y^L$—Z wherein L is a group (linker) represented by the formula (a1):

(a1)

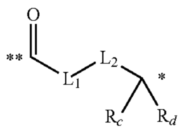

wherein ** is the bonding position to nucleic acid;

* is the bonding position to $Y^L$;

$L_1$ is an optionally substituted divalent $C_{1-22}$ hydrocarbon group, an oxygen atom or —NR— (R is a hydrogen atom, an alkyl group or an aralkyl group); and $L_2$ is a single bond or a group represented by the formula: *C($R^{3a}$)($R^{3b}$)—O—$R^1$**, formula: *C(═O)N($R^2$)—$R^1$—N($R^{3a}$)** or formula: *C(═O)N($R^2$)—$R^1$—C($R^{3a}$)($R^{3b}$)** wherein * is the bonding position to $L_1$, ** is the bonding position to $CR_cR_d$, $R^1$ is an optionally substituted $C_{1-22}$ alkylene group, $R^2$ and $R^{3a}$ are each independently a hydrogen atom or an optionally substituted $C_{1-22}$ alkyl group, or $R^2$ and $R^{3a}$ are optionally joined to form an optionally substituted $C_{1-22}$ alkylene bond, $R^{3b}$ is a hydrogen atom or an optionally substituted $C_{1-22}$ alkyl group;

$R_c$ and $R_d$ are each independently a hydrogen atom, an optionally substituted $C_{1-22}$ alkyl group or $R_c$ and $R_d$ are optionally joined to form a single carbonyl group;

$Y^L$ is a single bond, an oxygen atom, or —NR— (R is a hydrogen atom, an alkyl group or an aralkyl group), a sulfur atom; and Z is a group represented by the formula (a2):

(a2)

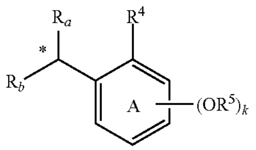

wherein * is the bonding position to $Y^L$;

$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;

$R^5$ in the number of k are each independently an organic group having an aliphatic hydrocarbon group having 10 or more carbon atoms;

k is an integer of 1-4;

ring A optionally has, in addition to $OR^5$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;

$R_a$ is a hydrogen atom or a phenyl group optionally substituted by a halogen atom; and $R_b$ is a hydrogen atom, or a group represented by the formula (a3):

(a3)

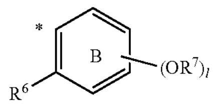

wherein * is the bonding position;

j is an integer of 0-4;

$R^7$ in the number of j are each independently an organic group having an aliphatic hydrocarbon group having 10 or more carbon atoms;

$R^6$ is a hydrogen atom, or is optionally a single bond or —O— in combination with $R^4$ to form a fluorenyl group or a xanthenyl group together with ring A; and ring B optionally has, in addition to $OR^7$ in the number of j, a substituent selected from the group consisting of a halogen atom, a $C_{1-6}$ alkyl group optionally substituted by a halogen atom, and a $C_{1-6}$ alkoxy group optionally substituted by a halogen atom;

$R_a$ and $R_b$ are optionally joined to form a single carbonyl group;

a group represented by the formula (a2');

(a2')

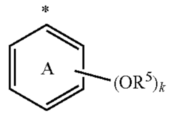

wherein * is the bonding position to $Y^L$; and other symbols are each as defined for the formula (a2), or a group represented by the formula (a2");

(a2")

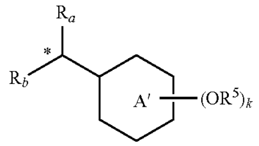

wherein * is the bonding position to $Y^{L}$' ring A' optionally has, in addition to $OR^5$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;

each symbol is as defined for the formula (a2), or a protecting group represented by the formula: —Z'

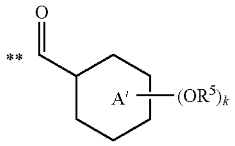

wherein ** is the bonding position to nucleic acid; and each symbol is as defined for the formula (a2").

[13] The method of the above-mentioned [12], wherein L is a succinyl group.

[14] The method of the above-mentioned [12] or [13], wherein $R^5$ and/or $R^7$ are/is an alkyl group having 10-40 carbon atoms.

[15] The method of the above-mentioned or [13], wherein $R^5$ is an octadecyl group.

[16] The method of any of the above-mentioned [1]-[15], wherein Base at the 3'-terminal nucleoside is protected by a protecting group represented by the formula: -L-$Y^L$—Z (each symbol is as defined in the above-mentioned [12]) or a protecting group represented by the formula: —Z' (each symbol is as defined in the above-mentioned [12]).

[17] A method for producing a phosphoramidited oligonucleotide comprising the following steps (1) and (2):

(1) a step including reacting a phosphitylating agent precursor represented by the following formula (1):

(I)

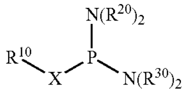

wherein

X is an oxygen atom or a sulfur atom;

$R^{10}$ is an aromatic ring, a hydroxy-protecting group or a thiol-protecting group;

$R^{20}$ and $R^{30}$ are each independently an alkyl group, and the alkyl group may be form, together with the adjacent nitrogen atom, a ring, with an activator in a solvent to prepare a phosphitylating agent represented by the following formula (2):

(2)

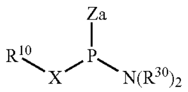

wherein

Za is a group derived from the activator, other symbols are each as defined above, (2) a step of reacting an n-mer oligonucleotide (n is any integer of two or more) in which one of a 5'-position hydroxyl group and a 5'-position phosphoric acid group, or one of a 3'-position hydroxyl group and a 3'-position amino group is protected, and the other is not protected, with the phosphitylating agent obtained in step (1) in a solvent in the presence of a base to phosphitylate a terminal hydroxyl group of the oligonucleotide.

[18] The method of the above-mentioned [17], wherein the n-mer oligonucleotide has the following structure (Ia):

(Ia)

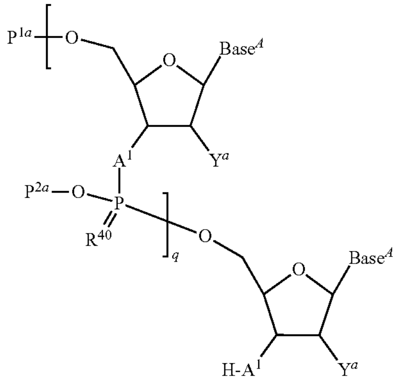

wherein $A^1$ in the number of q+1 are each independently an oxygen atom or —NH—, $Base^A$ in the number of q+1 are each independently an optionally protected nucleic acid base, $P^{1a}$ is a hydroxyl-protecting group or a phosphoric acid group as —O—$P^{1a}$ in which one of hydroxyl groups is replaced by —$OL^{n1}$-OH wherein $L^{n1}$ is an organic group and hydroxyl group is protected, $P^{2a}$ in the number of q are each independently a phosphoric acid-protecting group, $R^{40a}$ in the number of q are each independently an oxygen atom or a sulfur atom, $Y^a$ in the number of q+1 are each independently a hydrogen atom, an optionally protected hydroxyl group, a halogen atom or an 15 organic group that crosslinks to the 4-position carbon atom, and q is any integer of one or more.

[19] The method of the above-mentioned [17], wherein the n-mer oligonucleotide has the following structure (Ia'):

(Ia')

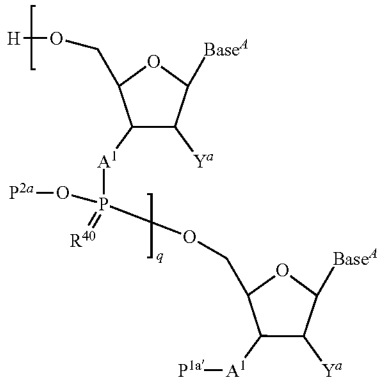

wherein $A^1$ in the number of q+1 are each independently an oxygen atom or —NH—, $Base^A$ in the number of q+1 are each independently an optionally protected nucleic acid base, $P^{1a'}$ is a hydroxyl- or amino-protecting group, or a phosphoric acid group as $-A^1-P^{1a'}$ in which one of hydroxyl groups is replaced by $—OL^{n1}-OH$ wherein $L^{n1}$ is an organic group and hydroxyl group is protected, $P^{2a}$ in the number of q are each independently a phosphoric acid-protecting group, $R^{40a}$ in the number of q are each independently an oxygen atom or a sulfur atom, $Y^a$ in the number of q+1 are each independently a hydrogen atom, an optionally protected hydroxyl group, a halogen atom or an organic group that crosslinks to the 4-position carbon atom, and q is any integer of one or more.

[20] The method of any of the above-mentioned-[19], wherein at least one of $Base^A$ in the number of q+1 is protected by a protecting group represented by the formula: $-L-Y^L—Z$ (each symbol is as defined in the above-mentioned [12]) or a protecting group represented by the formula: —Z' (each symbol is as defined in the above-mentioned [12]).

[21] The method of any of the above-mentioned [17]-[20], wherein the activator used in step (1) is a weak acidic activator with not less than pka5.

[22] The method of any of the above-mentioned [17]-[21], wherein the activator used in step (1) is an azole compound.

[23] The method of any of the above-mentioned [17]-[22], wherein the activator used in step (1) is dicyanoimidazole or dichloroimidazole.

[24] The method of any of the above-mentioned [17]-[23], wherein the activator used in step (1) is used at 1.5-20 molar equivalents relative to a phosphitylating agent precursor.

[25] The method of any of the above-mentioned [17]-[24], wherein the solvent used in step (1) dissolves the phosphitylating agent precursor, renders the activator poorly soluble and is free of an acidic or basic functional group.

[26] The method of any of the above-mentioned [17]-[25], wherein the solvent used in step (1) is one or more kinds selected from toluene, benzene, o-xylene, m-xylene, p-xylene, ethylbenzene, pentane, hexane, heptane, octane, cyclopentane, cyclohexane, diethyl ether, diisopropyl ether, tert-butyl methyl ether, cyclopentylmethylether and carbon tetrachloride.

[27] The method of any of the above-mentioned [17]-[26], wherein the solvent used in step (1) is toluene.

[28] The method of any of the above-mentioned [17]-[27], wherein the base used in step (2) is base with pka5-8.

[29] The method of any of the above-mentioned [17]-[28], wherein the base used in step (2) is one or more kinds of bases selected from collidine, N-methylmorpholine and diethylaniline.

[30] The method of any of the above-mentioned [17]-[29], comprising a step of separating an insoluble material between the step (1) and step (2).

[31] A method for producing oligonucleotide having a functional group at the 3'-terminal and represented by the following formula (Ia-2):

(Ia-2)

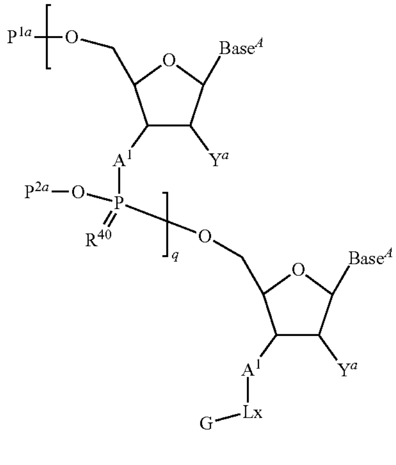

wherein $A^1$ in the number of q+1 are each independently an oxygen atom or —NH—, $Base^A$ in the number of q+1 are each independently an optionally protected nucleic acid base, $P^{1a}$ is a hydroxyl-protecting group or a phosphoric acid group as $—O—P^{1a}$ in which one of hydroxyl groups is replaced by $-OL^{n1}-OH$ wherein $L^{n1}$ is an organic group and hydroxyl group is protected, $P^{2a}$ in the number of q are each independently a phosphoric acid-protecting group, $R^{40a}$ in the number of q are each independently an oxygen atom or a sulfur atom, $Y^a$ in the number of q+1 are each independently a hydrogen atom, an optionally protected hydroxyl group, a halogen atom or an organic group that crosslinks to the 4-position carbon atom, q is any integer of one or more, Lx is a single bond or linker, and G is a functional group, the method comprising a step of obtaining a 3'-terminal phosphoramidited oligonucleotide represented by the following formula (Ia-1):

(Ia-1)

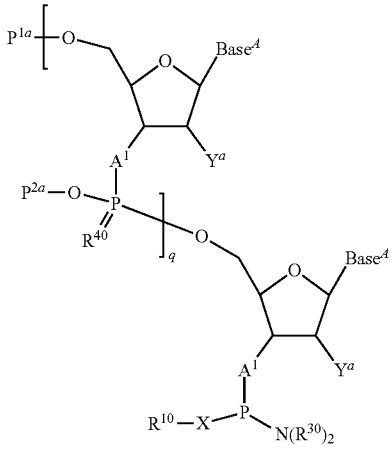

wherein

X is an oxygen atom or a sulfur atom, $R^{10}$ is an aromatic ring, a hydroxy-protecting group or a thiol-protecting group, $R^{10}$ are each independently an alkyl group, and each of other symbols is as defined above, by the method described in the above-mentioned [18], and linking a functional group to a 3'-terminal of the 3'-terminal is phosphoramidited oligonucleotide directly or via a linker.

[32] A method for producing an oligonucleotide having a functional group at the 5'-terminal and the represented by the following formula (Ia'-2):

(Ia'-2)

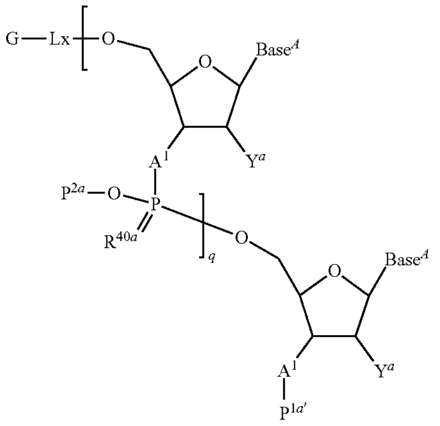

wherein $P^{1x'}$ is a hydroxyl- or amino-protecting group or a phosphoric acid group as $-A^1-P^{1a'}$ in which one of hydroxyl groups is replaced by $-OL^{n1}-OH$ wherein $L^{n1}$ is an organic group and hydroxyl group is protected, and each of other symbols is as defined in the formula (Ia-2)], the method comprising a step of obtaining a 5'-terminal phosphoramidited oligonucleotide represented by the following formula (Ia'-1):

(Ia'-1)

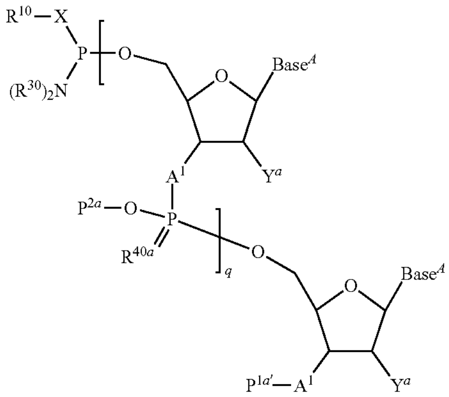

wherein $P^{1a'}$ is a hydroxyl- or amino-protecting group or a phosphoric acid group as $-A^1-P^{1a'}$ in which one of hydroxyl groups is replaced by $—OL^{n1}-OH$ wherein $L^{n1}$ is an organic group and hydroxyl group is protected, and each of other symbols is as defined in the formula (Ia-1), by the method of the above-mentioned [19], and linking a functional group to a 5'-terminal of the 5'-terminal phosphoramidited oligonucleotide directly or via a linker.

[33] The method of the above-mentioned [31] or [32], wherein at least one of $Base^A$ in the number of q+1 is protected by a protecting group represented by the formula: $-L-Y^L—Z$ (each symbol is as defined in the above-mentioned [12]) or a protecting group represented by the formula: —Z' (each symbol is as defined in the above-mentioned [12]).

[34] The method of any one of the above-mentioned [31]-[33], wherein the functional group is derived from at least one kind selected from the group consisting of oligonucleotide, mononucleoside, cholesterol, GalNac3, PEG, low molecule medicament, biotin, peptide and a labeled compound.

[35] The method of the above-mentioned [31], wherein the functional group is n'-mer oligonucleotide (n' is any integer of two or more.) in which the 3'-position hydroxyl group or 3'-position amino group or 3'-position phosphoric acid group is protected and the 5'-hydroxyl group is not protected.

[36] The method of the above-mentioned [31], wherein the functional group is n'-mer oligonucleotide (n' is any integer of two or more.) in which the 5'-position hydroxyl group is protected and a 3'-position hydroxyl group or 3'-position amino group is not protected.

[37] The method of the above-mentioned [35], wherein the n'-mer oligonucleotide has the following structure (Ib):

(Ib)

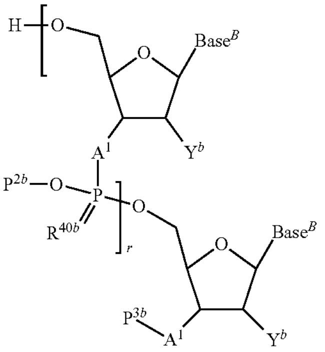

wherein $A^1$ in the number of r+1 are each independently an oxygen atom or NH, $Base^B$ in the number of r+1 are each independently an optionally protected nucleic acid base, $P^{2b}$ in the number of r are each a phosphoric acid-protecting group, $R^{40b}$ in the number of r are each an oxygen atom or a sulfur atom, $P^{3b}$ is a hydroxyl- or an amino-protecting group or a phosphoric acid group as $-A^1-P^{3b}$ in which one of hydroxyl groups is replaced by $—OL^{n1}-OH$ wherein $L^{n1}$ is an organic group and hydroxyl group is protected, $Y^b$ in the number of r+1 are each a hydrogen atom, an optionally protected hydroxyl group, halogen atom, or an organic group that crosslinks to the 4-position carbon atom, and r is any integer of one or more.

[38] The method of the above-mentioned [36], wherein the n'-mer oligonucleotide has the following structure (Ib'):

(Ib')

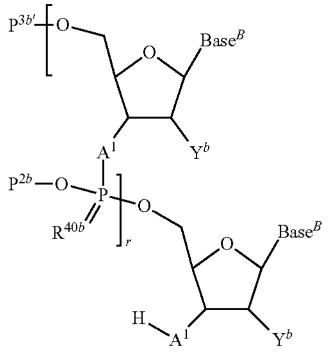

wherein $P^{3b'}$ is a hydroxyl-protecting group or a phosphoric acid group as —O—$P^{3b'}$ in which one of hydroxyl groups is replaced by —$OL^{n1}$-OH wherein $L^{n1}$ is an organic group and hydroxyl group is protected, and each of other symbols is as defined in the formula (Ib).

[39] The method of the above-mentioned [37] or [38], wherein at least one of $Base^B$ in the number of r+1 is protected by a protecting group represented by the formula: -L-$Y^L$—Z (each symbol is as defined in the above-mentioned [12]) or a protecting group represented by the formula: ~Z' (each symbol is as defined in the above-mentioned [12]).

[40] The method of any of the above-mentioned [37]-[39], wherein the hydroxyl-protecting group for $P^{3b}$ or $P^{3b'}$ is represented by the formula: -L-$Y^L$—Z (each symbol is as defined in the above-mentioned [12]) or the formula: —Z' (each symbol is as defined in the above-mentioned [12]).

[41] The method of the above-mentioned [40], wherein L is a succinyl group.

[42] A method for producing an oligonucleotide having a functional group at the 3'-terminal and represented by the following formula (II):

(II)

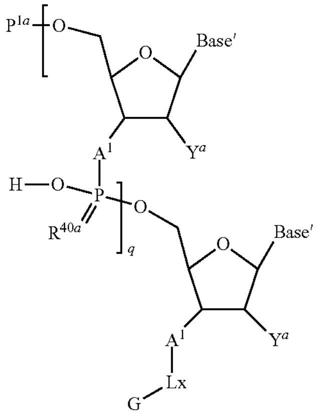

wherein

Base' in the number of q+1 are each an unprotected nucleic acid base, $A^1$ in the number of q+1 are each independently an oxygen atom or NH, $P^{1a}$ is a hydroxyl-protecting group or a phosphoric acid group as —O—$P^{1a}$ in which one of hydroxyl groups is replaced by —$OL^{n1}$-OH wherein It is an organic group and hydroxyl group is protected, $R^{40a}$ in the number of q are each independently an oxygen atom or a sulfur atom, $Y^a$ in the number of q+1 are each independently a hydrogen atom, an optionally protected hydroxyl group, halogen atom, or an organic group that crosslinks to the 4-position carbon atom, q is any integer of one or more, Lx is a single bond or linker, and G is a functional group, the method comprising a step of linking, directly or via a linker, a functional group to a 3'-terminal of a 3'-terminal phosphoramidited oligonucleotide represented by the following formula (Ia-1'):

(Ia-1')

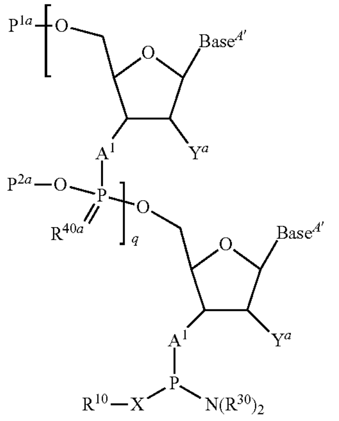

wherein $Base^{A'}$ in the number of q+1 are each independently protected by a protecting group represented by the formula: -L-$Y^L$—Z (wherein L' is succinyl group, $Y^L$ and Z are as defined in the above-mentioned [12]) or a protecting group represented by the formula: —Z' (each symbol is as defined in the above-mentioned [12]), $P^{2a}$ in the number of q are each independently a phosphoric acid-protecting group, X is an oxygen atom or a sulfur atom, $R^{10}$ is an aromatic ring, a hydroxy-protecting group or a thiol-protecting group, $R^{30}$ are each independently an alkyl group, and each of other symbols is as defined above, to give an oligonucleotide having a functional group at a 3'-terminal and represented by the following formula (Ia-2'):

(Ia-2')

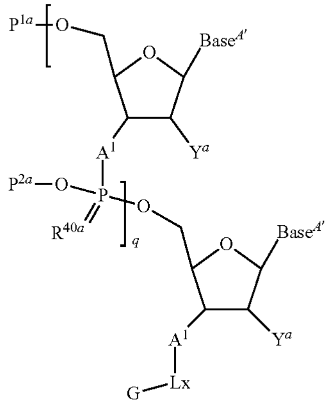

wherein each of other symbols is as defined above, and removing the protecting group.

[43] The method of the above-mentioned [42], wherein the 3'-terminal phosphoramidited oligonucleotide is obtained by the method of any of the above-mentioned [17]-[41] and thereafter the 3'-terminal phosphoramidited oligonucleotide is used.

[44] The method of the above-mentioned [42] or [43], wherein the functional group is derived from at least one kind selected from the group consisting of oligonucleotide, mononucleoside, is cholesterol, GalNac3, PEG, low molecule medicament, biotin, peptide and a labeled compound.

[45] The method of any of the above-mentioned [42]-[44], wherein the functional group is the n'-mer oligonucleotide (n' is any integer of two or more) in which the 3'-position hydroxyl group or 3'-position amino group or 3'-position phosphoric acid group is protected and the 5'-hydroxyl group is not protected.

The method of the above-mentioned [45], wherein the n'-mer oligonucleotide has the following structure (Ib):

(Ib)

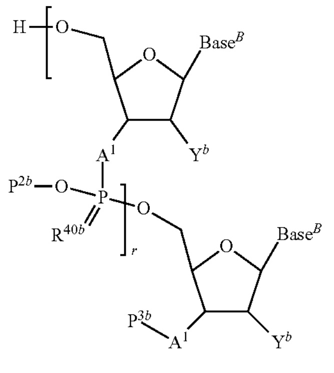

wherein $A^1$ in the number of r+1 are each independently an oxygen atom ox NH, $Base^B$ in the number of r+1 are each independently an optionally protected nucleic acid base, $P^{2b}$ in the number of r are each a phosphoric acid-protecting group, $R^{40b}$ in the number of r are each an oxygen atom or a sulfur atom, $P^{3b}$ is a hydroxyl- or amino-protecting group or a phosphoric is acid group as $-A^1-P^{3b}$ in which one of hydroxyl groups is replaced by $—OL^{n1}$-OH wherein $L^{n1}$ is an organic group and hydroxyl group is protected, $Y^b$ in the number of r+1 are each a hydrogen atom, an optionally protected hydroxyl group, halogen atom, or an organic group that crosslinks to the 4-position carbon atom, and r is any integer of one or more.

[47] The method of the above-mentioned [46], wherein at least one of $Base^B$ in the number of r+1 is protected by a protecting group represented by the formula: $-L-Y^L—Z$ (each symbol is as defined in the above-mentioned [12]) or a protecting group represented by the formula: —Z' (each symbol is as defined in the above-mentioned [12]).

[48] The method of the above-mentioned or [47], wherein the hydroxyl-protecting group for $P^{3b}$ is represented by the formula: $-L-Y^L—Z$ (each symbol is as defined in the above-mentioned [12]) or the formula: —Z' (each symbol is as defined in the above-mentioned [12]).

[49] The method of the above-mentioned [48], wherein L is a succinyl group.

[50] A compound represented by the following formula:

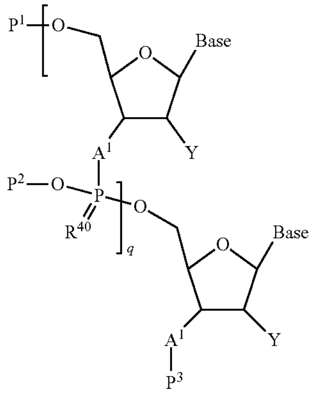

wherein $A^1$ in the number of q+1 are each independently an oxygen atom or NH,

Base in the number of q+1 are each independently an optionally protected nucleic acid base, $P^1$ is a hydroxyl-protecting group or a phosphoric acid group as $—O—P^1$ in which one of hydroxyl groups is replaced by $—OL^{n1}$-OH wherein $L^{n1}$ is an organic group and hydroxyl group is protected, $P^2$ in the number of q are each independently a phosphoric acid-protecting group, $R^{40}$ in the number of q are each independently an oxygen atom or a sulfur atom, Y in the number of q+1 are each independently a hydrogen atom, an optionally protected hydroxyl group, halogen atom, or an organic group that crosslinks to the 4-position carbon atom, $P^3$ is a silyl-protecting group, and q is any integer of one or more.

[51] The compound of the above-mentioned [50], wherein at least one of Base in the number of q+1 is protected by a protecting group represented by the formula: $-L-Y^L—Z$ (each symbol is as defined in the above-mentioned [12]) or a protecting group represented by the formula: —Z' (each symbol is as defined in the above-mentioned).

Effect of the Invention

According to the method of the present invention, a phosphitylating agent can be prepared from diamidites stable during storage and falling off of a protecting group on phosphoric acid during phosphitylation reaction can be suppressed. Therefore, phosphoramidited oligonucleotide can be produced more stably and efficiently. According to the method of the present invention, moreover, a silyl-protecting group can be eliminated without falling off of a cyanoethyl-protecting group on phosphoric acid between nucleotides. Using these methods, therefore, more efficient production of oligonucleotide and fragment condensation using same become possible.

DESCRIPTION OF EMBODIMENTS

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the specification are hereby incorporated by reference so as to describe and disclose constructed products and methodology described in, for example, publications usable in relation to the described invention.

In the present specification, the "nucleoside" to be the constituent unit of oligonucleotide means a compound wherein a nucleic acid base is bonded to the 1-position of a sugar (e.g., 2-deoxyribose or ribose, or 2-deoxyribose or ribose wherein 2-position carbon atom and 4-position carbon atom are bonded by a divalent organic group, or the like) by N-glycosidation.

In the present specification, the "sugar" also encompasses an amino sugar wherein a hydroxy group is replaced by an amino group, and ribose wherein a 2-hydroxy group is replaced by a halogen atom.

In the present specification, the "nucleotide" means a compound wherein phosphoric acid group is bonded to nucleoside and the "oligonucleotide" means a compound wherein one or more nucleotides are bonded to nucleoside. In the present specification, the "oligonucleotide" also encompasses phosphorothioate-type oligonucleotide wherein oxygen atom of phosphoric acid group is replaced by sulfur atom, oligonucleotide wherein —O— of phosphoric acid group is replaced by —NH—, and oligonucleotide wherein hydroxy group (—OH) in phosphoric acid group is replaced by —OR$^p$ wherein R$^p$ is an organic group. While the number of nucleosides in the oligonucleotide of the present invention is not particularly limited, it is preferably 3-50, more preferably 5-30.

The "3'-amino group" means an amino group bonded to the 3'-position carbon atom of nucleoside, nucleotide or oligonucleotide.

The "5'-amino group" means an amino group bonded to the 5'-position carbon atom of nucleoside, nucleotide or oligonucleotide.

The "3'-phosphoric acid group" means a phosphoric acid group bonded to the 3'-position carbon atom of nucleotide or oligonucleotide.

In the present specification, the "5'-phosphoric acid group" means a phosphoric acid group bonded to the 5'-position carbon atom of nucleotide or oligonucleotide.

In the present specification, the "phosphoric acid group" encompasses not only —O—P(O)(OH)$_2$ but also a group wherein oxygen atom is replaced by sulfur atom or NH (e.g., —O—P(S)(OH)$_2$, —NH—P(O)(OH)$_2$, —NH—P(S)(OH)$_2$). In addition, a group wherein hydroxy group (—OH) in phosphoric acid group is replaced by —OR$^p$ wherein R$^p$ is an organic group such as a protecting group of phosphoric acid group or the like (e.g., protected phosphoric acid group) is also encompassed in the "phosphoric acid group".

In the present specification, the "nucleic acid base" is not particularly limited as long as it can be used for the synthesis of nucleic acid and includes, for example, pyrimidine bases such as cytosyl group, uracil group, thyminyl group and the like, and purine bases such as adenyl group, guanyl group and the like can be mentioned. In addition to the above-mentioned groups, a modified nucleic acid base (e.g., 8-bromoadenyl group, 8-bromoguanyl group, 5-bromocytosyl group, 5-iodocytosyl group, 5-bromouracil group, 5-iodouracil group, 5-fluorouracil group, 5-methylcytosyl group, 8-oxoguanyl group, hypoxanthinyl group etc.), which is a nucleic acid base substituted by any 1 to 3 substituents (e.g., halogen atom, alkyl group, aralkyl group, alkoxy group, acyl group, alkoxyalkyl group, hydroxy group, amino group, monoalkylamino, dialkylamino, carboxy, cyano, nitro etc.) at any position(s), are also encompassed in the "nucleic acid base".

In the present specification, the "halogen atom" means a fluorine atom, a chlorine atom, a bromine atom or iodine atom.

In the present specification, the "alkyl (group)" may be a linear or a branched chain, and an alkyl group having one or more carbon number can be mentioned. When the carbon number is not particularly limited, it is preferably a $C_{1-10}$ alkyl group, more preferably a $C_{1-6}$ alkyl group. When the carbon number is not particularly limited, specific preferable examples include methyl, ethyl, propyl, isopropyl, butyl, isobutyl, sec-butyl, tert-butyl, pentyl, hexyl and the like, and methyl and ethyl are particularly preferable.

In the present specification, as the "aralkyl (group)", a $C_{7-20}$ aralkyl group can be mentioned, and a $C_{7-16}$ aralkyl group ($C_{6-10}$ aryl-$C_{1-6}$ alkyl group) is preferable. Specific preferable examples include benzyl, 1-phenylethyl, 2-phenylethyl, 1-phenylpropyl, naphthylmethyl, 1-naphthylethyl, 1-naphthylpropyl and the like, and benzyl is particularly preferable.

In the present specification, as the "alkoxy (group)", an alkoxy group having one or more carbon atoms can be mentioned. When the carbon number is not particularly limited, it is preferably a $C_{1-10}$ alkoxy group, more preferably a $C_{1-6}$ alkoxy group. When the carbon number is not particularly limited, specific preferable examples include methoxy, ethoxy, propoxy, isopropoxy, butoxy, isobutoxy, sec-butoxy, tert-butoxy, pentyloxy, hexyloxy and the like, and methoxy and ethoxy are particularly preferable.

In the present specification, examples of the "acyl (group)" include a linear or branched $C_{1-6}$ alkanoyl group, a $C_{7-13}$ aroyl group and the like. Specific examples thereof include formyl, acetyl, n-propionyl, isopropionyl, n-butyryl, isobutyryl, pivaloyl, valeryl, hexanoyl, benzoyl, naphthoyl, levulinyl and the like, each of which is optionally substituted.

In the present specification, the "alkenyl (group)" is preferably a linear or branched chain $C_{2-6}$ alkenyl group and the like. Specific examples thereof include vinyl, 1-propenyl, allyl, isopropenyl, butenyl, isobutenyl and the like. Among them, a $C_2$-$C_4$ alkenyl group is preferable.

In the present specification, the "alkynyl (group)" is preferably a linear or branched $C_{2-6}$ alkynyl group and the like. Specific examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Among them, a $C_2$-$C_4$ alkynyl group is preferable.

In the present specification, the "cycloalkyl (group)" means a cyclic alkyl group, and examples thereof include cyclopropyl, cyclobutyl, cyclopentyl, cyclohexyl, cycloheptyl, cyclooctyl and the like. Among them, a $C_3$-$C_6$ cycloalkyl group such as cyclopropyl, cyclobutyl, cyclopentyl, cyclohexyl or the like is preferable, and cyclohexyl is particularly preferable.

In the present specification, the "aryl (group)" or "aromatic ring (group)" means a monocyclic aromatic or polycyclic (fused) aromatic hydrocarbon group. Specific examples thereof include $C_{6-14}$ aryl groups such as phenyl, 1-naphthyl, 2-naphthyl, biphenylyl, 2-anthryl or the like, and the like. Among them, a $C_{6-10}$ aryl group is more preferable and phenyl is particularly preferable.

In the present specification, the "aryloxy (group)" is preferably a $C_{6-14}$ aryloxy group, and examples thereof include phenoxy, tolyloxy, xylyloxy, naphthoxy, dimethylnaphthoxy and the like.

In the present specification, the "aralkyloxy (group)" means the above-mentioned "alkyloxy (group)" substituted by the above-mentioned "aryl group", and specific examples thereof include benzyloxy, phenethyloxy, 2-phenylpropan-2-yloxy, diphenylmethyloxy and the like.

In the present specification, examples of the "hydrocarbon group" include an aliphatic hydrocarbon group, an aromatic-aliphatic hydrocarbon group, a monocyclic saturated hydrocarbon group, an aromatic hydrocarbon group and the like, and specific examples thereof include monovalent groups such as alkyl group, alkenyl group, alkynyl group, cycloalkyl group, aryl group, aralkyl group and the like and divalent groups induced therefrom.

In the present specification, the "organic group having a hydrocarbon group" means a group having the aforementioned "hydrocarbon group", and the moiety other than the "hydrocarbon group" of the "organic group having a hydrocarbon group" can be determined freely. For example, the organic group optionally has, as a linker, a moiety such as —O—, —S—, —COO—, —OCONH—, —CONH— and the like.

[a method (step) for deprotecting an olugonucleotide wherein a 3'-position hydroxyl group or 3'-position amino group is protected by a silyl-protecting group (desilylation)]

This method (step) is a method (step) for producing "n-mer (n is any integer of two or more) oligonucleotide wherein a 5'-position hydroxyl group or 5'-position phosphoric acid group is protected and a 3'-position hydroxyl group or 3'-position amino group is not protected" by deprotecting a silyl-protecting group (also referred to as desilylation) of "n-mer (n is any integer of two or more) oligonucleotide wherein a 5'-position hydroxyl group or 5'-position phosphoric acid group is protected and a 3'-position hydroxyl group or 3'-position amino group is protected by a silyl-protecting group".

The 5'-position hydroxyl-protecting group is not particularly limited as long as it can be deprotected under acidic conditions and can be used as a hydroxy-protecting group. Examples thereof include a trityl group, a 9-(9-phenyl)xanthenyl group, a 9-phenylthioxanthenyl group, di($C_{1-6}$ alkoxy)trityl groups such as a 1,1-bis(4-methoxyphenyl)-1-phenylmethyl group (dimethoxytrityl group) and the like, mono ($C_{1-18}$ alkoxy) trityl groups such as 1-(4-methoxyphenyl)-1,1-diphenylmethyl group (monomethoxytrityl group) and the like, and the like can be mentioned. Among these, a monomethoxytrityl group and a dimethoxytrityl group are preferable, and a dimethoxytrityl group is more preferable, in view of easiness of deprotection and easy availability.

The 5'-position terminal of the n-mer oligonucleotide to be desilylated may be an optionally protected phosphoric acid group. Examples of the protected phosphoric acid group at 5'-position terminal is a phosphoric acid group in which one of hydroxyl groups of the phosphoric acid group is replaced by —O$L^{n1}$-OH wherein $L^{n1}$ is an organic group and hydroxyl group is protected by a protecting group deprotectable under acidic conditions.

The organic group for $L^{n1}$ means a group in which a hydrocarbon group or a carbon atom in a hydrocarbon group is replaced by a hetero atom. Examples of the hetero atom include oxygen atom, nitrogen atom, sulfur atom and the like. The organic group may have a substituent such as hydroxy group, amino group, oxo group (=O) or the like. The hydroxy group and the amino group that the organic group may have are preferably protected by a protecting group. The shape of the organic group may be a chain (linear or branched chain), a ring or a combination of these.

The organic group may have a group having functionality to cells. The group having functionality to cells is preferably bonded to a terminal of the main chain or a side chain of the organic group. Examples of the group having functionality to cells include "a group that improves cellular membrane permeability of a compound by improving liposolubility of the compound", "a group that improves intracellular uptake of a compound via cellular membrane receptor" and the like. Examples of the "group that improves cellular membrane permeability of a compound by improving liposolubility of the compound" include cholesterol residue, tocopherol residue and the like. Examples of the "group that improves intracellular uptake of a compound via cellular membrane receptor" include N-acetylgalactosamine residue and the like.

Specific examples of —O$L^{n1}$-OH include the following (in the following formulas, * shows the bonding position to phosphorus atom and Ac is an acetyl group).

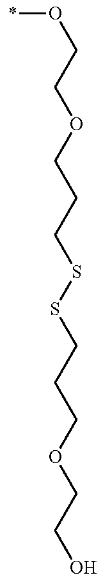

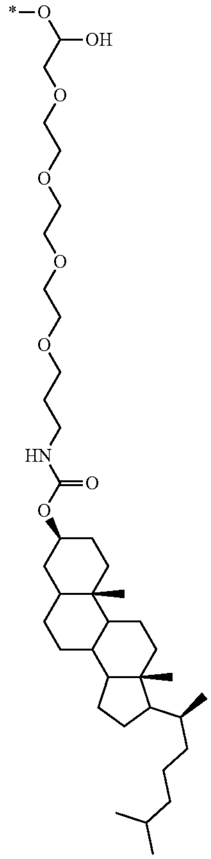

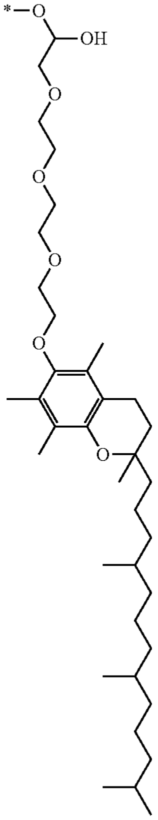

-continued

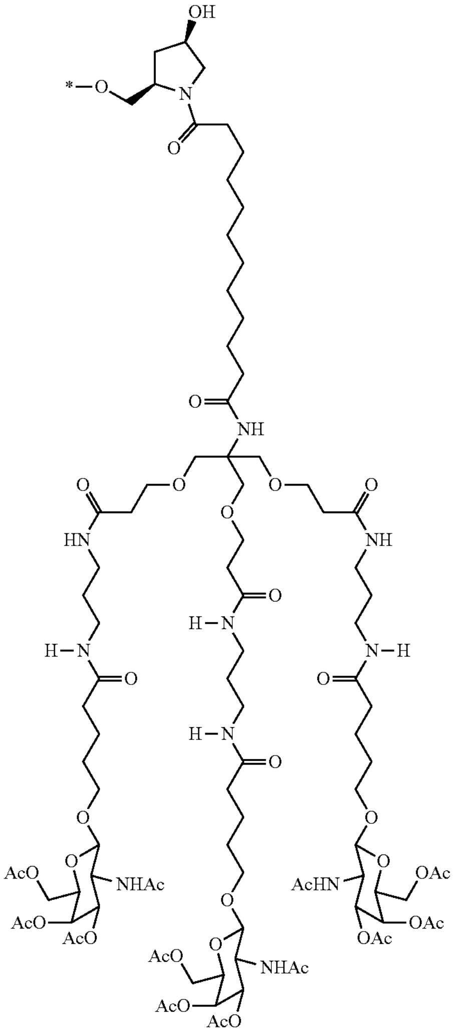 [SMILES: *OC[C@H]1C[C@@H](O)CN1C(=O)CCCCCCCCCCC(=O)NC(COCCC(=O)NCCCNC(=O)CCCCOC1OC(COC(C)=O)C(OC(C)=O)C(OC(C)=O)C1NC(C)=O)(COCCC(=O)NCCCNC(=O)CCCCOC1OC(COC(C)=O)C(OC(C)=O)C(OC(C)=O)C1NC(C)=O)COCCC(=O)NCCCNC(=O)CCCCOC1OC(COC(C)=O)C(OC(C)=O)C(OC(C)=O)C1NC(C)=O]

As to the silyl protecting group of the 3'-position hydroxyl group or 3'-position amino group, for example, a silyl group wherein the substituent on silicon is selected from alkyl group, aryl group, aralkyl group, alkoxy group, aryloxy group, aralkyloxy group, alkylthio group and arylthio group and at least one of the three substituents is selected from aryl group, alkoxy group, aryloxy group and aralkyloky group can be mentioned. Specifically, tert-butyldimethylsilyl (TBDMS), diisopropylphenylsilyl (DIPPS), tert-butoxy diphenylsilyl (TBODPS), isopropoxydiisopropylsilyl (IPO-DIPS) and the like can be mentioned, with preference given to DIPPS.

Preferably, the "n-mer (n is any integer of two or more) oligonucleotide wherein a 5'-position hydroxyl group or 5'-position phosphoric acid group is protected and a 3'-position hydroxyl group or 3'-position amino group is protected by a silyl-protecting group" is a compound having the following structure (I) (hereinafter compound (I)):

(I)

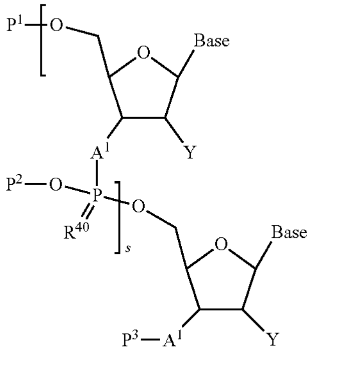

wherein $A^1$ in the number of s+1 are each independently an oxygen atom or —NH—, Base in the number of s+1 are each independently an optionally protected nucleic acid base, $P^1$ is a hydroxyl-protecting group or a phosphoric acid group as —O—$P^1$ in which one of the hydroxyl groups is replaced by —$OL''^1$-OH wherein $L''^1$ is an organic group and hydroxyl group is protected, $P^2$ in the number of s are each independently a phosphoric acid-protecting group, $R^{40}$ in the number of s are each independently an oxygen atom or a sulfur atom, Y in the number of s+1 are each independently a hydrogen atom, an optionally protected hydroxyl group, a halogen atom or an organic group that crosslinks to the 4-position carbon atom, $P^3$ is a silyl-protecting group, and s is any integer of one or more.

As the hydroxyl-protecting group for $P^1$, those similar to the above-mentioned 5'-position hydroxyl-protecting group exemplified above can be used. It is preferably a dimethoxytrityl group. As the phosphoric acid group for $P^1$ in which one of hydroxyl groups is replaced by —$OL''^1$-OH wherein $L''^1$ is an organic group and hydroxyl group is protected, those similar to the protected phosphoric acid group described in the above-mentioned 5'-position terminal can be used.

The phosphoric acid-protecting group for $P^2$ is not particularly limited as long as it can be deprotected under basic conditions and can be used as a phosphoric acid-protecting group, and a group represented by —$CH_2CH_2$WG (WG is an electron-withdrawing group) is preferable and WG is preferably a cyano group.

$R^{40}$ are preferably the same and each is an oxygen atom or a sulfur atom.

The optionally protected hydroxyl-protecting group for Y is not particularly limited and, for example, any protecting groups described in Greene's PROTECTIVE GROUPS IN ORGANIC SYNTHESIS, 4th edition, JOHN WILLY&SONS, 2006 and the like can be mentioned. Specifically, methyl, benzyl, p-methoxybenzyl, tert-butyl, methoxymethyl, methoxyethyl, 2-tetrahydropyranyl, ethoxyethyl, cyanoethyl, cyanoethoxymethyl, phenylcarbamoyl, 1,1-dioxothiomorpholine-4-thiocarbamoyl, acetyl, pivaloyl, benzoyl, trimethylsilyl, triethylsilyl, triisopropylsilyl, tert-butyldimethylsilyl, [(triisopropylsilyl)oxy]methyl (Tom), 1-(4-chlorophenyl)-4-ethoxypiperidin-4-yl (Cpep) group and the like can be mentioned. Among these, triethylsilyl group, triisopropylsilyl group and tert-butyldimethylsilyl group are preferable. From the aspects of economic efficiency and easy availability, tert-butyldimethylsilyl group is particularly preferable.

The "organic group that crosslinks to the 4-position carbon atom" for Y is not particularly limited as long as it crosslinks the 2-position and the 4-position of nucleoside and, for example, a $C_{2-7}$ alkylene group can be mentioned. The alkylene group may be interrupted at one or more (preferably 1 or 2) positions with, for example, a linker selected from —O—, —$NR^{37}$— ($R^{37}$ is a hydrogen atom or a $C_{1-6}$ alkyl group), —S—, —CO—, —COO—, —$OCONR^{38}$— ($R^{38}$ is a hydrogen atom or a $C_{1-6}$ alkyl group), —$CONR^{39}$— ($R^{39}$ is a hydrogen atom or a $C_{1-6}$ alkyl group) and the like.

The "organic group that crosslinks to the 4-position carbon atom" is preferably, for example, —ORi (Ri is a $C_{1-6}$ alkylene group that crosslinks to the 4-position), —O—$NR^{37}$—Rj (Rj is a $C_{1-6}$ alkylene group that crosslinks to the 4-position and $R^{37}$ is as defined above), —O—Rk-O—Rl (Rk is a $C_{1-6}$ alkylene group and Rl is a $C_{1-6}$ alkylene group that crosslinks to the 4-position) or the like. The $C_{1-6}$ alkylene groups for Ri, Rj, Rk and Rl are preferably each independently a methylene group or an ethylene group.

As the "organic group that crosslinks to the 4-position carbon atom", —O—$CH_2$—, —O—$CH_2$—$CH_2$—, —O—$NR^{37}$—$CH_2$— ($R^{37}$ is as defined above), —O—$CH_2$—O—$CH_2$— or the like is preferably, and —O—$CH_2$—, —O—$CH_2$—$CH_2$—, —O—NH—$CH_2$—, —O-NMe-$CH_2$—, —O—$CH_2$—O—$CH_2$— (in each of which the left side binds to the 2-position and the right side binds to the 4-position) or the like is more preferable.

As the silyl-protecting group for $P^3$, those similar to the silyl-protecting group of the above-mentioned 3'-position hydroxyl group exemplified above can be used.

The "optionally protected nucleic acid base" for Base means, for example, that an amino group may be protected in an adenyl group, a guanyl group or a cytosyl group, which is a nucleic acid base having an amino group, and a nucleic acid base wherein the amino group therein is protected by a protecting group sustainable under the deprotection conditions of the 5'-position is preferable. The "amino-protecting group" is not particularly limited, and examples thereof include the protecting groups described in Greene's PROTECTIVE GROUPS IN ORGANIC SYNTHESIS, 4th edition, JOHN WILLY&SONS, 2006 and the like. Specific examples of the "amino-protecting group" include pivaloyl group, pivaloyloxymethyl group, trifluoroacetyl group, phenoxyacetyl group, 4-isopropylphenoxyacetyl group, 4-tert-butylphenoxyacetyl group, acetyl group, benzoyl group, isobutyryl group, dimethylformamidinyl group, 9-fluorenylmethyloxycarbonyl group and the like. Of these, phenoxyacetyl group, 4-isopropylphenoxyacetyl group, acetyl group, benzoyl group, isobutyryl group, and dimethylformamidinyl group are preferable. In addition, the carbonyl group of the nucleic acid base is also optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methylsulfonyl) ethanol, 2-(phenylsulfonyl) ethanol, 2-cyanoethanol, 2-(trimethylsilyl) ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride and the like. In some cases, the carbonyl-protecting group does not need to be particularly introduced.

As the nucleic acid base-protecting group, the protecting group (a group having $C_{5-30}$ straight chain or branched chain alkyl group and/or $C_{5-30}$ straight chain or branched chain alkenyl) described in WO 2013/122236 can also be used.

As the nucleic acid base-protecting group, a protecting group represented by the following formula: -L-$Y^L$—Z, or a protecting group represented by the formula: —Z' can also be used. The protecting group is a protecting group simultaneously satisfying the reactivity and easiness of work-up, by binding to a reactive substrate to solubilize same in a non-polar solvent, thus enabling reaction in the liquid phase, and forming precipitation upon addition of a polar solvent to enable solid-liquid separation, and stable under acidic conditions capable of removing the 5'-terminal hydroxyl-protecting group. Therefore, at least one of Base present in the number of s+1 is preferably protected by a protecting group represented by (1) formula: -L-$Y^L$—Z or (2) formula: —Z'.

-L-$Y^L$—Z (1)

wherein

L is a group (linker) represented by the formula (a1):

(a1)

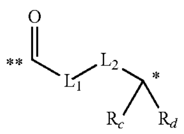

wherein ** is the bonding position to nucleic acid;

* is the bonding position to $Y^L$;

$L_1$ is an optionally substituted divalent $C_{1-22}$ hydrocarbon group, an oxygen atom or —NR— (R is a hydrogen atom, an alkyl group or an aralkyl group); and $L_2$ is a single bond or a group represented by the formula: *C($R^{3a}$)($R^{3b}$)—O—$R^1$**, formula: *C(=O)N($R^2$)—$R^1$—N($R^{3a}$)** or formula: *C(=O)N($R^2$)—$R^1$—C($R^{3a}$)($R^{3b}$)* wherein * is the bonding position to $L_1$, ** is the bonding position to $CR_cR_d$, $R^1$ is an optionally substituted $C_{1-22}$ alkylene group, $R^2$ and $R^{3a}$ are each independently a hydrogen atom or an optionally substituted $C_{1-22}$ alkyl group, or $R^2$ and $R^{3a}$ are optionally joined to form an optionally substituted $C_{1-22}$ alkylene bond, $R^{3b}$ is a hydrogen atom or an optionally substituted $C_{1-22}$ alkyl;

$R_c$ and $R_d$ are each independently a hydrogen atom, an optionally substituted $C_{1-22}$ alkyl group or $R_c$ and $R_d$ are optionally joined to form a single carbonyl group;

$Y^L$ is a single bond, an oxygen atom, or —NR— (R is a hydrogen atom, an alkyl group or an aralkyl group), a sulfur atom; and Z is a group represented by the formula (a2):

(a2)

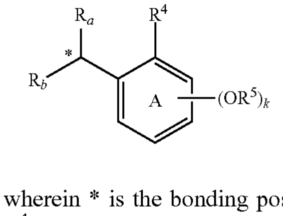

wherein * is the bonding position to $Y^L$;

$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;

$R^5$ in the number of k are each independently an organic group having an aliphatic hydrocarbon group having 10 or more carbon atoms;

k is an integer of 1-4;

ring A optionally has, in addition to $OR^5$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;

$R_a$ is a hydrogen atom or a phenyl group optionally substituted by a halogen atom; and $R_b$ is a hydrogen atom, or a group represented by the formula (a3):

(a3)

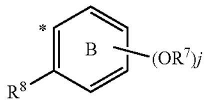

wherein * is the bonding position to $Y^L$;

j is an integer of 0-4;

$R^7$ in the number of j are each independently an organic group having an aliphatic hydrocarbon group having 10 or more carbon atoms;

$R^6$ is a hydrogen atom, or is optionally a single bond or —O— in combination with $R^4$ to form a fluorenyl group or a xanthenyl group together with ring A; and ring B optionally has, in addition to $OR^7$ in the number of j, a substituent selected from the group consisting of a halogen atom, a $C_{1-6}$ alkyl group optionally substituted by a halogen atom, and a $C_{1-6}$ alkoxy group optionally substituted by a halogen atom;

$R_a$ and $R_b$ are optionally joined to form a single carbonyl group;

a group represented by the formula (a2'):

(a2')

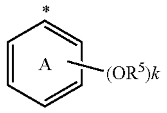

wherein * is the bonding position to $Y^L$; and other symbols are each as defined for the formula (a2), or a group represented by the formula (a2");

(a2")

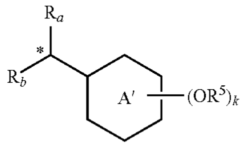

wherein * is the bonding position to $Y^L$;

ring A' optionally has, in addition to $OR^5$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;

each symbol is as defined for the formula (a2), or

—Z' (2) formula:

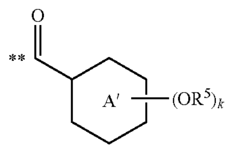

wherein ** is the bonding position to nucleic acid; and each symbol is as defined for the formula (a2").

Preferable embodiment of the linker L represented by the above-mentioned formula (a1) is a group wherein, in the formula (a1), $L_1$ is a $C_{1-6}$ alkylene group;

$L_2$ is a single bond, or a group of the formula: *C($R^{3a}$)($R^{3b}$)—O—$R^1$**, formula: *C(═O)N($R^2$)—$R^1$—N($R^{3a}$)** or formula: *C(═O)N($R^2$)—$R^1$—C($R^{3a}$)($R^{3b}$)** wherein * is the bonding position to Li, ** is the bonding position to C═O, $R^1$ is a $C_{1-6}$ alkylene group, and $R^2$, $R^{3a}$ and $R^{3b}$ are each independently a hydrogen atom or an optionally substituted $C_{1-6}$ alkyl group, or $R^2$ and $R^{3a}$ are optionally joined to form an optionally substituted $C_{1-6}$ alkylene bond; and $R_c$ and $R_d$ are each independently a hydrogen atom, or $R_c$ and $R_d$ are optionally joined to form a single carbonyl group.

Preferable embodiment of the linker L represented by the above-mentioned formula (a1) is a group wherein, in the formula (a1), $L_1$ is an ethylene group;

$L_2$ is a single bond; and $R_c$ and $R_d$ are optionally joined to form a single carbonyl group.

Preferable embodiment of the linker L represented by the above-mentioned formula (a1) is a group wherein, in the formula (a1), Li is an ethylene group;

N($R^2$)—$R^1$—N($R^{3a}$) moiety in $L_2$ is a piperazinylene group; and $R_c$ and $R_d$ are optionally joined to form a single carbonyl group.

Another preferable embodiment of the linker L represented by the above-mentioned formula (a1) is a group wherein, in the formula (a1), $L_1$ is an ethylene group;

$L_2$ is a group represented by the formula: *C(═O)N($R^2$)—$R^1$—N($R^{3a}$)** wherein * is the bonding position to $L_1$, ** is the bonding position to C═O, $R^1$ is a pentylene group or a hexylene group, and $R^2$ and $R^{3a}$ are each independently a hydrogen atom or a methyl group; and $R_c$ and $R_d$ are optionally joined to form a single carbonyl group.

Preferable embodiment of the linker L represented by the above-mentioned formula (a1) is a group wherein, in the formula (a1), $L_1$ is an ethylene group;

N($R^2$)—$R^1$—C($R^{3a}$)($R^{3b}$) moiety in $L_2$ is a piperidinylene group; and $R_c$ and $R_d$ are optionally joined to form a single carbonyl group.

Another preferable embodiment of the linker L represented by the above-mentioned formula (a1) is a group wherein, in the formula (a1), Li is a methylene group or an ethylene group;

$L_2$ is a single bond; and $R_c$ and $R_d$ are each a hydrogen atom.

Another preferable embodiment of the linker L represented by the above-mentioned formula (a1) is a group wherein, in the formula (a1), $L_1$ is a butylene group;

$L_2$ is a single bond; and $R_c$ and $R_d$ are optionally joined to form a single carbonyl group.

Another preferable embodiment of the linker L represented by the above-mentioned formula (a1) is a group wherein, in the formula (a1), $L_1$ is a methylene group;

C($R^{3a}$)($R^{3b}$)—O—$R^1$ moiety in $L_2$ is —$CH_2$—O—$CH_2$—; and $R_c$ and $R_d$ are optionally joined to form a single carbonyl group.

A particularly preferable example of the above-mentioned linker L is a succinyl group since it is economical and easily available.

Preferable embodiment of Z is a group represented by the formula (a2), the formula (a2') or the formula (a2").

Preferable embodiment of Z represented by the above-mentioned formula (a2) or the formula (a2") is a group wherein, in the formula (a2) or the formula (a2"), Ra and Rp are both hydrogen atoms;

$R^4$ is a hydrogen atom, $R^5$ in the number of k are each independently an organic group having an aliphatic hydrocarbon group having 10 or more carbon atoms (e.g., $C_{10-40}$ alkyl group); and k is an integer of 1 to 3.

Also, an embodiment wherein $R^a$ and Rp are optionally joined to form a single carbonyl group is also preferable.

Another preferable embodiment of Z represented by the above-mentioned formula (a2) or the formula (a2") is a group wherein, in the formula (a2) or the formula (a2"), k is an integer of 1 to 3;

$R_a$ and $R_b$ are both hydrogen atoms;

$R^4$ is a hydrogen atom;

$R^5$ in the number of k are each independently benzyl group having 1 to 3 aliphatic hydrocarbon groups having 10 or more carbon atoms, or a cyclohexyl group having 1 to 3 aliphatic hydrocarbon groups having 10 or more carbon atoms; and ring A optionally has, in addition to $OR^5$ in the number of k, a substituent selected from the group consisting of a halogen atom, a $C_{1-6}$ alkyl group optionally substituted by a halogen atom, and a $C_{1-6}$ alkoxy group optionally substituted by a halogen atom.

Another preferable embodiment of Z represented by the above-mentioned formula (a2) or the formula (a2") is a group wherein, in the formula (a2) or the formula (a2"), $R_a$ is a hydrogen atom;

$R_b$ is a group represented by the above-mentioned formula (a3) wherein * shows a bonding position; j is an integer of 0 to 3;

$R^7$ in the number of j are each independently a $C_{10-40}$ alkyl group; and $R^4$ and $R^6$ are both hydrogen atoms.

Another preferable embodiment of Z represented by the above-mentioned formula (a2) or the formula (a2") is a group wherein, in the formula (a2) or the formula (a2"), $R_a$ is a hydrogen atom;

$R_b$ is a group represented by the above-mentioned formula (a3) wherein * shows a bonding position; j is an integer of 0 to 3;

$R^7$ in the number of j are each independently a $C_{10-40}$ alkyl group; and $R^6$ is joined with $R^4$ of ring A to form a single bond or —O—, and therefore, ring A and ring B form a fluorenyl group or a xanthenyl group in combination.

Preferable embodiment of Z represented by the above-mentioned formula (a2') is a group wherein, in the formula (a2'), $R^5$ in the number of k are each independently an organic group having an aliphatic hydrocarbon group having 10 or more carbon atoms (e.g., $C_{10-40}$ alkyl group); and k is an integer of 1 to 3.

In the above-mentioned formula: —Z', $R^5$ in the number of k are each independently an organic group having an aliphatic hydrocarbon group having 10 or more carbon atoms (e.g., $C_{10-40}$ alkyl group); and k is an integer of 1 to 3.

As the protecting group represented by the above-mentioned formula: -L-$Y^L$—Z or the protecting group represented by the above-mentioned formula: —Z', a group difficult to cleave under acidic conditions permitting removal of the protecting group of nucleotide terminal hydroxyl and easy to cleave under basic conditions is preferable. Representative examples of such protecting group include a group wherein L in the formula: -L-$Y^L$—Z is a group represented by the above-mentioned formula (a1) (preferably a succinyl group etc.), and $Y^L$—Z is the following group; and a group wherein a group represented by the formula: —Z' is the following group:

3,4,5-tris(octadecyloxy)benzyloxy group,
3,5-bis(docosyloxy)benzyloxy group,
3,5-bis[3',4',5'-tri(octadecyloxy)benzyloxy]benzyloxy group,
3,4,5-tris[3',4',5'-tri(octadecyloxy)benzyloxy]benzylamino group,
3,4,5-tris(octadecyloxy)benzylamino group,
2,4-bis(docosyloxy)benzylamino group,
3,5-bis(docosyloxy)benzylamino group,
bis(4-docosyloxyphenyl)methylamino group,
4-methoxy-2-[3',4',5'-tris(octadecyloxy)benzyloxy]benzylamino group,
4-methoxy-2-[3',4',5'-tris(octadecyloxy)cyclohexylmethyloxy]benzylamino group,
2,4-bis(dodecyloxy)benzylamino group,
phenyl(2,3,4-tris(octadecyloxy)phenyl)methylamino group,
di[4-(12-docosyloxydodecyloxy)phenyl]methylamino group,
3,5-bis[3',4',5'-tri(octadecyloxy)benzyloxy]benzylamino group, and
3,4,5-tris[3',4',5'-tri(octadecyloxy)benzyloxy]benzylamino group.

The following is a scheme when the present method (step) is performed using compound (I) as a starting material.

Desilylation

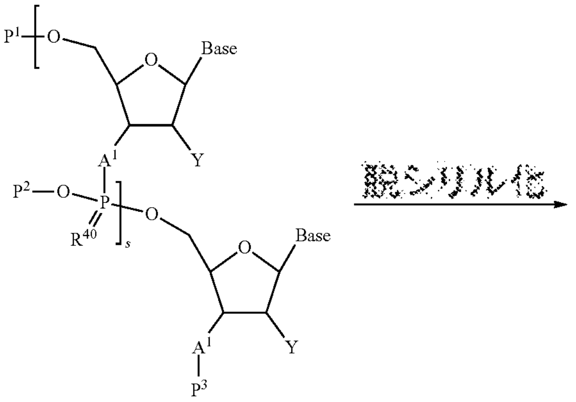

-continued

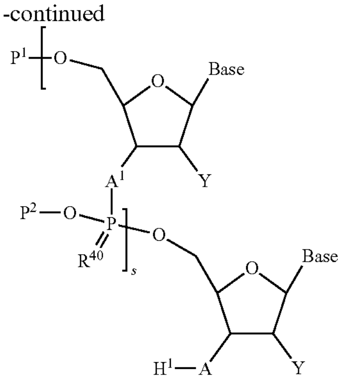

wherein each symbol is as defined above.

While the solvent to be used in this method (step) is not particularly limited as long as it dissolves a substrate and is not an acid and the reaction proceeds, halogenated hydrocarbon solvents such as dichloromethane, 1,2-dichloroethane, chloroform, carbon tetrachloride and the like, aromatic hydrocarbon solvents such as benzene, toluene, xylene and the like, aliphatic hydrocarbon solvents such as pentane, hexane, heptane, octane and the like, ether solvents such as diethylether, tetrahydrofuran, cyclopentyl methyl ether and the like, and mixed solvents thereof are preferable. Of these, a mixed solvent of tetrahydrofuran and dichloromethane is preferable, and a 2:1 mixed solvent is particularly preferable.

Desilylation is performed by reacting a fluoride ion source in the presence of an organic base. As the organic base, a mixture of 1 or not less than 2 kinds is used, and it is characterized in that a salt of at least one kind of the bases and hydrogen fluoride is used as the fluoride ion source.

The organic base may be a mixture of a strong base and a weak base, a mixture of not less than 2 kinds of weak bases or single weak base.

The strong base preferably has pKa≥8 and is specifically an amine such as methylamine, dimethylamine, trimethylamine, ethylamine, diethylamine, triethylamine, propylamine, isopropylamine, diisopropylamine, diisopropylethylamine, butylamine, isobutylamine, tert-butylamine, 1,4-diazabicyclo[2.2.2]octane (DABCO) or morpholine, preferably triethylamine. The weak base preferably has 4≤pKa<8 and is specifically a heterocyclic compound such as pyridine, 2,6-dimethylpyridine, 2,4,6-trimethylpyridine, piperazine, piperidine, imidazole, N-methylimidazole, N-methylmorpholine, N-ethylmorpholine or the like, or an aniline such as aniline, toluidine, dimethylaniline, diethylaniline, ethylaniline, ethylmethylaniline, anisidine or the like. Preferred is pyridine or N-methylmorpholine, more preferred is pyridine.

The organic base is preferably used in a proportion of not less than 1 mol equivalent relative to fluoride ion.

When the organic base is a mixture of a strong base and a weak base, the amount of each to be used can be appropriately determined within the range free from an adverse influence on the desired reaction. It is preferable to avoid using an excessively strong base since decyanoethylation may occur on thiophosphoric acid. A strong base is generally used in a proportion of ⅓ molar equivalents or less relative to fluoride ion. A weak base is used in a total amount of at least 1 mol equivalent or more with a strong base. Even when a strong base is used in an amount of not more than ⅓ molar equivalents, 5'-terminal protecting group falls off unless a weak base is used in a total amount of at least 1 mol equivalent or more with a strong base. The amount of the weak base to be used is not particularly limited as long as it dissolves a substrate.

The fluoride ion source is a salt of at least one kind of the above-mentioned base and hydrogen fluoride, and triethylamine pentahydrofluoride (5HF-TEA), triethylamine trihydrofluoride (3HF-TEA), pyridine hydrofluoride (HF-pyridine) and the like can be specifically mentioned, with preference given to 3HF-TEA.

This method (step) affords a mixture of the above-mentioned fluoride ion source added with an organic base, preferably a mixture of hydrogen fluoride salt of a strong base added with a weak base, more preferably, a mixture of 5HF-TEA or 3HF-TEA added with pyridine, particularly preferably a mixture of 3HF-TEA added with pyridine (3HF-TEA-pyridine). A weak base may be added to a hydrogen fluoride salt of a weak base. For example, N-methylmorpholine may be added to HF-pyridine.

The reaction temperature and reaction time of this method (step) are not particularly limited as long as the substrate or resultant product is not precipitated, and are generally-10 to 80° C., preferably 0 to 40° C., more preferably 10 to 20° C., generally 0.5 to 96 hr, preferably 1 to 48 hr, more preferably 1 to 24 hr.

[Production Method of Phosphoramidited Oligonucleotide]

This method includes reactions for monoselectively activating a phosphitylating agent precursor having two nitrogen substituents on a trivalent phosphorus to give a phosphitylating agent, and phosphitylating a free 3'-terminal or 5'-terminal of oligonucleotide by using the agent in the presence of a base.

That is, this method is a production method of phosphoramidited oligonucleotide including the following steps (1) and (2).

(1) A step including reacting a phosphitylating agent precursor represented by the following formula (1):

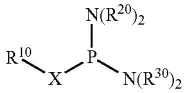
(1)

wherein

X is an oxygen atom or a sulfur atom;

$R^{10}$ is an aromatic ring, a hydroxy-protecting group or a thiol-protecting group;

$R^{20}$ and $R^{30}$ are each independently an alkyl group, and the alkyl group may form, together with the adjacent nitrogen atom, a ring, with an activator in a solvent to prepare a phosphitylating agent represented by the following formula (2):

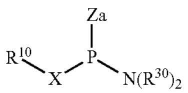
(2)

wherein

Za is a group derived from the activator; and other symbols are each as defined above, and (2) a step of reacting an n-mer oligonucleotide (n is any integer of two or more) in which one of a 5'-position hydroxyl group and a 3'-position hydroxyl group is protected, and the other is not protected, with the phosphitylating agent obtained in step (1) in a solvent in the presence of a base to phosphitylate a terminal hydroxyl group of the oligonucleotide.

Step (1)

In the formula (1), as the aromatic ring for Rio, phenyl, 4-nitrophenyl, 2,4-dinitrophenyl, pentafluorophenyl, pentachlorophenyl, 2-bromophenyl, 4-bromophenyl, 2-methylphenyl, 2,6-dimethylphenyl and the like can be mentioned, and 4-nitrophenyl is preferable.

In the formula (1), examples of the hydroxy-protecting group or the thiol-protecting group for $R^{10}$ include $C_{1-6}$ alkyl group (e.g., methyl, ethyl, n-propyl, isopropyl, n-butyl, isobutyl, s-butyl, t-butyl, pentyl, isopentyl); cyanated $C_{1-6}$ alkyl group (e.g., 2-cyanoethyl, 2-cyano-1,1-dimethylethyl); ethyl group substituted by a substituted silyl group (e.g., 2-methyldiphenylsilylethyl, 2-trimethylsilylethyl, 2-triphenylsilylethyl); halogenated $C_{1-6}$ alkyl group (e.g., 2,2,2-trichloroethyl, 2,2,2-tribromoethyl, 2,2,2-trifluoroethyl); $C_{2-6}$ alkenyl group (e.g., ethenyl, 1-propenyl, 2-propenyl, 1-methyl-2-propenyl, 1-methyl-1-propenyl); $C_{3-6}$ cycloalkyl group (e.g., cyclopropyl, cyclobutyl, cyclopentyl, cyclohexyl); cyanated $C_{1-6}$ alkenyl group (e.g., 2-cyanobutenyl); $C_{7-11}$ aralkyl group (e.g., benzyl, α-naphthylmethyl, β-naphthylmethyl); and $C_{6-10}$ aryl group (e.g., phenyl, indenyl, naphthyl), more preferably cyanated $C_{1-6}$ alkyl group, particularly preferably 2-cyanoethyl.

In the formula (p), $R^{20}$ and $R^{30}$ are each independently an alkyl group, and the alkyl group may form, together with the adjacent nitrogen atom, a ring (e.g., pyrrolidine). $R^{20}$ and $R^{30}$ are each preferably an isopropyl group.

As the phosphitylating agent precursor, the following compound is particularly preferable.

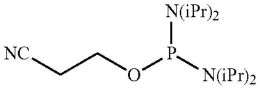

A phosphitylating agent is obtained by reacting a phosphitylating agent precursor with an activator.

An activator is an acid capable of substituting an amine on phosphoramidite to afford a reactive substituent with a hydroxy group and the like. To be specific, a weakly acidic activator with pKa of not less than 5, more preferably at least one kind selected from an azole compound with pka of not less than 5 and a C-substituted product thereof. As the azole compound, tetrazole, triazole, imidazole and the like can be mentioned, as the C-substituted product, a compound disubstituted with a halogen atom such as dicyanoimidazole, bis(trifluoromethyl) imidazole, dichloroimidazole or the like is used. Particularly preferred are dicyanoimidazole and dichloroimidazole.

In the formula (2), Za is a group derived from the activator and, for example, a group obtained by removing one hydrogen atom from the activator. When dicyanoimidazole is used as an activator, Za is dicyanoimidazolyl and when dichloroimidazole is used as an activator, Za is dichloroimidazolyl.

The solvent to be used in step (1) is not particularly limited as long as a phosphitylating agent precursor can be dissolved and an activator becomes poorly soluble, and is generally free of an acidic or basic functional group. As used herein, being "poorly soluble" approximately means that the concentration of the activator in a solvent is not more than 6 μM. Specifically, toluene, benzene, o-xylene, m-xylene, p-xylene, ethylbenzene, pentane, hexane, heptane, octane, cyclopentane, cyclohexane, diethyl ether, diisopropyl ether, tert-butyl methyl ether, cyclopentyl methyl ether, carbon tetrachloride and the like can be mentioned, toluene and cyclohexane are preferable, and toluene is particularly preferable.

The reaction temperature and reaction time of this method (step) are not particularly limited as long as the substrate or resultant product is not precipitated, and are generally not more than 40° C., preferably 0-30° C., more preferably 5-15° C., particularly preferably about 10° C., generally 0.5-24 hr, preferably 1-12 hr, more preferably 1-6 hr.

The amount of the activator and phosphitylating agent precursor to be used is not particularly limited as long as the phosphitylating agent precursor is activated, and it is generally an excess amount, preferably 1.5-10 molar equivalents, relative to the phosphitylating agent precursor. By reacting an excess amount of an activator with a phosphitylating agent precursor in a solvent, the phosphitylating agent precursor is activated and diisopropylamine by-produced in phosphitylating is simultaneously precipitated as a salt with the activator. Therefore, where necessary, a step for separating insoluble materials such as precipitate and the like can be performed between step (1) and the following step (2), and is preferably performed.

Step (2)

This step includes a step of reacting an n-mer oligonucleotide (n is any integer of two or more) in which one of a 5'-position hydroxyl group and a 5'-position phosphoric acid group, or one of a 3'-position hydroxyl group and a 3'-position amino group is protected, and the other is not protected, with the phosphitylating agent obtained in step (1) in a solvent in the presence of a base to phosphitylate a terminal hydroxyl group of the oligonucleotide.

Preferable one embodiment of the "n-mer oligonucleotide (n is any integer of two or more) in which one of a 5'-position hydroxyl group and a 5'-position phosphoric acid group, or one of a 3'-position hydroxyl group and a 3'-position amino group is protected, and the other is not protected" is a compound having the following structure (Ia) in which a 5'-position hydroxyl group or 5'-position phosphoric acid group is protected and a 3'-position hydroxyl group or 3'-position amino group is not protected (hereinafter compound (Ia)).

(Ia)

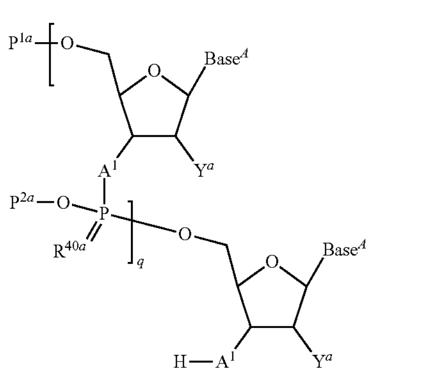

wherein $A^1$ in the number of q+1 are each independently an oxygen atom or —NH—, $Base^A$ in the number of q+1 are each independently an optionally protected nucleic acid base, $P^{1a}$ is a hydroxyl-protecting group or a phosphoric acid group as —O—$P^{1a}$ in which one of hydroxyl groups is replaced by —$OL^{n1}$-OH wherein $L^{n1}$ is an organic group and hydroxyl group is protected, $P^{2a}$ in the number of q are each independently a phosphoric acid-protecting group, $R^{40a}$ in the number of q are each independently an oxygen atom or a sulfur atom, $Y^a$ in the number of q+1 are each independently a hydrogen atom, an optionally protected hydroxyl group, a halogen atom or an organic group that crosslinks to the 4-position carbon atom, and q is any integer of one or more.

As the hydroxyl-protecting group for $P^{1a}$, those similar to the above-mentioned hydroxyl-protecting group for $P^1$ exemplified above can be used. It is preferably a dimethoxytrityl group.

As the phosphoric acid-protecting group for $P^{2a}$, those similar to the above-mentioned phosphoric acid-protecting group for $P^2$ exemplified above can be used. It is preferably a group represented by —$CH_2CH_2$WG (WG is an electron-withdrawing group), and WG is preferably a cyano group.

$R^{40a}$ are preferably the same and each is an oxygen atom or a sulfur atom.

As the optionally protected hydroxyl-protecting group for $Y^a$, those similar to the above-mentioned hydroxyl-protecting group for Y exemplified above can be used. It is preferably a tert-butyldimethylsilyl group.

As the "organic group that crosslinks to the 4-position carbon atom" for $Y^a$, those similar to the above-mentioned "organic group that crosslinks to the 4-position carbon atom" for Y exemplified above can be used.

As the "optionally protected nucleic acid base" for $Base^A$, those similar to the above-mentioned "optionally protected nucleic acid base" for Base and at least one of $Base^A$ present in the number of q+1 is preferably protected by a protecting group represented by the formula -L-$Y^L$—Z (as defined above), or the formula —Z' (as defined above).

The following is a scheme when step (2) is performed using compound (Ia) as a starting material.

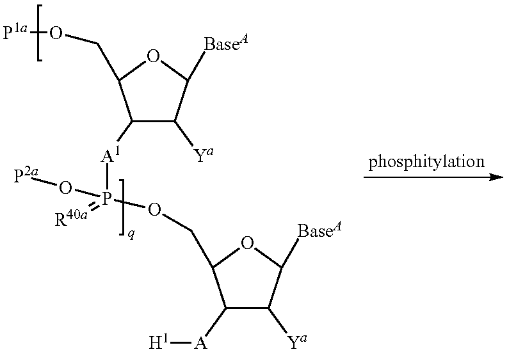

(Ia)

-continued

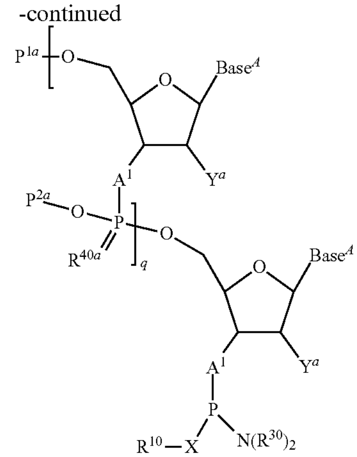

wherein each symbol is as defined above.

The "n-mer (n is any integer of two or more) oligonucleotide in which a 5'-position hydroxyl group or 5'-position phosphoric acid group is protected and a 3'-position hydroxyl group or 3'-position amino group is not protected" recited as an example of compound (Ia) used in this step may be obtained by desilylation of the 3'-terminal silyl-protecting group of the above-mentioned compound (I), preferably the above-mentioned desilylation in the present invention.

Preferable one embodiment of the "n-mer oligonucleotide (n is any integer of two or more) one of a 5'-position hydroxyl group and a 5'-position phosphoric acid group, or one of a 3'-position hydroxyl group and a 3'-position amino group is protected, and the other is not protected" is a compound having the following structure (Ia') in which a 3'-position hydroxyl group or 3'-position amino group is protected and a 5'-position hydroxyl group is not protected (hereinafter compound (Ia')).

(Ia')

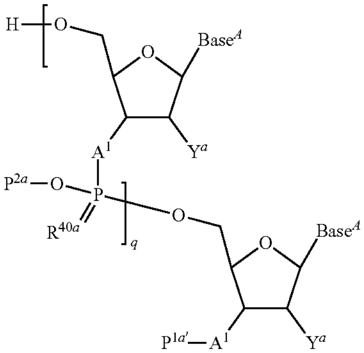

wherein $P^{1a'}$ is a hydroxyl- or amino-protecting group or a s phosphoric acid group as $-A^1-P^{1a'}$ in which one of hydroxyl groups is replaced by-OLM-OH wherein $L^{n1}$ is an organic group and hydroxyl group is protected, and each of other symbols is as defined in the formula (Ia).

As the hydroxyl-protecting group for $P^{1a'}$, those similar to the above-mentioned hydroxyl-protecting group for $P^1$ exemplified above can be used.

The amino-protecting group for $P^{1'}$ is not particularly limited and, for example, pivaloyl group, pivaloyloxymethyl group, acetyl group, trifluoroacetyl group, phenoxyacetyl group, 4-isopropylphenoxyacetyl group, 4-tert-butylphenoxyacetyl group, benzoyl group, isobutyryl group, (2-hexyl) decanoyl group, dimethylformamidinyl group, 1-(dimethylamino)ethylidene group and 9-fluorenylmethyloxycarbonyl group can be mentioned.

The following is a scheme when step (2) is performed using compound (Ia') as a starting material.

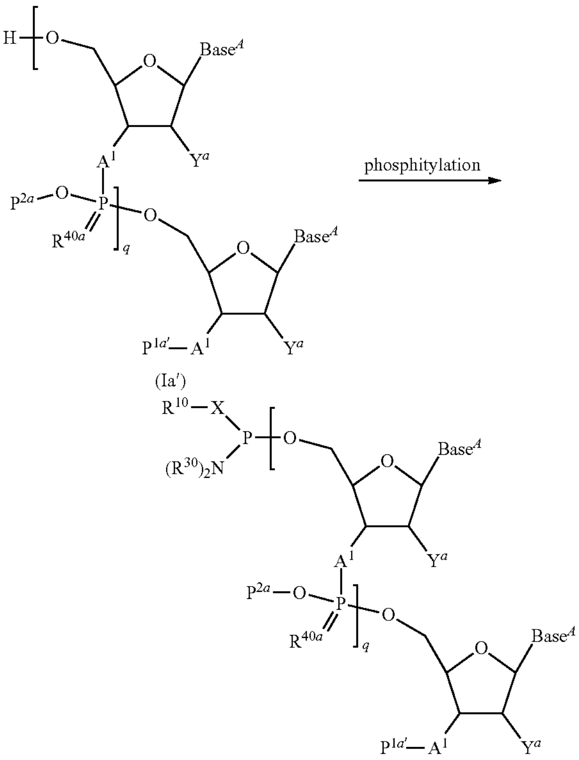

(Ia')

wherein each symbol is as defined above.

As the solvent to be used in step (2), those similar to the solvent used in step (1) can be used. Specifically, for example, toluene, dichloromethane, chloroform and the like can be mentioned. A mixed solvent of toluene and dichloromethane is preferable.

As a base to be used in step (2), a base having basicity sufficient for neutralization of an acid (activator) produced by the reaction, and free of removal of cyanoethyl on phosphoric acid or formation of a P—N bond is selected. As is such base, specifically, base with pka 5-8, preferably, collidine, N-methylmorpholine, diethylaniline and the like can be used. When a base with pka higher than 8 is used, decyanation becomes remarkable, and when a base with pka less than 5 is used, an activator regenerated as the reaction proceeds is not trapped sufficiently and a byproduct is produced.

In step (2), a phosphitylating agent precursor may not be added but is preferably added.

[Production Method of Oligonucleotide Having Functional Group On Terminal]

This method includes linking a functional group directly or via a linker to a terminal of an oligonucleotide having a phosphoramidited terminal hydroxyl group. More specifically, it includes linking a functional group directly or via a linker to a 3'-terminal of a 3'-terminal phosphoramidited oligonucleotide, or linking a functional group directly or via a linker to a 5'-terminal of a 5'-terminal phosphoramidited oligonucleotide. The "3'-terminal phosphoramidited oligonucleotide" and "5'-terminal phosphoramidited oligonucleotide" may be synthesized by any method. They are preferably compounds (Ia-1) and (Ia'-1) having the following structures and obtained by the above-mentioned "production method of terminal phosphoramidited oligonucleotide" of the present invention.

(Ia-1)

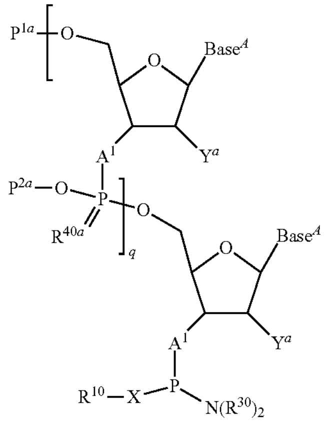

(Ia'-1)

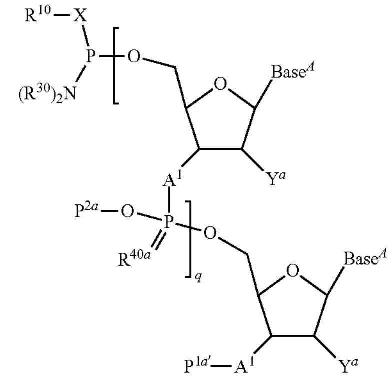

wherein each symbol is as defined above.

The following compound (Ia-2) is produced by linking a functional group to the 31-terminal of compound (Ia-1) directly or via a linker, and the following compound (Ia'-2) is produced by linking a functional group to the 5'-terminal of compound (Ia'-1) directly or via a linker, (Ia-2)

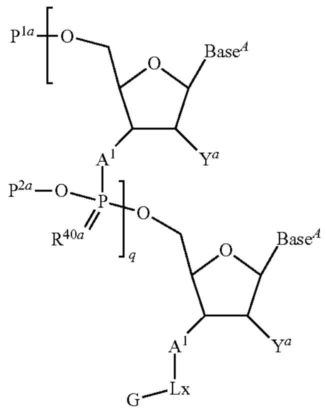

-continued (Ia'-2)

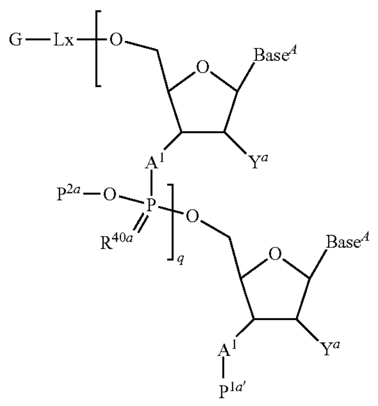

wherein Lx is a single bond or a linker. When Lx is a single bond, the functional group is directly linked to compound (Ia-1) or compound (Ia'-1). The functional group is directly linked to the 3'-terminal of compound (Ia-1) or 5'-terminal of (Ia'-1) by a hydroxyl group, a thiol group or an amino group of the functional group. When Lx is a linker, the functional group is linked to the 3'-terminal of compound (Ia-1) or 5'-terminal of (Ia'-1) via a linker (e.g., —O—, —S—, —COO—, —OCONH—, and —CONH—) having a hydroxyl group, a thiol group or an amino group as a reaction point.

In the formula, G is a functional group and, for example, one derived from at least one kind selected from the group consisting of oligonucleotide, mononucleoside, cholesterol, GalNac3, PEG, low molecule medicament, biotin, peptide and a labeled compound can be mentioned. Preferred are oligonucleotide and mononucleoside, more preferred is oligonucleotide.

For example, when the functional group is an n'-mer (n' is any integer of two or more) oligonucleotide having the following structure (Ib):

(Ib)

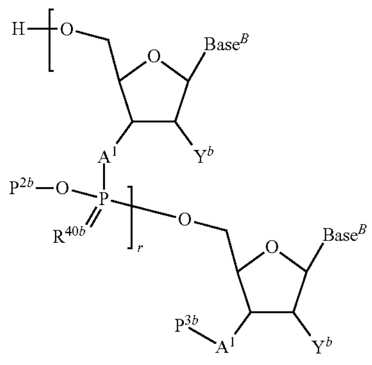

wherein $A^1$ in the number of r+1 are each independently an oxygen atom or NH, $Base^B$ in the number of r+1 are each independently an optionally is protected nucleic acid base, $P^{2b}$ in the number of r are each a phosphoric acid-protecting group, $R^{40b}$ in the number of r are each an oxygen atom or a sulfur atom, $P^{1b}$ is a hydroxyl- or amino-protecting group or a phosphoric acid group as $-A^1P^{3b}$ in which one of hydroxyl groups is replaced by $—OL^{n1}$-OH wherein $L^{n1}$ is an organic group and hydroxyl group is protected, $Y^b$ in the number of r+1 are each a hydrogen atom, an optionally protected hydroxyl group, halogen atom, or an organic group that crosslink to the tion carbon atom, and r is any integer of one or more, in which a 3'-position hydroxyl group or 3' position amino group or 3' phosphoric acid group is protected and a 5'-hydroxyl group is not protected, the present method corresponds to fragment condensation of oligonucleotide and specifically include the following step:

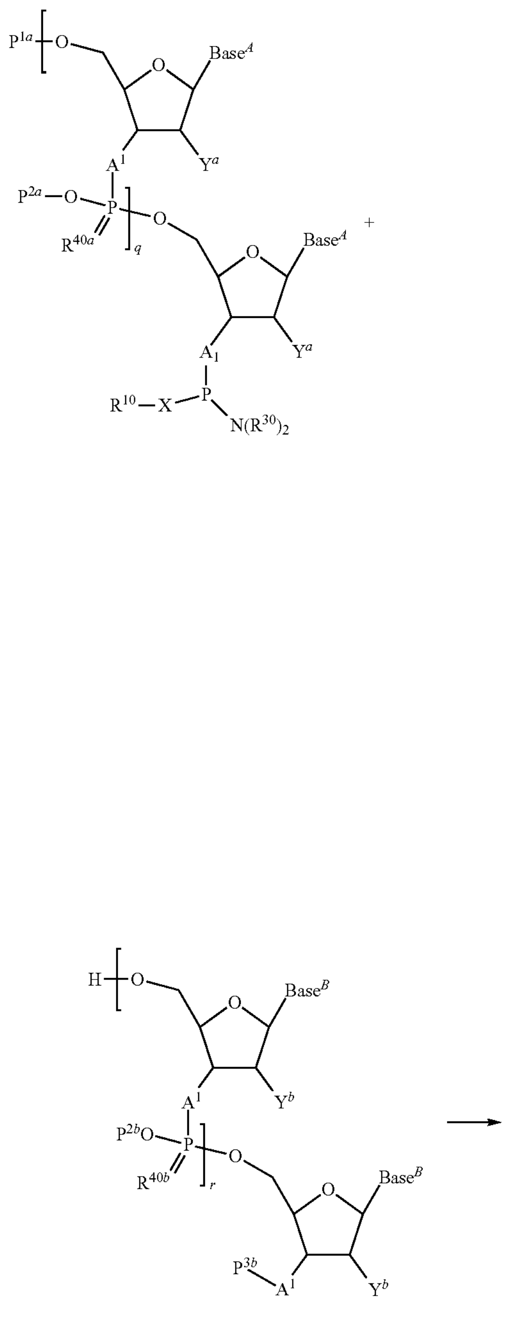

-continued

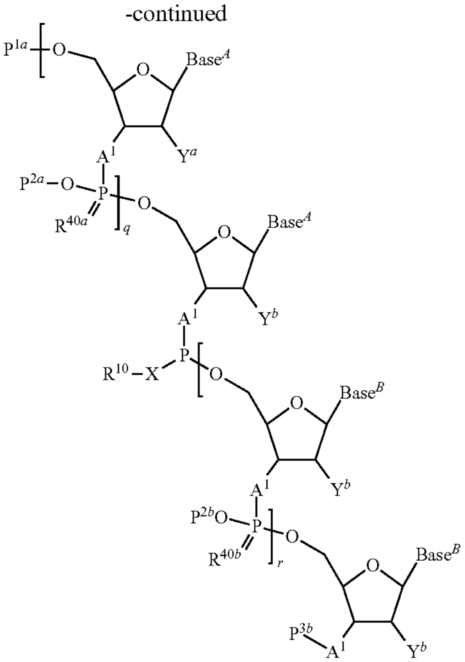

For example, when the functional group is an n'-mer (n' is any integer of two or more) oligonucleotide having the following structure (Ib'):

(Ib')

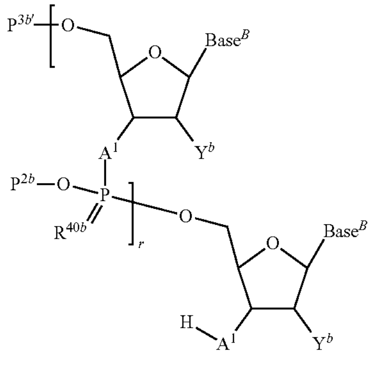

wherein $P^{3b}$ is a hydroxyl-protecting group or a phosphoric acid as $—O—P^{3b'}$ group in which one of hydroxyl groups is replaced by $—OL^{n1}$-OH wherein $L^{n1}$ is an organic group and hydroxyl group is protected, and each symbol is as defined for the formula (Ib), in which a 5'-position hydroxyl group or 5'-position phosphoric acid group is protected and a 3'-position hydroxyl group or 3'-position amino group is not protected, the present method corresponds to fragment condensation of oligonucleotide and specifically include the following step:

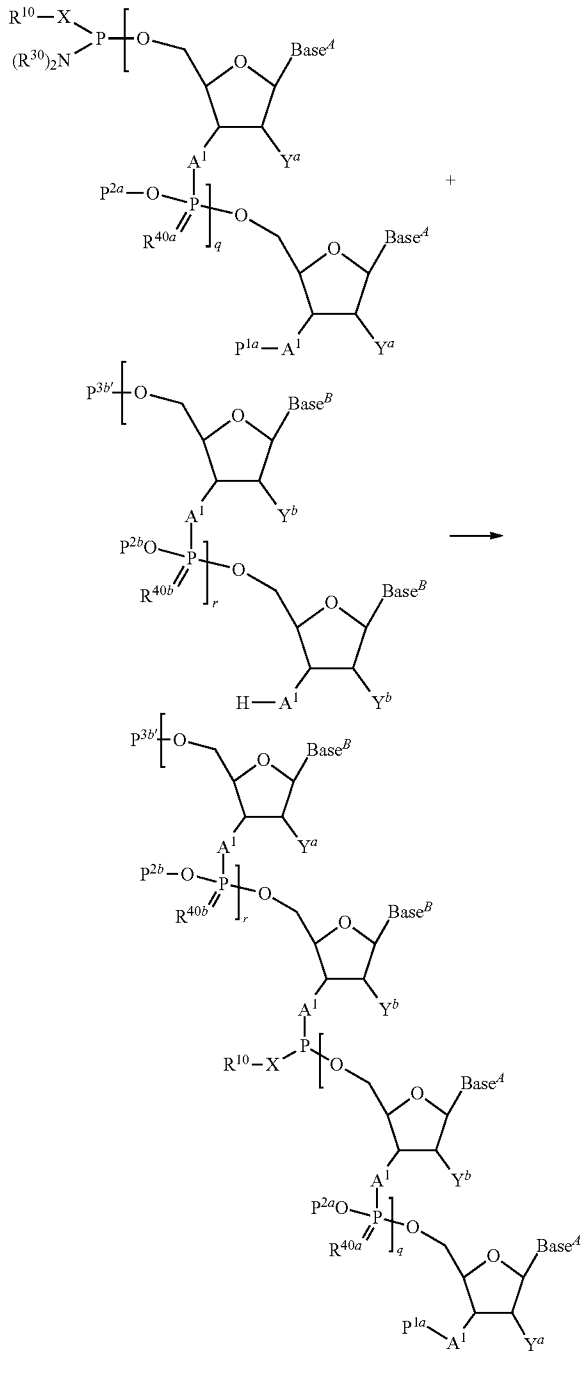

wherein each symbol is as defined above.

As the "optionally protected nucleic acid base" for Base ", s those similar to the above-mentioned "optionally protected nucleic acid base" for Base and at least one of Base" present in the number of r+1 is preferably protected by a protecting group represented by the formula -L-$Y^L$—Z (as defined above), or the formula-z' (as defined above), The phosphoric acid-protecting group for $P^{2b}$ is not particularly limited as long as it can be deprotected under basic conditions and can be used as a phosphoric acid-protecting group, and a group represented by —$CH_2CH_2WG$ (WG is an electron-withdrawing group) is preferable, and WG is preferably a cyano group.

$R^{40b}$ are preferably the same and each is an oxygen atom or a sulfur atom.

The optionally protected hydroxyl-protecting group for $Y^b$ is not particularly limited, and those exemplified in the definition of Y can be used similarly.

As the "organic group that crosslinks to the 4-position carbon atom" for $Y^b$, those exemplified in the definition of Y can be used similarly.

The hydroxyl-protecting group for $P^{3b'}$ is not particularly limited as long as it is stable under acidic conditions capable of removing the 5'-terminal hydroxyl-protecting group (in the case of compound (Ib)) or 3'-position hydroxyl-protecting group (in the case of compound (Ib') of oligonucleotide obtained after linking and can dissolve n'-mer oligonucleotide (compound (Ib) or compound (Ib')) in a reaction solvent so that the reaction will proceed in a condensation reaction. A protecting group represented by the formula -L-$Y^L$—Z (each symbol is as defined above) or the formula —Z' (as defined above) can be used. Preferably, L is a succinyl group. As the hydroxyl-protecting group for $P^{3b'}$, those similar to the description in the above-mentioned desilylation section can also be used, and preferred is a dimethoxytrityl group.

The n'-mer oligonucleotide (1b') having -L-$Y^L$—Z as $P^{3b'}$ can be prepared by repetitively linking a monomer nucleoside having a protected hydroxyl group at the 3'-position and phosphoramidite at the 5'-position to a mononucleoside having-L-$Y^L$—Z at the 5'-position and a hydroxyl group at the 3'-position by a phosphoramidite method in a liquid phase in the same manner as described in WO 2012157723A1. The monomer nucleoside can be prepared based on a known document (e.g.) Wagner, T.; Pfleiderer, W. Nucleoside Nucleotides 1997, 16, 1657-1660; U.S. Pat. No. 8,541,569B2).

Preferable one embodiment of the present invention is a method for producing an oligonucleotide having a functional group at the 3'-terminal and represented by the following formula (II);

(II)

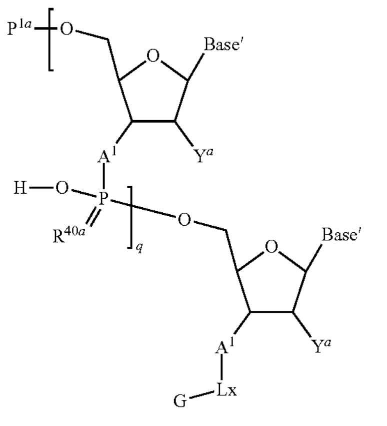

wherein

Lx is a single bond or linker,

G is a functional group,

Base' in the number of q+1 are each an unprotected nucleic acid base, and other symbols are as defined above, the method comprising a step of linking, directly or via a linker, a functional group to a 3'-terminal of a 3'-terminal phosphoramidited oligonucleotide represented by the following formula (Ia-1'):

(Ia-1')

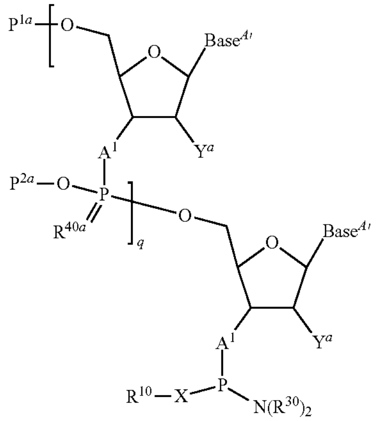

wherein

Base$^{A'}$ in the number of q+1 are each independently a nucleic acid base optionally protected by a protecting group represented by the formula: -L'-Y'—Z (L' is succinyl group, $Y^L$ and Z are as defined above) or a protecting group represented by the formula: —Z' (as defined above), and each of other symbols is as defined above, to give an oligonucleotide having a functional group at a 3-terminal and represented by the following formula (Ia-2');

(Ia-2')

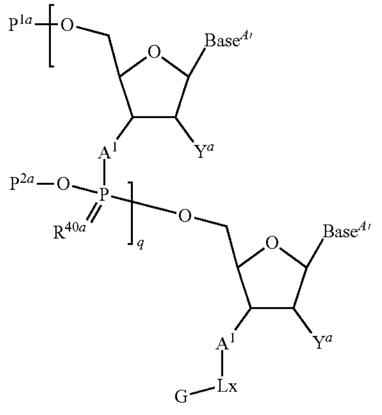

wherein each symbol is as defined above, and removing the protecting group.

[Production Method of the Present Invention]

The production method of oligonucleotide by using the method of the present invention (hereinafter to be also referred to as the "production method of the present invention") is now explained.

The present invention is a production method of oligonucleotide, containing the following steps (1) and (2):

(1) a step of condensing an n-mer oligonucleotide in which the 3'-hydroxyl group is phosphoramidited and the 5'-hydroxyl group is protected and an n'-mer oligonucleotide in which the 3'-hydroxyl group is protected and the 5'-hydroxyl group is not protected by forming a phosphite triester bond via the 5'-hydroxyl group thereof, and (2) a step of converting the phosphite triester bond of the n+n'-mer oligonucleotide obtained in step (1) to a phosphate triester bond or a thiophosphate triester bond by adding an oxidant or a sulfurizing agent to the reaction mixture of step (1).

Each step is explained in detail in the following.

Step (1) (Condensation Step)

In this step, an n-mer oligonucleotide in which the 3'-hydroxyl group is phosphoramidited and the 5'-hydroxyl group is protected and an n'-mer oligonucleotide in which the 3'-hydroxyl group is protected and the 5'-hydroxyl group is not protected are condensed by forming a phosphite triester bond via the 5'-hydroxyl group thereof.

A condensation step of an n-mer oligonucleotide in which the 3'-hydroxyl group is phosphoramidited and the 5'-hydroxyl group is protected, and an n'-mer oligonucleotide in which the 3'-hydroxyl group is protected and the 5'-hydroxyl group is not protected is generally performed in the presence of a condensation activator.

While the condensation activator to be used in this step is not particularly limited, 5-(benzylthio)-1H-tetrazole (BTT), 5-(ethylthio)-1H-tetrazole (ETT), 4,5-dicyanoimidazole (DCI), tetrazole, 5-[3,5-bis(trifluoromethyl)phenyl]-1H-tetrazole (Activator 42 (registered trade mark)), benzoimidazoletriflate (BIT), pyridine·trifluoroacetate and the like are preferably used. BTT, ETT, DCI are more preferable and BTT is particularly preferable.

The amount of the condensation activator to be used in this step is generally 0.5-10 mol, preferably 1.0-2.0 mol, particularly preferably 1.0 mol, per 1 mol of phosphoramidited oligonucleotide.

While the reaction temperature in this step is not particularly limited as long as the reaction proceeds, it is preferably 0 to 100° C., more preferably 20 to 50° C., particularly preferably 20 to 30° C. While the reaction time varies depending on the kind of the oligonucleotide to be used, the kind of solvent, the reaction temperature and the like, it is 30 min to 24 hr.

This step is performed in a solvent that does not influence the reaction. Specifically, pyridine, THF, dichloromethane, chloroform, toluene, acetonitrile or a mixed solvent of any of these can be mentioned.

The amount of use of n-mer oligonucleotide in which the 3'-hydroxyl group is phosphoramidited and the 5'-hydroxyl group is protected and the amount of use of n'-mer oligonucleotide in which the 3'-hydroxyl group is protected and the 5'-hydroxyl group is not protected depend on which substrate is intended to be closer to more complete consumption. It is preferably 0.1-10 mol, more preferably 0.5-3 mol, particularly preferably 1.0-2.0 mol, of the former per 1 mol of the latter.

Step (2) (Oxidation Step or Sulfurization Step)

The n+n'-mer oligonucleotide obtained in step (1) is reacted with an oxidant or sulfurizing agent to convert the phosphite triester bond in the n+n'-mer oligonucleotide to a phosphate triester bond or a thiophosphate triester bond.

This step can be simply performed by directly adding an oxidant or sulfurizing agent to the reaction mixture after step (2), without isolating the n+n'-mer oligonucleotide obtained in step (1).

The "oxidant" to be used in this step is not particularly limited as long as it has an ability to oxidize a phosphite triester bond into a phosphate triester bond without oxidizing other moiety, iodine, (1S)-(+)-(10-camphanylsulfonyl) oxaziridine, tert-butyl hydroperoxide (TBHP), 2-butanone peroxide, 1,1-dihydroperoxycyclododecane, bis(trimethylsilyl) peroxide and m-chloroperbenzoic acid are preferably used. To achieve a good oxidation reaction, the oxidant is preferably iodine, (1S)-(+)-(10-camphanylsulfonyl) oxaziridine, tert-butyl hydroperoxide, 2-butanone peroxide or 1,1-dihydroperoxycyclododecane, more preferably iodine, (1S)-(+)-(10-camphanylsulfonyl) oxaziridine, tert-butyl hydroperoxide or 2-butanone peroxide, further preferably iodine or tert-butyl hydroperoxide, particularly preferably iodine. Such oxidant can be used by diluting with a suitable solvent at a concentration of 0.05-2 M. Such diluent solvent is not particularly limited as long as it is inert to the reaction and pyridine, THF, dichloromethane, water, and a mixed solvent of any of these can be mentioned. Of these, for example, iodine/water/pyridine-THF or iodine/pyridine-acetic acid, or peroxidative agent (TBHP)/dichloromethane is preferably used.

The "sulfurizing agent" to be used in this step is not particularly limited as long as it has an ability to convert a phosphite triester bond to a thiophosphate triester bond, and 3-((N,N-dimethylaminomethylidene)amino)-3H-1,2,4-dithiazole-5-thione (DDTT), 3H-1,2-benzodithiol-3-one-1,1-dioxide (Beaucage reagent), 3H-1,2-benzodithiol-3-one, phenylacetyl disulfide (PADS), tetraethylthiuram disulfide (TETD), 3-amino-1,2,4-dithiazole-5-thione (ADTT) and sulfur are preferably used. Since a good reaction proceeds, 3-((N,N-dimethylaminomethylidene)amino)-3H-1,2,4-dithiazole-5-thione (DDTT), 3H-1,2-benzodithiol-3-one-1,1-dioxide (Beaucage reagent), 3H-1,2-benzodithiol-3-one, and phenylacetyl disulfide (PADS) are more preferable, 3-((N,N-dimethylaminomethylidene)amino)-3H-1,2,4-dithiazole-5-thione and 3H-1,2-benzodithiol-3-one-1,1-dioxide are further preferable, and 5-((N,N-dimethylaminomethylidene)amino)-3H-1,2,4-dithiazole-5-thione is particularly preferable. Such sulfurizing agent can be used by diluting with a suitable solvent at a concentration of 0.05-2 M. Such diluent solvent is not particularly limited as long as it is inert to the reaction and, for example, dichloromethane, acetonitrile, pyridine or a mixed solvent of any of these can be mentioned.

The amount of the oxidant or sulfurizing agent to be used is 1 to 50 mol, preferably 1 to 5 mol, per 1 mol of the n+n'-mer oligonucleotide (iv) obtained in step (1).

The reaction temperature is not particularly limited as long as the reaction proceeds, and 0° C.-100° C. is preferable, 20° C.-50° C. is more preferable. The reaction time varies depending on the kind of n+n'-mer oligonucleotide (iv), the kind of the oxidant or sulfurizing agent to be used, reaction temperature and the like and is 1 min-3 hr.

Furthermore, by including the following step (3) when desired, n+n'-mer oligonucleotide can be purified conveniently and effectively by removing excess starting materials and by-products:

(3) a step of adding a polar solvent to the reaction mixture obtained in step (2) to precipitate the n+n'-mer oligonucleotide and obtaining same by solid-liquid separation.

Oligonucleotide can be isolated and produced by further including step (4) in the production method of the present invention:

(4) a step of removing all the protecting groups of the n+n'-mer oligonucleotide obtained in step (3).

Step (3) (Precipitation and Solid-Liquid Separation Step)

In this step, a polar solvent is added to a reaction mixture containing n+n'-mer oligonucleotide having a phosphate triester bond or a thiophosphate triester bond, which is obtained in step (2), to allow precipitation of the n+n'-mer oligonucleotide, and the precipitate is obtained by solid-liquid separation.

Examples of the polar solvent used to precipitate the object product (n+n'-mer oligonucleotide) in this step include alcohol solvents such as methanol, ethanol, isopropanol and the like, nitrile solvents such as acetonitrile, propionitrile and the like, amide solvents such as dimethylformamide, dimethylacetamide and the like, dimethylsulfoxide, water etc., and mixed solvent of two or more kinds thereof. Among them, alcohol solvents and nitrile solvents are preferably used, and methanol and acetonitrile are more preferably used. The polar solvent in the present invention is preferably acetonitrile from the practical aspects.

In precipitation where iodine is used as an oxidant, the color development due to iodine can be removed by using a solution of methanol, which is a precipitation solvent, saturated with sodium thiosulfate (hypo), and therefore, n+n'-mer oligonucleotide wherein the 5'-hydroxyl group is protected can be isolated with high purity.

In precipitation where a sulfurizing agent is used, n+n'-mer oligonucleotide wherein the 5'-hydroxyl group is protected can be isolated with high purity by using a solution of methanol, which is a precipitation solvent, saturated with a reducing agent such as a trivalent phosphite reagent (e.g., trimethylphosphite, triethylphosphite, tris(2-carboxyethyl) phosphine etc.), hypo and the like.

The production method of oligonucleotide of the present invention can afford the object oligonucleotide with high purity and in a high yield by repeating the above-mentioned steps (1) to (3) a desired number of times.

Step (4) (Deprotection, Oligonucleotide Isolation Step)

In the production method of oligonucleotide of the present invention, deprotection is performed after step (3) according to the kind and properties of the protecting group, whereby oligonucleotide is isolated. As a deprotection method, for example, all protecting groups of the oligonucleotide can be removed according to the deprotection method described in Greene's PROTECTIVE GROUPS IN ORGANIC SYNTHESIS, 4th ed., JOHN WILLY&SONS (2006) and the like. To be specific, phenoxyacetyl group, acetyl group and the like, all of which are protecting groups of nucleic acid base; and cyanoethyl group and the like binding to a phosphoric acid group can all be removed by a treatment with aqueous ammonia/ethanol solution.

Oligonucleotide without a protecting group is easily degraded by an enzyme, and therefore, oligonucleotide is preferably isolated under control of air cleanliness.

The progress of the reaction in each of the above-mentioned steps can be confirmed by a method similar to conventional liquid phase organic synthesis reaction. That is, the reaction can be traced by thin layer silica gel chromatography, high performance liquid chromatography or the like.

The oligonucleotide obtained in step (3) or step (4) can also be led to a desired oligonucleotide derivative by further applying an organic synthesis reaction.

The oligonucleotide obtained in step (4) can provide RNA, DNA, oligonucleic acid medicaments.

In addition, when the functional group is an n'-mer (n' is any integer of two or more) oligonucleotide having the following structure (Ib'), in which the 5'-position hydroxyl group or 5'-position phosphoric acid group is protected and the 3'-position hydroxyl group or 3'-position amino group is not protected, it can also be performed similarly.

(Ib')

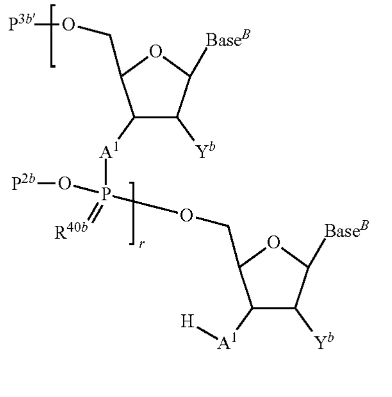

wherein each symbol is as defined above.

EXAMPLES

The present invention is explained in detail in the following by referring to Preparation Examples and Examples, which are not to be construed as limiting the scope of the present invention. The reagents, apparatuses and materials used in the present invention are commercially available unless otherwise specified. In the present specification, when indicated by abbreviation, each indication is based on the abbreviation of the IUPAC-IUB Commission on Biochemical Nomenclature or conventional name in the art.

The yields in the following Preparation Examples and Examples are in mol/mol %. Unless particularly defined, "%" in the present specification shows "mass %". In addition, the ratio of the solvents in the following Preparation Examples and Examples are in volume ratio. 1H-NMR spectrum was obtained using tetramethylsilane as the internal standard and $CDCl_3$ as the measurement solvent. NMR spectrum was measured using Bruker AVANCE 400 (400 MHZ) nuclear magnetic resonance apparatus.

Electron Spray Ionization liquid chromatography/mass spectrometry (hereinafter to be abbreviated as LC/MS) was measured using Agilent Technologies 1290 Infinity.

The abbreviations used in the following Preparation Examples and Examples are as described below. When the nucleic acid base of nucleoside is protected, the protecting group is indicated with a superscript after each nucleoside.

dT: 2'-deoxythymidine
dC: 2'-deoxycytidine
dG: 2'-deoxyguanosine
dA: 2'-deoxyadenosine
DMTr: 4, 4'-dimethoxytrityl
Ac: acetyl
Bz: benzoyl
dma: dimethylaminoethylidene
iBu: isobutyryl
PA: (2-cyanoethyl)-N,N-diisopropylphosphoramidite
TBDMS: tert-butyldimethylsilyl
DIPPS: diisopropylphenylsilyl
HD: hexyldecanoyl
IPODIPS: isopropoxydiisopropylsilyl
TOB: 3,4,5-tris(octadecyloxy)benzyl
CO-TOP: 3,4,5-tris(octadecyloxy)benzoyl
suc: succinate
TEA: triethylamine

Example 1: Synthesis of $N^4$-[3,4,5-tris(octadecyloxy)benzoyl]-3'-O-(tert-butyldimethylsilyl)-5'-O-(4,4'-dimethoxytrityl)deoxycytidine (DMTr-$dC^{CO-TOP}$-TBDMS)

(1) Synthesis of 5'-O-(4,4'-dimethoxytrityl)-3'-O-(tert-butyldimethylsilyl)deoxycytidine

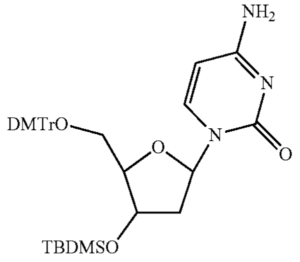

Under an argon atmosphere, 5'-O-(4,4'-dimethoxytrityl) deoxycytidine (6.32 g, 11.9 mmol) was dissolved in dry N,N-dimethylformamide (24.0 mL), imidazole (2.47 g, 36.4 mmol), tert-butyldimethylsilyl chloride (2.71 g, 18.0 mmol) were added and the mixture was stirred at 35° C. for 12 hr. Completion of the reaction was confirmed by thin layer chromatography and the reaction mixture was extracted with dichloromethane (20 mL) and 5% aqueous sodium hydrogen carbonate solution (10 mL), washed with water (20 mL) and then saturated brine (20 mL). The organic layer was dried over sodium sulfate and the solvent was evaporated under reduced pressure. The obtained crude product was purified by silica gel column chromatography (eluate: 1% triethylamine-containing n-hexane:ethyl acetate=1:1→0:1 successively 1% triethylamine-containing dichloromethane:methanol=10:1→5:1) to give the title compound (6.81 g, 10.5 mmol, 88.9%).

$^1H$ NMR (400 MHz, $CDCl_3$) δ: −0.07 (s, 3H, $SiCH_3$), −0.01 (s, 3H, $SiCH_3$), 0.80 (s, 9H, $^tBu$), 1.81 (m, 2H, 4-$NH_2$), 2.19 (ddd, J=4.8, 6.4, 13.2 Hz, 1H, 2'-CHH), 2.47 (ddd, J=6.4, 6.8, 13.2 Hz, 2'-CHH), 3.29 (dd, J=10.8, 2.8 Hz, 1H, 5'-CHH), 3.53 (dd, J=10.8, 2.8 Hz, 1H, 5'-CHH), 3.80 (s, 6H, OCH, of DMTr), 3.94 (ddd, J=2.8, 2.8, 6.4 Hz, 1H, 4'-CH), 4.60 (dd, J=6.4, 6.4, 6.4 Hz, 1H, 3'-H), 5.38 (d, J=7.2 Hz, 5-H), 6.26 (da, J=6.8, 4.8 Hz, 1H, 1'-H), 6.84 (d, J=8.8 Hz, 4H, 2, 2', 6, 6'-H of DMTr), 7.2-7.4 (m, 8H, Ar and 5-H of cytidine), 7.40 (d, J=8.4 Hz, 2H, 2, 6-H of Ph), 8.0-8.2 (m, 2H, —$NH_2$).

(2) Synthesis of N[4]-[3,4,5-tris(octadecyloxy)benzoyl]-3'-O-(tert-butyldimethylsilyl)-5'-O-(4,4'-dimethoxytrityl)deoxycytidine (DMTr-dC$^{CO\text{-}TOP}$-TBDMS)

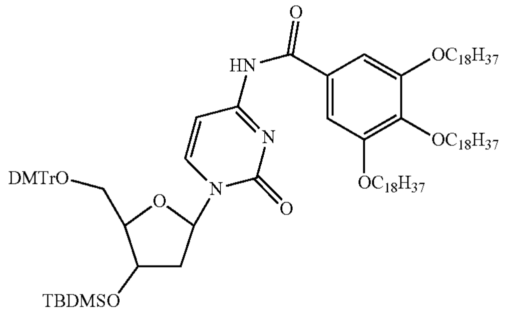

3,4,5-tris(octadecyloxy)benzoic acid (0.927 g, 1.00 mmol), diisopropylethylamine (0.520 mL, 2.04 mmol) were dissolved in chloroform (10.0 mb), 2-(1H-benzotriazol-1-yl)-1,1,3,3-tetramethyluroniumhexafluorophosphate (HBTU) (0.573 g, 1.51 mmol) was added at 0° C., and the mixture was warmed to room temperature and stirred for 40 min. To the reaction mixture was added 5'-O-(4,4'-dimethoxytrityl)-3'-O-(tert-butyldimethylsilyl) deoxycytidine (0.969 g, 1.50 mmol) obtained in (1) and the mixture was stirred at 40° C. for 21 hr. Completion of the reaction was confirmed by thin layer chromatography, and the mixture was cooled to room temperature, acetonitrile (50 mL) was added and the object product was precipitated and filtered using a hirsch funnel, and washed. White precipitate on the filter paper was dispersed in acetonitrile (40 mL), filtered again using a hirsch funnel, washed and dried in vacuo to give the object DMTr-dC$^{CO\text{-}TOP}$-TBDMS (1.51 g, 0.973 mmol, 97.3%).

$^1$H NMR (400 MHZ, $CDCl_3$) δ: −0.04 (s, 3H, $Si(CH_3)(CH_3)$), 0.02 (s, 3H, $Si(CH_3)(CH_3)$), 0.82 (s, 9H, $^t$Bu), 0.89 (t, J=6.8 Hz, 9H, $O(CH_2)_{17}CH_3$), 1.20-1.50 (m, 90H, $OCH_2CH_2(CH_2)_{15}CH_3$), 1.75 (quint, J=6.8 Hz, 2H, 4-$OCH_2CH_2(CH)_2CH_3$), 1.83 (quint, J=6.8 Hz, 4H, 3,5-$OCH_2CH_2(CH)_{15}CH_3$), 2.22 (ddd, J=13.6, 6.0, 4.8 Hz, 1H, 2'-CHH), 2.585 (ddd, J=13.6, 6.4, 6.4 Hz, 1H, 2'-CHH), 3.34 (dd, J=10.8, 3.6 Hz, 1H, 5'-CHH), 3.53 (dd, J=10.8, 2.8 Hz, 1H, 5'-CHH), 3.806 (s, 3H, DMTr 4-$OCH_3$), 3.809 (s, 3H, DMTr 4'-$OCH_3$), 3.99-4.04 (m, 7H, 3'-H and $OCH_2(CH_2)_{16}CH_3$), 4.46 (ddd, J=6.4, 6.0, 6.0, 1H, 3'-H), 6.27 (dd, J=6.4, 4.8 Hz, 1H, 1'-H), 6.68 (d, J=8.8 Hz, 4H, 3,3',4,4'-H of p-methoxyphenyl), 7.05 (brs, 2H, 2,6-H of 3,4,5-tris(octadecyloxy)benzoyl), 7.27-7.33 (m, 8H, 2,2',6, 6'-H of p-methoxyphenyl, 3,4,5-H of phenyl and 6-H of cytosine), 7.40 (d, J=7.2 Hz, 2H, 2,6-H of phenyl), 8.40 (d, J=7.2 Hz, 1H, 5-H of cytosine), 8.53 (s, 1H, cytosine N—H).

Example 2: Synthesis of 5'-O-(4,4'-dimethoxytrityl)-deoxythymidine 3'-[O-(2-cyanoethyl)]phosphorothionyl-N[2]-isobutyryldeoxyguanosine 3'-[O-(2-cyanoethyl)]phosphorothionyl-N[4]-[3,4,5-tris(octadecyloxy)benzoyl]-3'-tert-butyldimethylsilyldeoxycytidine (DMTr-d[TG$^{iBu}$C$^{CO\text{-}TOP}$]-TBDMS)

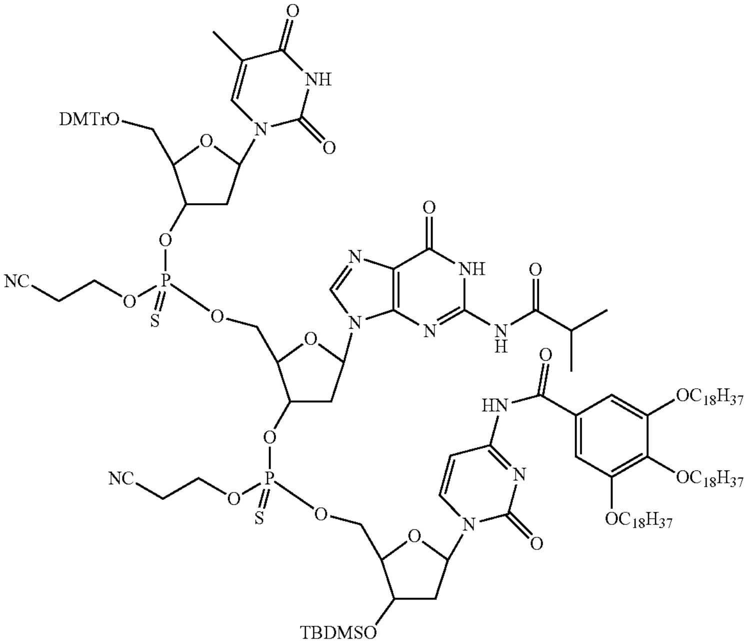

(1) Synthesis of 5'-O-(4,4'-dimethoxytrityl)-N[2]-isobutyryldeoxyguanosine 3'-[O-(2-cyanoethyl)] phosphorothionyl-N[4]-[3,4,5-tris(octadecyloxy)benzoyl]-3'-tert-butyldimethylsilyldeoxycytidine (DMTr-d[G$^{iBu}$C$^{CO\text{-}TOP}$]-TBDMS)

DMTr-dC$^{CO\text{-}TOP}$-TBDMS (0.777 g, 0.500 mmol) obtained in Example 1 and 5-methoxyindole (10.0 mmol) were dissolved in dehydrated dichloromethane (23.0 mL). Trifluoroacetic acid (55.7 μL, 0.75 mL) was added dropwise thereto, the mixture was stirred at room temperature for 30 min, and completion of the reaction was confirmed by UPLC. The reaction mixture was neutralized with 2,4,6,- trimethylpyridine, a solution of 5'-O-(4,4'-dimethoxytrityl)-$N^2$-isobutyryldeoxyguanosine-3'-[O-(2-is cyanoethyl) (N,N-diisopropyl)]phosphoramidite (1.68 g, 2.00 mmol), 5-(benzylthio)-1H-tetrazole (0.384 g, 2.00 mmol) in acetonitrile (3.00 mL) was added, and the mixture was stirred at room temperature for 2 hr. 3-[(N,N-dimethylaminomethylidene)amino]-3H-1,2,4-dithiazole-5-thione (0.452 g, 2.20 mmol) was added, and the mixture was stirred at room temperature for 45 min to sulfurate_phosphite intermediate. Acetonitrile (120 mL) was added at room temperature to precipitate the object compound. The reaction mixture was filtered using a hirsch funnel, washed with acetonitrile and dried in vacuo to give the object DMTr-d[$G^{iBu}C^{CO-TOP}$]-TBDMS (0.970 g, 0.480 mmol, 96.0%) as a white solid.

The sample was dissolved in tetrahydrofuran, the cyanoethyl-protecting group on phosphoric acid was made to fall off with DBU, and the object product was identified by LC/MS. LC/MS m/z: calcd 1966.23, found 1966.24 $[M-H]^-$.

(2) Synthesis of 5'-O-(4,4'-dimethoxytrityl)-deoxythymidine 3'-[O-(2-cyanoethyl)]phosphorothionyl-$N^2$-isobutyryl-deoxyguanosine 3'-[O-(2-cyanoethyl)] phosphorothionyl $N^4$-[3,4,5-tris(octadecyloxy) benzoyl]-3'-tert-butyldimethylsilyldeoxycytidine (DMTr-d[$TG^{iBU}C^{CO-TOP}$]-TBDMS)

Under an argon atmosphere, DMTr-d[$G^{iBu}C^{CO-TOP}$]-TBDMS (950 mg, 0.470 mmol) obtained in (1) was dissolved in dehydrated dichloromethane (23 mL), 5-methoxyindole (1.38 g, 9.40 mmol), trifluoroacetic acid (41.9 μL, 0.564 mmol) were added, the mixture was stirred at room temperature for 30 min, and completion of the reaction was confirmed by LC/MS. The reaction mixture was neutralized with 2,4,6,-trimethylpyridine (1.49 μL, 1.13 mmol), a solution of 5'-O-(4,4'-dimethoxytrityl)-deoxythymidine-3'-[O-(2-cyanoethyl) (N,N-diisopropyl)]phosphoramidite (1.42 g, 1.91 mmol), 5-(benzylthio)-1H-tetrazole (0.367 g, 1.91 mmol) in acetonitrile (3.00 mL) was added, and the mixture was stirred at room temperature for 2 hr. Completion of the reaction was confirmed by LC/MS, after which 3-[(N,N-dimethylaminomethylidene)amino]-3H-1,2,4-dithiazole-5-thione (0.431 g, 2.01 mmol) was added, and the mixture was stirred at room temperature for 45 min to sulfurate_phosphite intermediate. Acetonitrile (120 mL) was added at room temperature to precipitate the object compound. The reaction mixture was filtered using a hirsch funnel, washed with acetonitrile and dried in vacuo to give the object DMTr-d [$TG^{iBu}C^{CO-TOP}$]-TBDMS (1.08 g, 0.453 mmol, 96.4%) as a white solid.

The sample was dissolved in tetrahydrofuran, the cyanoethyl-protecting group on phosphoric acid was made to fall off with DBU, and the object product was identified by LC/MS. LC/MS m/z: calcd 1142.62, found 1142.63 $[M-2H]^{2-}$ Example 3: $^{31}P\{^1H\}$NMR Analysis of Cyanoethyl-Protected Form DMTr-d[$TG^{iBu}C^{CO-TOP}$]-TBDMS (ca 0.003 g) obtained in the same manner as in Example 2 was dissolved in chloroform-d (0.7 mL). $^{31}P\{^1H\}$NMR was measured and all peaks were observed in 66.4-67.2 ppm.

Example 4: Obtainment of Decyanoethylaed Specimen Using DBU

DMTr-d[$TG^{iBu}C^{CO-TOP}$]-TBDMS (0.0043 g, 0.00179 mmol) obtained in the same manner as in Example 2 was dissolved in tetrahydrofuran (0.15 mL). 1,8-Diazabicyclo [5.4.0]undec-7-ene (hereinafter DBU) (2.0 μL, 0.0133 mmol) was added and mixed. Decyanoethylation was performed at 23° C. for 5 min. To the reaction mixture was added acetonitrile (1.0 mL) and the mixture was centrifuged at 10,000 G, 4° C. for 5 min. The supernatant was removed, the remaining was dispersed in acetonitrile (1.0 mL) and similarly centrifuged again. Whole precipitate was dried in vacuo to give 0.0017 g in weight. When $^{31}P\{^1H\}$NMR ($CDCl_3$) of the resultant product was measured, all peaks appeared in 56.5-56.8 ppm, and it was confirmed that a decyanoethylated form shows $^{31}P\{^1H\}$NMR signals in a region remarkably different from that of a cyanoethyl-protected form.

Example 5: Study of Various Fluoride Ion Sources Using Desilylation (1) Study Using 3HF-TEA (DMTr-d[$TG^{iBu}C^{CO-TOP}$]-TBDMS (0.0239 g, 0.00998 mmol) obtained in the same manner as in Example 2 was dissolved in dichloromethane (0.3 mL) and cooled to 15° C. A solution of 3HF-TEA (29.0 mg, 0.180 mmol) in THF (0.60 mL) was added thereto and they were mixed. Desilylation was performed at 15° C. for 24 hr. The reaction mixture was divided into 4 by about 200 μL, acetonitrile (1.0 mL) was added to each, and the mixture was centrifuged at 10,000 G, 4° C. for 5 min. The supernatant was removed, the remaining was dispersed in acetonitrile (1.0 mL) and similarly centrifuged again. Whole precipitate was dried in vacuo to give 0.0230 g in weight. When $^{31}P\{^1H\}$NMR($CDCl_3$) of the resultant product was measured, all peaks were observed in 65.8-68.1 ppm corresponding to a cyanoethyl-protected form, and a signal in 60 ppm or below corresponding to a decyanoethylated form was not observed. In the measurement by LC-TOF MS, completion of desilylation was confirmed, and simultaneously, 0.4% of 4, 4'-dimethoxytrityl group fell off.

(2) Study of Desilylation Using 3HF-TEA-2Pyridine

DMTr-d[$TG^{iBu}C^{CO-TOP}$]-TBDMS (0.0204 g, 0.00835 mmol) obtained in the same manner as in Example 2 was dissolved in dichloromethane (0.3 mL) and cooled to 15° C. A mixed solution of 3HF-TEA (29.4 mg, 0.182 mmol), pyridine (0.065 mL, 0.360 mL) in THF (0.60 mL) was added of they were mixed. Desilylation was progressed at 15° C. for 24 hr. The reaction mixture was divided into 4 by about 200 μL, acetonitrile (1.0 mL) was added to each, and the mixture was centrifuged at 10,000 G, 4° C. for 5 min. The supernatant was removed, the remaining was dispersed in acetonitrile (1.0 mL), and similarly centrifuged again. When the whole precipitate was dried in vacuo, the weight was 0.0169 g. When $^{31}P\{^1H\}$NMR of the resultant product was measured, all peaks were observed in 65.6-68.3 ppm corresponding to a cyanoethyl-protected form, and a signal in 60 ppm or below corresponding to a decyanoethylated form was not observed. In the measurement by LC-TOF MS, completion of desilylation was confirmed.

(3) Study of Desilylation Using 3HF-TEA-4Pyridine

DMTr-d[$TG^{iBu}C^{CO-TOP}$]-TBDMS (0.719 g, 0.300 mmol) obtained in the same manner as in Example 2 was dissolved in dichloromethane (9.0 mL), and this was cooled to 15° C. A mixed solution of 3HF-TEA (870 mg, 5.44 mmol), pyridine (1.75 mL, 21.6 mmol) dissolved in THF (18 mL) was added and mixed. Desilylation was progressed at 15° C. for 24 hr. To the reaction mixture was added acetonitrile (150 mL) and the object product was precipitated, filtered using a hirsch funnel and washed with acetonitrile. The whole precipitate was dried in vacuo to give a white solid (0.652 g, 0.258 mmol, 95.2%). When $^{31}P\{^1H\}$NMR of the resultant product was measured, all peaks were observed in 65.6-68.3 ppm corresponding to a cyanoethyl-protected form, and a signal in 60 ppm or below corresponding to a decyanoethylated form was not observed. In the measurement by LC-TOF MS, completion of desilylation was confirmed.

(4) Study of Desilylation Using 3HF-TEA-2N-Methylmorpholine

DMTr-d[$TG^{iBu}C^{CO-TOP}$]-TBDMS (0.0241 g, 0.0101 mmol) obtained in the same manner as in Example 2 was dissolved in dichloromethane (0.3 mL), and this was cooled to 15° C. A mixed solution of 3HF-TEA (29.1 mg, 0.181 mmol), N-methylmorpholine (39.6 μL, 0.360 mmol) dissolved in THF (0.6 mL) was added and they were mixed. Desilylation was progressed at 15° C. for 24 hr. The reaction mixture was divided into 4 by about 200 μL, acetonitrile (1.0 mL) was added to each, and the mixture was centrifuged at 10,000 G, 4° C. for 5 min. The supernatant was removed, the remaining was dispersed in acetonitrile (1.0 mL), and similarly centrifuged again. When the whole precipitate was dried in vacuo, the weight was 0.01953 g. When $^{31}P\{^1H\}$NMR of the resultant product was measured, all peaks were observed in 65.7-68.2 ppm corresponding to a cyanoethyl-protected form, and a signal in 60 ppm or below corresponding to a decyanoethylates form was not observed. In the measurement by LC-TOF MS, completion of desilylation was confirmed.

(5) Study of Desilylation Using 3HF-TEA-2Collidine

DMTY-d[$TG^{iBu}C^{CO-TOP}$]-TBDMS (0.0240 g, 0.0100 mmol) obtained in the same manner as in Example 2 was dissolved in dichloromethane (0.3 mL), and this was cooled to 15° C. A mixed solution of 3HF-TEA (29.1 mg, 0.181 mmol), collidine (2,4,6-trimethylpyridine) (47.7 μL, 0.360 mmol) dissolved in THF (0.6 mL) was added and they were mixed. Desilylation was progressed at 15° C. for 24 hr. The reaction mixture was divided into 4 by about 200 μL, acetonitrile (1.0 mL) was added to each, and the mixture was centrifuged at 10,000 G, 4° C. for 5 min. The supernatant was removed, the remaining was dispersed in acetonitrile (1.0 mL), and similarly centrifuged again. When the whole precipitate was dried in vacuo, the weight was 0.02133 g. When $^{31}P\{^1H\}$NMR of the resultant product was measured, all peaks were observed in 65.8-68.1 ppm corresponding to a cyanoethyl-protected form, and a signal in 60 ppm or below corresponding to a decyanoethylated form was not observed. In the measurement by LC-TOF MS, completion of desilylation was confirmed.

(6) Study of Desilylation Using 3HF-TEA-2Morpholine

3HF-TEA (29.4 mg, 0.182 mmol), morpholine (31.3 μL, 0.360 mmol) were mixed in THF (0.6 mL) to give a solution containing precipitate and this was cooled to 15° C. A solution of DMTr-d[$TG^{iBu}C^{CO-TOP}$]-TBDMS (0.0236 g, 0.0099 mmol) obtained in the same manner as in Example 2 in dichloromethane (0.3 mL) was added thereto.

Desilylation was progressed at 15° C. for 72 hr. The reaction mixture was divided into 4 by about 200 μL, acetonitrile (1.0 mL) was added to each, and the mixture was centrifuged at 10,000 G, 4° C. for 5 min. The supernatant was removed, the remaining was dispersed in acetonitrile (1.0 mL), and similarly centrifuged again. When the whole precipitate was dried in vacuo, the weight was 0.0188 g. When $^{31}P\{^1H\}$NMR of the resultant product was measured, a signal in not less than 60 ppm corresponding to a cyanoethyl-protected form was not observed, only a signal in 60 ppm or below corresponding to a decyanoethylates form was observed and it was clarified that a cyanoethyl group on thiophosphoric acid completely falls off under the present conditions. In addition, completion of desilylation was also confirmed by the analysis by LC-TOF MS.

(7) Study Using HF-TEA

DMTr-d[$TG^{iBu}C^{CO-TOP}$]-TBDMS (0.0204 g, 0.00851 mmol) obtained in the same manner as in Example 2 was dissolved in dichloromethane (0.3 mL), and this was cooled to 15° C. A suspension of 3HF-TEA (29.4 mg, 0.182 mmol), triethylamine (0.0501 mL, 0.359 mL) mixed in THF (0.60 mL) was added thereto and they were mixed. Desilylation was progressed at 15° C. for 24 hr. The reaction mixture was divided into 4 by about 200 μL, acetonitrile (1.0 mL) was added to each, and the mixture was centrifuged at 10,000 G, 4° C. for 5 min. The supernatant was removed, the remaining was dispersed in acetonitrile (1.0 mL), and similarly centrifuged again. When the whole precipitate was dried in vacuo, the weight was 0.0169 g. When $^{31}P\{^1H\}$NMR of the resultant product was measured, an integration ratio of a peak of not less than 60 ppm corresponding to a cyanoethyl-protected form and a peak of 60 ppm or below corresponding to a decyanoethylated form was as follows, and it was clarified that decyanoethylation proceeds remarkably under of the present conditions. (cyanoethyl-protected thiophosphoric acid):(deprotected thiophosphoric acid)=1.00:1.66

In the measurement by LC-TOF MS, completion of desilylation was confirmed.

(8) Study Using HF-0.12Pyridine-0.88NMM

HF-pyridine (0.0162 mg; HF content 67.2%, HF 0.544 mmol, pyridine 0.0672 mmol), N-methylmorpholine (52.1 μL, 0.474 mmol) were mixed in THF (0.6 mL) to give a solution containing precipitate and this was cooled to 15° C. A solution of DMTr-d[$TG^{iBU}C^{CO-TOP}$]-TBDMS (0.0240 g, 0.0100 mmol) obtained in the same manner as in Example 2 in dichloromethane (0.3 mL) was added.

Desilylation was progressed at 15° C. for 96 hr. The reaction mixture was divided into 4 by about 200 μL, acetonitrile (1.0 mL) was added to each, and the mixture was centrifuged at 10,000 G, 4° C. for 5 min. The supernatant was removed, the remaining was dispersed in acetonitrile (1.0 mL), and similarly centrifuged again. When the whole precipitate was dried in vacuo, the weight was 0.0208 g. When $^{31}P\{^1H\}$NMR of the resultant product was measured, all peaks were observed in 65.8-68.2 ppm corresponding to a cyanoethyl-protected form, and a signal in 60 ppm or below corresponding to a decyanoethylated form was not observed. In the measurement by LC-TOF MS, completion of desilylation was confirmed.

(9) Study Using TBAF-AcOH

DMTr-d[$TG^{iBU}T^{CO-TOP}$]-TBDMS (0.0204 g, 0.00851 mmol) obtained in the same manner as in Example 2 was dissolved in dichloromethane (0.3 mL), and this was cooled to 15° C. A mixture of a solution (0.54 mL, 0.54 mmol) of 1.0 M tetrabutylammoniumfluoride in tetrahydrofuran, acetic acid (0.0309 mL, 0.536 mmol), tetrahydrofuran (0.06 mL) was added and they were mixed. Desilylation was progressed at 15° C. for 24 hr. The reaction mixture was divided into 4 by about 200 μL, acetonitrile (1.0 mL) was added to each, and the mixture was centrifuged at 10,000 G, 4° C. for 5 min. The supernatant was removed, the remaining was dispersed in acetonitrile (1.0 mL), and similarly centrifuged again. When the whole precipitate was dried in vacuo, the weight was 0.0168 g. When $^{31}P\{^1H\}$NMR of the resultant product was measured, a peak at not less than 60 ppm corresponding to a cyanoethyl-protected form was not found but only a peak at 60 ppm or below corresponding to a decyanoethylated form was observed, and it was clarified that a cyanoethyl group on thiophosphoric acid completely falls off under the present conditions. In addition, completion of desilylation was also confirmed by the analysis by LC-TOF MS.

Example 6: Synthesis of 5'-O-(4,4'-dimethoxytrityl) deoxythymidine 3'-[O-(2-cyanoethyl)]phosphorothionyl-$N^2$-isobutyryldeoxyguanosine 3'-[O-(2-cyanoethyl)]phosphorothionyl-$N^4$-[3,4,5-tris (octadecyloxy)benzoyl]deoxycytidin-3'-yl-[O-(2-cyanoethyl)]-N,N-diisopropylphosphoramidite (DMTr-d[$TG^{iBu}C^{CO\text{-}TOP}$]-PA)

(1) Synthesis of 5'-O-(4,4'-dimethoxytrityl)-deoxythymidine 3'-[O-(2-cyanoethyl)]phosphorothionyl-$N^2$-isobutyryldeoxyguanosine 3'-[O-(2-cyanoethyl)] phosphorothionyl-$N^4$-[3,4,5-tris(octadecyloxy) benzoyl]deoxycytidine (DMTr-d[$TG^{iBu}C^{CO\text{-}TOP}$]-H)

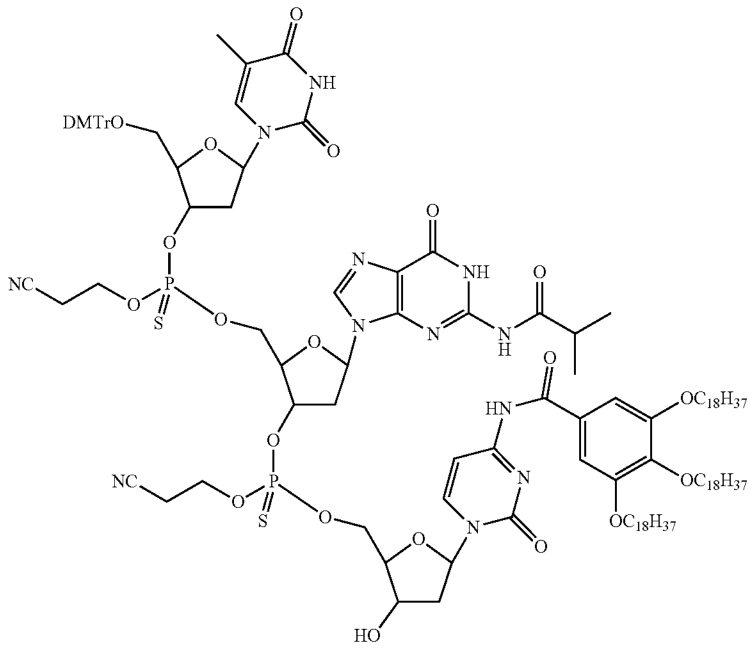

A mixture of DMTr-d[$TG^{iBu}C^{CO\text{-}TOP}$]-TBDMS obtained in the same manner as in Example 2 and 3,4,5-tris(octadecyloxy)benzylacetate was subjected to a desilylation operation in the same manner as in Example 18 to give a mixture of DMTr-d[$TG^{iBu}C^{CO\text{-}TOP}$]-H and 3,4,5-tris(octadecyloxy)benzylacetate.

The sample was dissolved in tetrahydrofuran, the cyanoethyl-protecting group on phosphoric acid was made to fall off with DBU, and the object product was identified by LC/MS. LC/MS m/z: calcd 1085.58, found 1085.59 $[M-2H]^{2-}$.

(2) Phosphitylation Using Monoimidazolidite and N-Methylmorpholine

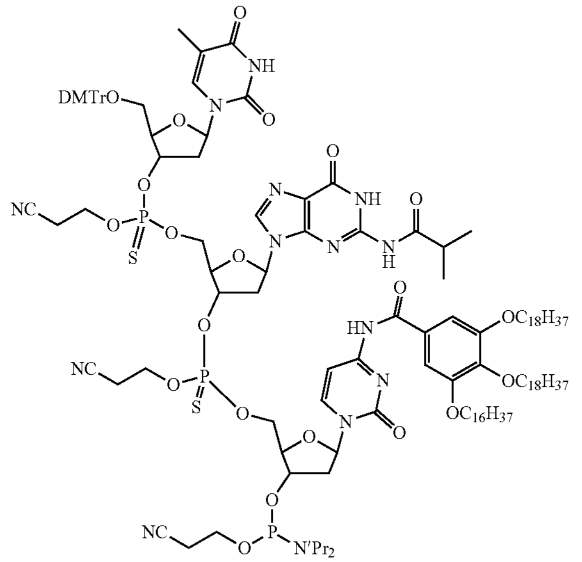

2-Cyanoethyl-N,N,N',N'-tetraisopropylphosphordiamidite (960 μL, 3.02 mmol) was dissolved in dehydrated toluene (6.6 mL), dehydrated using molecular sieve 3A powder (0.10 g) for 30 min, filtered through a 0.45 μm membrane filter and 5.25 mL thereof was dispensed into a dry screw cap bottle. To the toluene solution was added 4,5-dicyanoimidazole (0.616 g, 5.21 mmol) and the mixture was stirred for 30 min, filtered through a 0.45 μm membrane filter and the solution (1.5 mL) was separated. N-methylmorpholine (0.66 mL, 6.0 mmol, pKa=7.38) and DMTr-d[$TG^{iBu}C^{CO\text{-}TOP}$]-H (0.455 g, 0.200 mmol) obtained in (1) were added at 10° C. to give a suspension. Dehydrated dichloromethane (3.0 mL) was added at the same temperature to give a uniform solution, and the solution was stirred for 2 hr. Completion of the reaction was confirmed by LC/MS, and the reaction was discontinued with 2,4,6-trimethylpyridine. The reaction mixture was cooled to 0° C., acetonitrile (110 mL) was added, and the resultant product was precipitated. The precipitate was filtered using a hirsch funnel, washed and dried in vacuo to give DMTr-d[$TG^{iBu}C^{CO\text{-}TOP}$]-PA (0.465 g, 0.187 mmol, 93.8%). As a result of 31p NMR analysis, decyanoethylation on thiophosphoric acid was not confirmed, but H-phosphonate diester, which is considered to be caused by activation of the resultant product by dicyanoimidazole by-produced during the reaction, was detected by 5% relative to the object product. THE solution of the resultant product was decyanoethylated by DBU and the obtained sample was analyzed by LC/MS. As a result, the resultant product was detected as an oxidized form of the amidite site.

LC/MS m/z: calcd 1167.12, found 1167.12 $[M-2H]^{2-}$.

(3) Phosphitylation Using Monoimidazolidite and Collidine

Phosphitylation of 0.067 mmol of a substrate was performed using the same mixing ratio and procedures as in (2) except that the base to be added during phosphitylation was changed from N-methylmorpholine to the same equivalents of 2,4,6-trimethylpyridine. yield 92.8%. As a result of $^{31}P$ NMR analysis, decyanoethylation on thiophosphoric acid was not confirmed, but H-phosphonate diester, which is considered to be caused by activation of the resultant product by dicyanoimidazole by-produced during the reaction, was detected by 6% relative to the object product.

(4) Phosphitylation Using Monoimidazolidite and Pyridine

Phosphitylation of 0.067 mmol of a substrate was performed using the same mixing ratio and procedures as in (2) except that the base to be added during phosphitylation was changed from N-methylmorpholine to the same equivalents of pyridine (pKa=5.17). yield 92.8%. As a result of $^{31}P$ NMR analysis, decyanoethylation on thiophosphoric acid was not confirmed, but H-phosphonate diester, which is considered to be caused by activation of the resultant product by dicyanoimidazole by-produced during the reaction, was remarkably produced and the production ratio was object product:H-phosphonate diester=1:1.05

(5) Phosphitylation Using Monoimidazolidite and 1,4-Diazabicyclo[2.2.2]Octane

Phosphitylation of 0.067 mmol of a substrate was performed using the same mixing ratio and procedures as in (2) except that the base to be added during phosphitylation was changed from N-methylmorpholine to the same equivalents of 1,4-diazabicyclo[2.2.2]octane (pKa=8.82). yield 96.7%. As a result of $^{31}P$ NMR analysis, it was clarified that 86% of cyanoethyl-protecting group on thiophosphoric acid fell off. In addition, an H-phosphonate diester which is a hydrolysis form was produced by 9% relative to the object amidite.

(6) Phosphitylation Using Monoimidazolidite, Diamidite and N-Methylmorpholine

2-Cyanoethyl N,N,N',N'-tetraisopropylphosphordiamidite (1.43 mL, 4.5 mmol) was dissolved in dehydrated toluene (9.8 mL), dehydrated with a molecular sieve 3A powder (0.5 g) for 30 min, and filtered through a 0.45 μm membrane filter. To the toluene solution was added 4,5-dicyanoimidazole (0.886 g, 7.5 mmol) and the mixture was stirred for 30 min, and filtered through a 0.45 μm membrane filter to remove solids. To the reaction mixture were added at 10° C. 2-cyanoethyl N,N,N',N'-tetraisopropylphosphordiamidite (0.238 mL, 0.750 mmol), N-methylmorpholine (0.826 mL, 7.50 mmol) and DMTr-d[$TG^{iBu}C^{CO\text{-}TOP}$]-H (0.532 g, 0.233 mmol) obtained in (1) to give a suspension. Dehydrated dichloromethane (4.0 mL) was added at the same temperature to give a uniform solution, and the mixture was stirred for 2 hr. Completion of the reaction was confirmed by LC/MS, and the reaction was discontinued with 2,4,6-trimethylpyridine. The reaction mixture was cooled to 0° C., acetonitrile (110 mL) was added, and the resultant product was precipitated, filtered using a hirsch funnel, washed and dried in vacuo to give DMTr-d[$TG^{iBu}C^{CO\text{-}TOP}$]-PA (0.525 g, 0.204 mmol, 94.4%). yield amount 0.530 g (2.14 mmol, 91.6% yield). As a result of $^{31}P$ NMR analysis, decyanoethylation on thiophosphoric acid was not confirmed. A THE solution of the resultant product was decyanoethylated with DBU and in LC/MS analysis of the obtained sample, the product was detected as an oxidized form of amidite site.

LC/MS m/z: calcd 1167.12, found 1167.12 $[M-2H]^{2-}$.

Example 7: Synthesis of DMTr-d[$TG^{iBu}C^{CO\text{-}TOP}$-$A^{Bz}$TT]-suc-TOB by Condensation of DMTr-d[$TG^{iBu}C^{CO\text{-}TOP}$]-PA and HO-d[$A^{Bz}$TT]-suc-TOB molecular sieve 3A (0.229 g). The solution (4.5 mL) was filtered through a 0.45 μm membrane filter. To the filtered solution was added 5-(benzylthio)-1H-tetrazole (21.8 mg, 0.113 mmol) and the mixture was stirred at room temperature for 1 hr 30 min. Completion of condensation was confirmed by LC/MS, after which pyridine (48.5 μL, 0.600 mmol) and then 3-[(N,N-dimethylaminomethylidene)

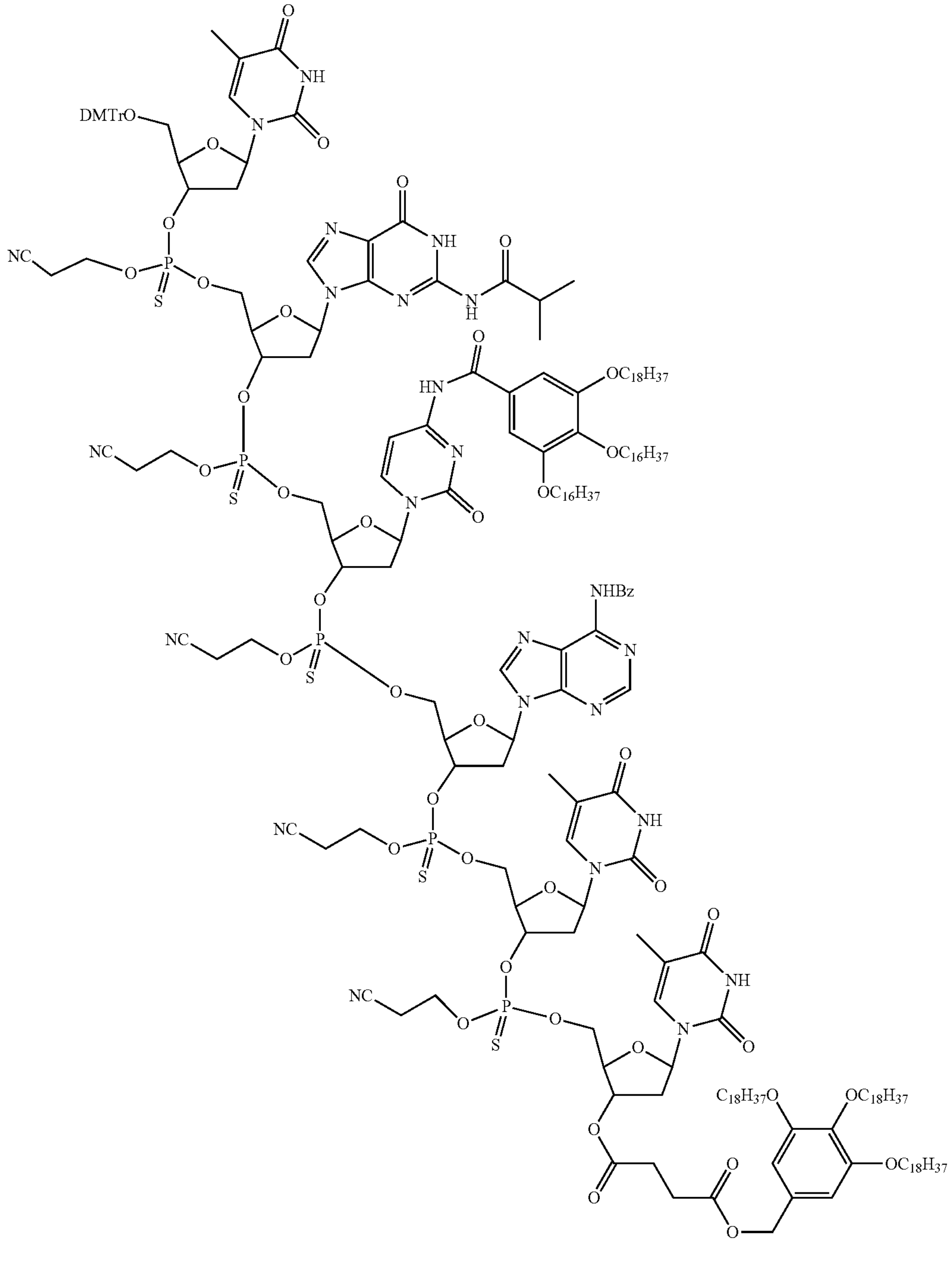

DMTr-d[$TG^{iBu}C^{CO\text{-}TOP}$]-PA (0.149 g, 0.0601 mmol) obtained in s the same manner as in Example 6-(5) and d[$A^{Bz}$TT]-suc-TOB (0.104 g, 0.0497 mmol) obtained in the same manner as in Example 1-(3) were dissolved in dichloromethane (5.0 mL), and the mixture was dehydrated by amino]-3H-1,2,4-dithiazole-5-thione (16.4 mg, 0.0799 mmol) were added, and the mixture was stirred at room temperature for 30 min to sulfuratephosphite intermediate. To the reaction mixture was added methanol (20 mL) to precipitate the object product, and the object product was filtered using a hirsch funnel and washed to give a solid (0.222 g) containing the object product.

The sample was dissolved in tetrahydrofuran, the cyanoethyl-protecting group on phosphoric acid was made to fall off with DBU, and the object product was identified by LC/MS. LC/MS m/z: calcd 1412.72, found 1412.71 $[M-2H]^{2-}$.

Example 8: Synthesis of 5'-(4,4'-dimethoxytrityl)-3'-diisopropylphenylsilyl-$N^3$-[3,4,5-tris(octadecyloxy)benzoyl]deoxythymidine (DMTr-$dT^{CO-TOP}$-DIPPS)

(1) Preparation of Diisopropylphenylsilane

Phenyl lithium (1.6 M dibutylether solution, 20.5 mL, 32.8 mmol) was dissolved in dehydrated tetrahydrofuran (60 mL) cooled to −78° C. While the solution was stirred at the same temperature, diisopropylchlorosilane (5.20 mL, 30.4 mmol) was added thereto dropwise over 6 min to give a dark brown solution. The reaction mixture was stirred at the same temperature for 30 min to give a pale-brown solution. To the reaction mixture was added saturated aqueous ammonium chloride solution (50 mL), and the mixture was warmed to room temperature and the aqueous layer and the organic layer were separated. The aqueous layer was extracted with dichloromethane (20 mL). The combined organic layer was washed with water and then saturated brine, dehydrated over sodium sulfate, the solvent was evaporated under reduced pressure to give a pale-brown oily liquid (14.9 g) containing the object diisopropylphenylsilane. This was used in the step without purification.

(2) Synthesis of 5'-(4,4'-dimethoxytrityl)-3'-diisopropylphenylsilyldeoxythymidine

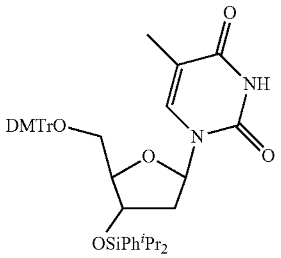

An oily liquid containing diisopropylphenylsilane obtained in (1) was dissolved in dry dichloromethane (30 mL), and molecular sieve 3A (0.5 g) activated under heating was added. After dehydrating, the solution was filtered. Dichloromethane (282 mL) was further added. To the solution was added 1,3-dichloro-5,5-dimethylhydantoin (9.54 g, 48.4 mmol), and the mixture was stirred at room temperature for 30 min. Imidazole (7.20 g, 106 mmol) and successively, 5'-(4,4'-dimethoxytrityl)deoxythymidine (13.0 g, 23.8 mmol) were added and the mixture was stirred at room temperature for 50 min. To the reaction mixture was added saturated aqueous sodium hydrogen carbonate solution (50 mL) to quench the reaction, and the mixture was partitioned. The organic layer was washed with water and then saturated brine, and further washed with aqueous sodium hydrogen carbonate solution. The organic layer was dehydrated over sodium sulfate, and the solvent was evaporated under reduced pressure to give a brown solid. This was purified by silica gel column chromatography (hexane:ethyl acetate=10:1-1:1) to give the object 5'-(4,4'-dimethoxytrityl)-3'-diisopropylphenylsilyldeoxythymidine (9.80 g, 13.3 mmol, 55.9%) as a white solid. $^1H$ NMR (400 MHZ, $CDCl_3$) δ: 0.95-1.02 (m, 12H, $2CH(CH_3)_2$), 1.18-1.24 (m, 2H, $2CH(CH_3)_2$), 1.46 (d, J=0.8 Hz, 3H, $CH_3$ (thymidine)), 2.23 (ddd, J=13.4, 8.0, 5.6 Hz, 1H, 2'-CHH), 2.44 (ddd, J=13.4, 6.0, 2.0 Hz, 1H, 2'-CHH), 3.24 (dd, J=10.8, 2.8 Hz, 1H, 5'-CHH), 3.44 (dd, J=10.8, 2.8 Hz, 2H, 5'-CHH), 3.78 (s, 6H, 2 ($-OCH_3$)), 4.09-4.15 (m, 2H), 4.64 (m, 1H, 3'-CH), 6.47 (dd, J=8.0, 5.6 Hz, 1H, 1'-CH), 6.80 (dd, J=8.8, 4.4 Hz, 4H, 3,3',5,5'-CH of DMTr), 7.15-7.40 (m, 11H), 7.46 (d, J=6.8 Hz, 2H, 2,6-CH of Si-Ph), 7.63 (s, 1H, 6-CH (thymidine)), 8.40 (brs, 1H, 3-NH).

(3) Preparation of 3,4,5-Trisoctadecyloxybenzoyl Chloride

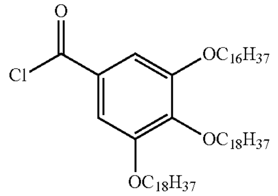

3,4,5-Tris (octadecyloxy)benzoic acid (14.4 g, 15.5 mmol) was suspended in chloroform (54.2 mL) to give a slurry. Two drops of N,N-dimethylformamide and thionyl chloride (2.25 mL, 31.0 mmol) were added and the mixture was stirred at 35° C. for 2 hr. The solvent was evaporated under reduced pressure. The obtained pale-yellow solid was dissolved in dehydrated toluene, and evaporated together with excessive thionyl chloride under reduced pressure. This operation was repeated twice and the solid was dried under reduced pressure to quantitatively give the object 3,4,5-tris (octadecyloxy)benzoyl chloride.

$^1H$ NMR (400 MHZ, $CDCl_3$) δ: 0.879 (t, J=6.6 Hz, 9H, $CH_3$), 1.2-1.9 (m, 96H, $CH_2$), 4.01 (t, J=6.4 ppm, 4H, 3,5-$OCH_2$), 4.07 (t, J=6.4 Hz, 2H, 4-$OCH_2$), 7.32 (s, 2H, Ar).

(4) Synthesis of 5'-(4,4'-dimethoxytrityl)-3'-diisopropylphenylsilyl-$N^3$-[3,4,5-tris(octadecyloxy)benzoyl]-deoxythymidine (DMTr-$dT^{CO-TOP}$-DIPPS)

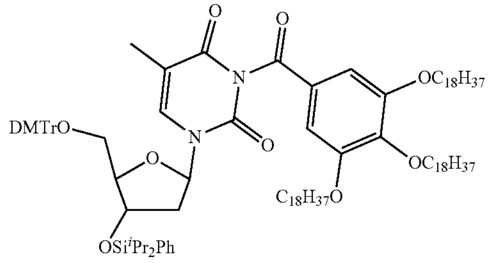

5'-(4,4'-Dimethoxytrityl)-3'-diisopropylphenylsilyldeoxythymidine (5.14 g, 6.99 mmol) obtained in (2), 3,4,5-tris(octadecyloxy)benzoyl chloride (9.97 g, 10.5 mmol) obtained in (3) and diisopropylethylamine (3.62 g, 14.0 mmol) were dissolved in dehydrated pyridine (65.0 mL), and the mixture was stirred at 65° C. for 4 hr. Completion of the reaction was confirmed by TLC, pyridine was evaporated and the solid was slurry washed in acetonitrile and filtered. The solid was suspended in dichloromethane and filtered. The recovered dichloromethane solution was concentrated to give a pale-brown solid. This was purified by silica gel column chromatography to give the object DMTr-dT$^{CO-TOP}$-DIPPS (9.52 g, 5.79 mmol, 82.7%).

$^1$H NMR (400 MHZ, $CDCl_3$) δ: 0.878 (t, J=7.2 Hz, 9H, octadecyl-$CH_3$), 0.94-1.00 (m, 12H, $SiCH(CH_3)_2$), 1.19-1.85 (m, 101H, octadecyl-$CH_2$, thymine-$CH_3$ and $SiCH(CH_3)_2$), 2.22-2.29 (m, 1H, 2'-CHH), 2.46-2.53 (m, 1H, 2'-CHH), 3.27 (dd, J=10.8, 2.4 Hz, 1H, 5'-CHH), 3.47 (dd, J=10.8, 2.4 Hz, 1H, 5'-CHH), 3.79 (s, 6H, $OCH_3$ of DMTr), 3.98 (t, J=6.4 Hz, 4H, 3,5-$OCH_2(CH_2)_{16}CH_3$), 4.03 (t, J=6.4 Hz, 2H, 4-$OCH_2(CH_2)_{16}CH_3$), 4.17 (m, 1H, 4'-H), 4.64 (m, 1H, 3'-H), 6.46 (dd, J=5.6, 8.0 Hz, 1H, 1'-H), 6.79-6.83 (m, 4H, 3,3',5,5'-H of DMTr), 7.14 (s, 2H, 2,6-H of substituted benzoate), 7.2-7.5 (m, 14H, Ar), 7.75 (s, 1H, 6-H of thymidine).

Example 9: Synthesis of 5'-O-(4,4'-dimethoxytrityl) deoxythymidine 3'-[O-(2-cyanoethyl)]phosphorothionyl-N$^4$-benzoyldeoxycytidine 3'-[O-(2-cyanoethyl)]phosphorothionyl-N$^4$-benzoyldeoxycytidine 3'-[O-(2-cyanoethyl)]phosphorothionyl-N$^4$-benzoyldeoxycytidine 3'-[O-(2-cyanoethyl)]phosphorothionyl-N$^2$-isobutyryldeoxyguanosine 3'-[O-(2-cyanoethyl)]phosphorothionyl-N$^4$-benzoyldeoxycytidine 3'-[O-(2-cyanoethyl)]phosphorothionyl-N$^4$-benzoyldeoxycytidine 3'-[O-(2-cyanoethyl)]phosphorothionyl-deoxythymidine 3'-[O-(2-cyanoethyl)]phosphorothionyl-N$^2$-isobutyryldeoxyguanosine 3'-[O-(2-cyanoethyl)]phosphorothionyl-N$^3$-[3,4,5-tris(octadecyloxy)benzoyl]-3'-diisopropylphenylsilyldeoxythymidine (DMTr-d[TC$^{Bz}$C$^{Bz}$C$^{Bz}$C$^{Bz}$G$^{iBu}$C$^{Bz}$C$^{Bz}$TG$^{iBu}$T$^{CO-TOP}$]-DIPPS)

(1): Synthesis of 5'-O-(4,4'-dimethoxytrityl)-N$^2$-isobutyryldeoxyguanosine 3'-[O-(2-cyanoethyl)] phosphorothionyl-N$^3$-[3,4,5-tris(octadecyloxy)benzoyl]-3'-diisopropylphenylsilyldeoxythymidine (DMTr-d[G$^{iBu}$T$^{CO-TOP}$]-DIPPS)

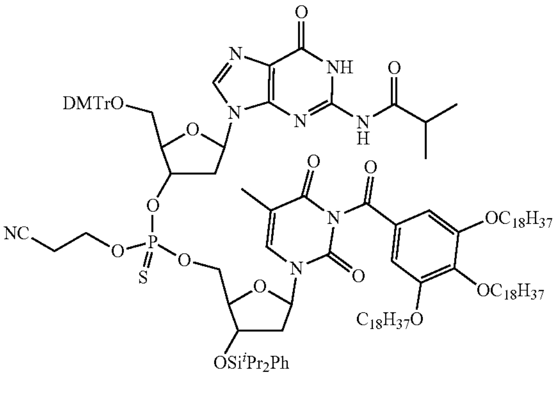

DMTr-dT$^{CO-TOP}$-DIPPS (1.49 g, 0.903 mmol) obtained in the Same manner as in Example 8 and 3,4,5-tris(octadecyloxy)benzylacetate (1.38 g, 1.44 mmol) and indole (1.37 g, 1.17 mmol) was dissolved in dehydrated dichloromethane (50 mL), and trifluoroacetic acid (0.103 mL, 1.34 mmol) was added dropwise. The reaction mixture was stirred at room temperature for 1 hr, and dedimethoxytritylation was confirmed by thin layer chromatography. The reaction mixture was neutralized with 1-methylimidazole (0.112 mL, 1.42 mmol). A solution (12.5 mL) of 5'-(4,4'-dimethoxytrityl)-N$^2$-isobutyryl-2'-deoxyguanosine-3'-[(2-cyanoethyl) (N,N-diisopropyl)]phosphoramidite (2.04 g, 2.43 mmol) and 4,5-dicyanoimidazole (0.422 g, 3.57 mmol) in dehydrated acetonitrile was added and the mixture was stirred at room temperature for 1 hr 30 min, and completion of the coupling reaction was confirmed by thin layer chromatography. 3-[(N,N-dimethylaminomethylidene)amino]-3H-1,2,4-dithiazole-5-thione (0.540 g, 2.63 mmol) was added and the mixture was stirred at room temperature for 10 min to sulfurate_phosphite intermediate. Successively, acetic anhydride (80.1 μL), 2,4,6-trimethylpyridine (119 μL), 1-methylimidazole (71.2 μL) were added and the mixture was stirred at room temperature for 30 min. To the reaction mixture was added acetonitrile (200 mL) at room temperature, and the object compound and 3,4,5-tris(octadecyloxy) benzylacetate were precipitated. The precipitate was filtered using a hirsch funnel and washed (acetonitrile). The obtained solid was dried to quantitatively give DMTr-d[G$^{iBu}$T$^{CO-TOP}$]-DIPPS.

The sample was dissolved in tetrahydrofuran, the cyanoethyl-protecting group on phosphoric acid was made to fall off with DBU, and the object product was identified by LC/MS. LC/MS m/z: calcd 2057.26, found 1185.64 $[M-2H]^{2-}$.

(2) Synthesis of 5'-O-(4,4'-dimethoxytrityl)deoxythymidine 3'-[O-(2-cyanoethyl)]phosphorothionyl-$N^2$-isobutyryldeoxyguanosine 3'-[O-(2-cyanoethyl)] phosphorothionyl-$N^3$-[3,4,5-tris(octadecyloxy) benzoyl]-3'-diisopropylphenylsilyldeoxythymidine (DMTr-d[TG$^{iBu}$T$^{CO-TOF}$]-DIPPS)

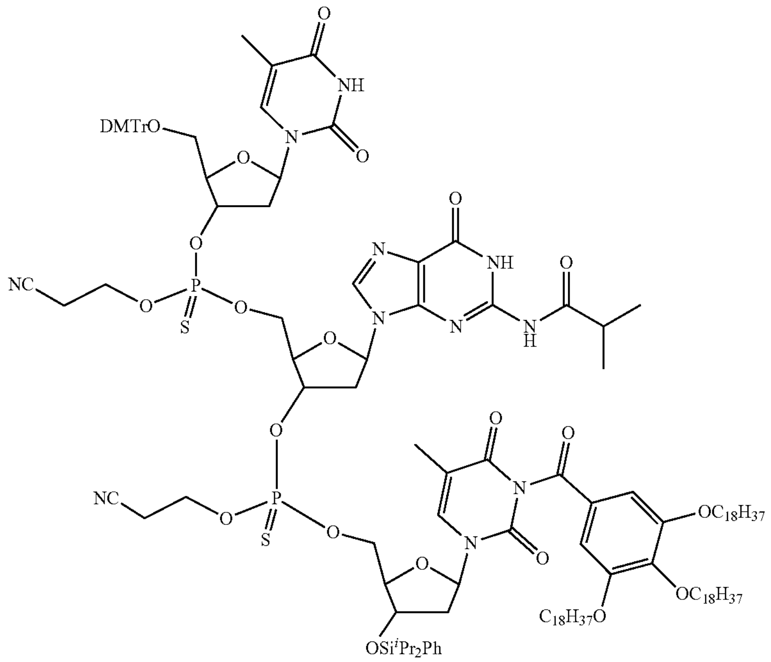

A mixture of DMTr-d[G$^{iBu}$T$^{CO-TOF}$]-$^{DIPPS}$ (0.903 mmol) obtained in (1) and 3,4,5-tris(octadecyloxy)benzylacetate, and indole (1.42 g, 12.1 mmol) were dissolved in dry dichloromethane (50.0 mL). Thereto was added dropwise trifluoroacetic acid (106 μL, 1.39 mmol), and the mixture was stirred at room temperature for 1 hr. Completion of dedimethoxytritylation was confirmed by LC/MS, and the mixture was neutralized with 1-methylimidazole (116 μL, 1.46 mmol). To the reaction mixture was added a solution of 5'-(4,4'-dimethoxytrityl)-deoxythymidine-3'-[(2-cyanoethyl)-N,N-diisopropyl] phosphoramidite (2.00 g, 2.69 mmol) and 4,5-dicyanoimidazole (0.479 g, 4.05 mmol) in dehydrated acetonitrile (12.5 mL) and the mixture was stirred at room temperature for 1 hr 30 min, and completion of a coupling reaction was confirmed by LC/MS. Successively, 3-[(N,N-dimethylaminomethylidene)amino]-3H-1,2,4-dithiazole-5-thione (0.612 g, 2.98 mmol) was added and the mixture was stirred for 10 min to sulfurate_phosphite intermediate. To the reaction mixture were added acetic anhydride (87.6 μL, 0.927 mmol), 2,4,6-trimethylpyridine (123 μL, 0.927 mmol), 1-methylimidazole (73.3 μL, 0.927 mmol) and the mixture was stirred for 10 min. To the reaction mixture was added acetonitrile (200 mL) to precipitate a mixture of oligonucleic acid trimer and 2,4,6-tris (octadecyloxy)benzylacetate. The suspension was filtered and washed to give the object nucleic acid trimer and 3,4,6-tris(octadecyloxy)benzylacetate in a mixture (3.56 g of which nucleic acid was 2.21 g, 0.887 mmol, 95.7% yield).

The sample was dissolved in tetrahydrofuran, the cyanoethyl-protecting group on phosphoric acid was made to fall off with DBU, and the object product was identified by LC/MS. LC/MS m/z: calcd 1188.14, found 1188.14 $[M-2H]^{2-}$.

(3) Synthesis of 5'-O-(4,4'-dimethoxytrityl)deoxythymidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-deoxythymidine 3'-[O-(2-cyanoethyl)]phosphorothionyl-$N^2$-isobutyryldeoxyguanosine 3'-[O-(2-cyanoethyl)]phosphorothionyl-$N^3$-[3,4,5-tris(octadecyloxy)benzoyl]-3'-diisopropylphenylsilyldeoxythymidine (DMTr-d[$TC^{Bz}C^{Bz}C^{Bz}G^{iBu}C^{Bz}C^{Bz}TG^{iBU}T^{CO-TOP}$] (SEQ ID NO: 1)-DIPPS)

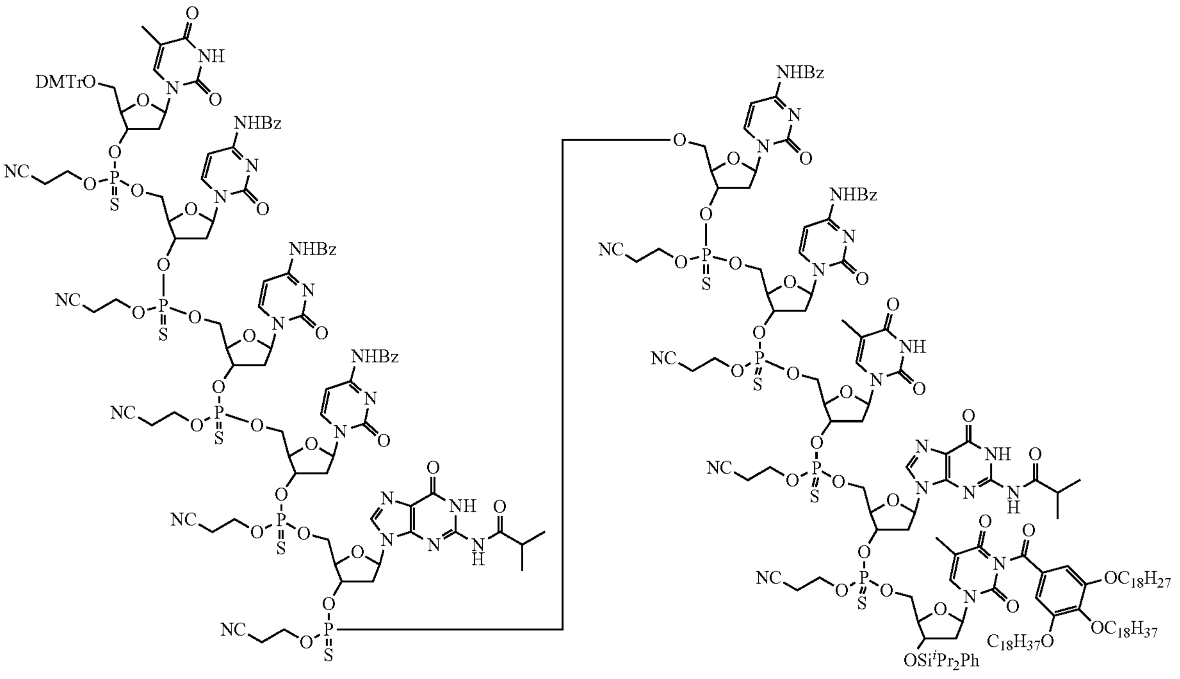

DMTr-d[$TG^{iBu}T^{CO-TOP}$]-DIPPS obtained in (2) was elongated by successively using nucleoside amidite corresponding to a desired sequence in the same manner as in (2). As the nucleoside amidite, the following were used.

$dC^{Bz}$: 5'-(4,4'-dimethoxytrityl)-$N^4$-benzoyl-2'-deoxycytidine-3'-[(2-cyanoethyl)-N,N-diisopropyl]phosphoramidite $dG^{iBu}$: 5'-(4,4'-dimethoxytrityl)-$N^2$-isobutyryl-2'-deoxyguanosine-3'-[(2-cyanoethyl)-N,N-diisopropyl]phosphoramidite dT: 5'-(4,4'-dimethoxytrityl)-2'-deoxythymidine-3'-[(2-cyanoethyl)-N,N-diisopropyl]phosphoramidite The yield of each step is shown below.

TABLE 1

| monomer | resultant product | yield (%) |
|---|---|---|
| 5'-(4,4'-dimethoxytrityl)-$N^2$-isobutyryl-2'-deoxyguanosine-3'-[(2-cyanoethyl)-N,N-diisopropyl]phosphoramidite | DMTr-d[$G^{iBu}T^{CO\cdot TOP}$]-DIPPS | 100 |
| 5'-(4,4'-dimethoxytrityl)-2'-deoxythymidine-3'-[(2-cyanoethyl)-N,N-diisopropyl]phosphoramidite | DMTr-d[$TG^{iBu}T^{CO\cdot TOP}$]-DIPPS | 95.7 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}TG^{iBu}T^{CO\cdot TOP}$]-DIPPS | 94.1 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}C^{Bz}TG^{iBu}T^{CO\cdot TOP}$]-DIPPS | 96.9 |
| 5'-(4,4'-dimethoxytrityl)-$N^2$-isobutyryl-2'deoxyguanosine-3'-[(2-cyanoethyl)-N,N-diisopropyl]phosphoramidite | DMTr-d[$G^{iBu}C^{Bz}C^{Bz}TG^{iBu}T^{CO\cdot TOP}$]-DIPPS | 95.5 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}G^{iBu}C^{Bz}C^{Bz}TG^{iBu}T^{CO\cdot TOP}$]-DIPPS | 93.5 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}C^{Bz}G^{iBu}C^{Bz}C^{Bz}TG^{iBu}T^{CO\cdot TOP}$]-DIPPS | 91.9 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}C^{Bz}C^{Bz}G^{iBu}C^{Bz}C^{Bz}TG^{iBu}T^{CO\cdot TOP}$]-DIPPS | 96.5 |
| 5'-(4,4'-dimethoxytrityl)-2'-deoxythymidine-3'-[(2-cyanoethyl)-N,N-diisopropyl]phosphoramidite | DMTr-3 [$TC^{Bz}C^{Bz}C^{Bz}G^{iBu}C^{Bz}C^{Bz}TG^{iBu}T^{CO\cdot TOP}$] SEQ ID NO: 1)-DIPPS | 96.5 |

The sample was dissolved in tetrahydrofuran, the cyanoethyl-protecting group on phosphoric acid was made to fall off with DBU, and the object product was identified by LC/MS. LC/MS m/z: calcd 1030.72, found 1030.72 $[M-5H]^{5-}$.

Example 10: Synthesis of 5'-O-(4,4'-dimethoxytrityl)deoxythymidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyldeoxythymidine 3'-[O-(2-cyanoethyl)]phosphorothionyl-$N^2$-isobutyryldeoxyguanosine 3'-[O-(2-cyanoethyl)]phosphorothionyl-$N^3$-[3,4,5-tris(octadecyloxy)benzoyl]deoxythymidine (DMTr-d[$TC^{Bz}C^{Bz}C^{Bz}G^{iBu}C^{Bz}C^{Bz}TG^{iBu}T^{CO\text{-}TOP}$] (SEQ ID NO: 1)-H) (desilylation)

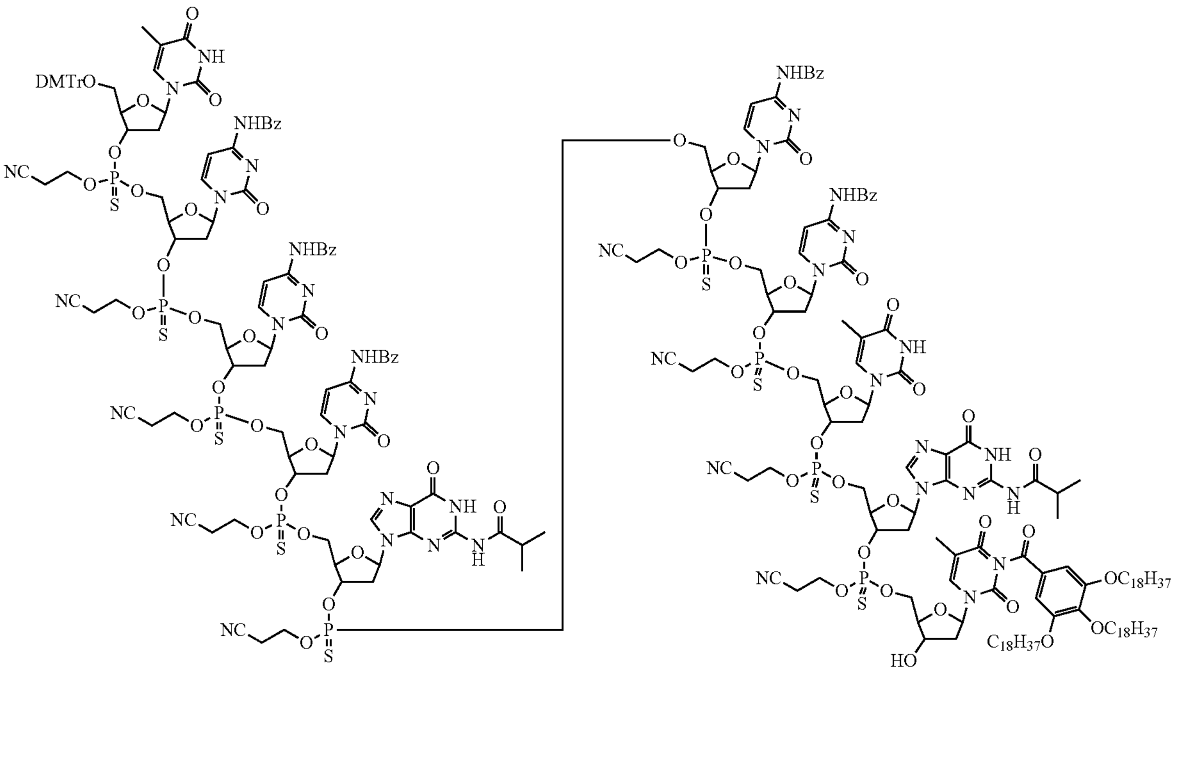

A mixture (1.69 g, 0.235 mmol) of DMTr-d[$TC^{Bz}C^{Bz}C^{Bz}$-$G^{iBu}TG^{iBz}T^{CO\text{-}TOP}$]-DIPPS obtained in Example 9 and 3,4,5-tris(octadecyloxy)benzylacetate at a molar ratio of 1.00:1.60 was dissolved in dichloromethane (7.20 mL) and the mixture was cooled to 10° C. Thereto was added a solution of triethylamine trihydrofluoride (0.174 g, 1.08 mmol), pyridine (175 μL, 2.16 mmol) in tetrahydrofuran (14.4 mL). The reaction mixture was stirred at 10° C. for 24 hr and completion of desilylation was confirmed by LC/MS. To the reaction mixture was added acetonitrile (100 mL) to precipitate a mixture of the object DMTr-d[$TC^{Bz}C^{Bz}C^{Bz}G^{iBu}C^{Bz}C^{Bz}TG^{iBu}T^{CO\text{-}TOP}$]-OH and 3,4,5-tris(octadecyloxy)benzylacetate. The solid was obtained by filtration using a hirsch funnel, washed with acetonitrile and dried in vacuo to give a white solid (1.46 g, of which oligonucleic acid was 1.14 g, 0.209 mmol, 87.5% yield).

The sample was dissolved in tetrahydrofuran, the cyanoethyl-protecting group on phosphoric acid was made to fall off with DBU, and the object product was identified by LC/MS. Analysis by HPLC showed a peak of short chain in the subsequent retention time of the object compound, and the area ratio of the peak of the object compound was 94.0%.

LC/MS m/z: calcd 1655.16, found 1655.14 $[M-3H]^{3-}$.

Example 11: Synthesis of 5'-O-(4,4'-dimethoxytrityl)deoxythymidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-deoxythymidine 3'-[O-(2-cyanoethyl)]phosphorothionyl-$N^2$-isobutyryldeoxyguanosine 3'-[O-(2-cyanoethyl)]phosphorothionyl-$N^3$-[3,4,5-tris(octadecyloxy)benzoyl]thymidine-3'-[(2-cyanoethyl)-N,N-diisopropyl]phosphoramidite (DMTr-d[$TC^{Bz}C^{Bz}C^{Bz}G^{iBu}C^{Bz}C^{Bz}TG^{iBU}T^{CO-TOP}$] (SEQ ID NO: 1)-PA)

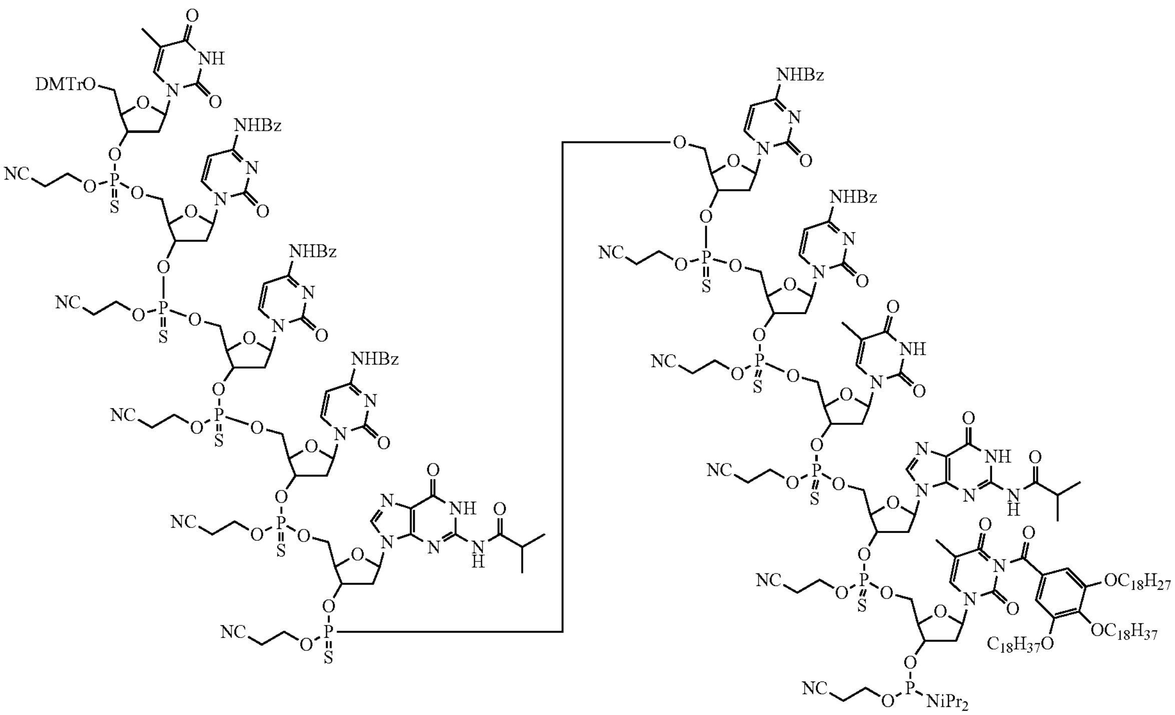

2-Cyanoethyl N,N,N',N'-tetraisopropylphosphordiamidite (0.971 mL, 3.06 mmol) was dissolved in dehydrated toluene (6.68 mL), dehydrated using molecular sieve 3A powder for 30 min and the solution (3.18 mL) was filtered through a 0.45 μm membrane filter. To the toluene solution was added 4,5-dicyanoimidazole (0.886 g, 7.5 mmol) and the mixture was stirred for 30 min and filtered through a 0.45 μm membrane filter to give a solution (1.28 ml). To the reaction mixture were added 2-cyanoethyl N,N,N',N'-tetraisopropylphosphordiamidite (0.162 mb, 0.510 mmol), N-methylmorpholine (0.572 mL, 5.10 mmol) and a mixture of DMTr-d[$TC^{Bz}C^{Bz}C^{Bz}G^{iBz}C^{Bz}C^{Bz}TG^{iBu}T^{CO-TOP}$]-H obtained in Example 10 as and 3,4,5-tris(octadecyloxy) benzylacetate at a molar ratio of 1.00:1.60 (1.18 g) at 15° C. to give a suspension. Dehydrated dichloromethane (16.0 mL) was added at the same temperature to give a uniform solution, and the solution was stirred for 6 hr. Completion of the reaction was confirmed by LC/MS and the reaction was discontinued with 2,4,6-trimethylpyridine. The reaction mixture was cooled to 0° C., acetonitrile (110 mL) was added, and the resultant product and 3,4,5-tris(octadecyloxy)benzylacetate were precipitated, filtered using a hirsch funnel, washed and dried in vacuo to give a mixture (1.13 g of which oligonucleic acid was 0.888 g, 0.1571 mmol, 92.4% yield) of DMTr-d[$TC^{Bz}C^{Bz}C^{Bz}G^{iBu}C^{Bz}C^{Bz}TG^{iBU}T^{CO-TOP}$]-PA and 3,4,5-tris(octadecyloxy)benzylacetate.

The sample was dissolved in tetrahydrofuran, the cyanoethyl-protecting group on phosphoric acid was made to fall off with DBU, and the object product was identified by LC/MS. LC/MS m/z: calcd 1709.52, found 1709.52 $[M-5H]^{5-}$.

Preparation Example 1: Synthesis of $N^2$-isobutyryldeoxyguanosine 3'-[O-(2-cyanoethyl)]phosphorothionyl-$N^4$-benzoyldeoxyadenosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxyadenosine 3'-[O-(2-cyanoethyl)]phosphorothionyldeoxythymidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxycytidine 3'-[O-(2-cyanoethyl)] phosphorothionyl-$N^4$-benzoyldeoxyadenosine 3'-[O-(2-cyanoethyl)]phosphorothionyldeoxythymidine 3'-[O-(2-cyanoethyl)]phosphorothionyl-deoxythymidin-3'-yl-[3,4,5-tris(octadecyloxy)benzyl]succinate (H-d[$G^{iBu}A^{Bz}C^{Bz}A^{Bz}TG^{iBu}C^{Bz}A^{Bz}$TT] (SEQ ID NO: 2)-suc-TOB)

(1) Synthesis of 5'-(4,4'-dimethoxytrityl)-deoxythymidine 3'-[O-(2-cyanoethyl)]phosphorothionyl-deoxythymidin-3'-yl-3,4,5-tris(octadecyloxy)benzylsuccinate (DMTr-d[Tr]-suc-TOB)

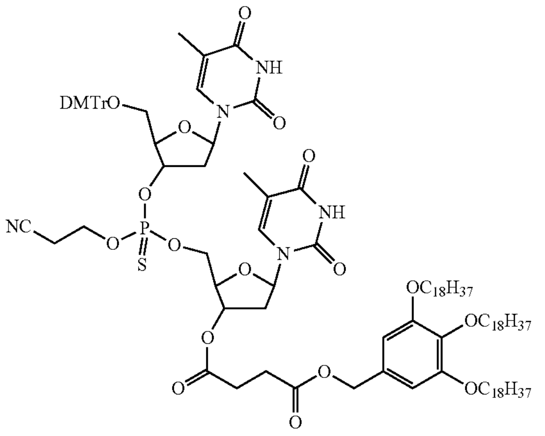

5'-(4,4'-Dimethoxytrityl)-deoxythymidin-3'-yl-[3,4,5-tris (octadecyloxy)benzyl] succinate (1.51 g, 0.977 mmol), 3,4, 5-tris(octadecyloxy)benzylacetate (1.49 g, 1.56 mmol) and indole (1.50 g, 12.7 mmol) were dissolved in dry dichloromethane (38.9 mL). Thereto was added dropwise trifluoroacetic acid (112 μL, 1.46 mmol), and the mixture was stirred at room temperature for 1 hr. Completion of dedimethoxytritylation was confirmed by thin layer chromatography and the mixture was neutralized with 1-methylimidazole (122 ML, 1.54 mmol). To the reaction mixture was added a solution of 5'-(4,4'-dimethoxytrityl)-2'-deoxythymidine-3'-[(2-cyanoethyl)-N,N-diisopropyl] phosphoramidite (2.00 g, 2.69 mmol) and 4,5-dicyanoimidazole (0.476 g, 4.03 mmol) in dehydrated acetonitrile (9.7 mL) and the mixture was stirred at room temperature for 2 hr. Successively, 3-[(N,N-dimethylaminomethylidene)amino]-3H-1,2, 4-dithiazole-5-thione (0.582 g, 2.83 mmol) was added and the mixture was stirred for 10 min to sulfurate_phosphite intermediate. To the reaction mixture were added acetic anhydride (92.1 μL, 0.974 mmol), 2,4,6-trimethylpyridine (129 μL, 0.974 mmol), 1-methylimidazole (77.1 μL, 0.974 mmol) and the mixture was stirred for 10 min. To the reaction mixture was added acetonitrile (200 mL) to precipitate a mixture of oligonucleic acid dimer and 2,4,6-tris (octadecyloxy)benzylacetate. The suspension was filtered and washed to give a mixture (3.24 g of which nucleic acid was 1.80 g, 0.943 mmol, 96.9% yield) of the object nucleic acid dimer and 3, 4, 6-tris(octadecyloxy)benzylacetate.

The sample was dissolved in tetrahydrofuran, the cyanoethyl-protecting group on phosphoric acid was made to fall off with DBU, and the object product was identified by LC/MS. LC/ESI TOF MS: calcd 1858.13, found 1858.13 $[M-H]^-$.

(2) Synthesis of 5'-(4,4'-dimethoxytrityl)-$N^4$-benzoyldeoxyadenosine 3'-[O-(2-cyanoethyl)]phosphorothionyl-deoxythymidine 3'-[O-(2-cyanoethyl)]phosphorothionyl-deoxythymidin-3'-yl-3,4,5-tris (octadecyloxy)benzylsuccinate (DMTr-d[$A^{Bz}$TT]-suc-TOB)

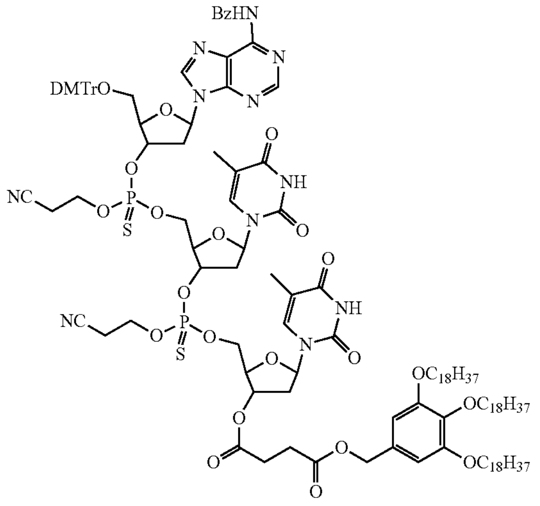

A mixture of DMTr-d[TT]-suc-TOB (0.977 mmol) obtained in (1) and 3,4,5-tris(octadecyloxy)benzylacetate, and indole (1.44 g, 12.2 mmol) were dissolved in dry dichloromethane (38.9 mL). Thereto was added dropwise trifluoroacetic acid (108 μL, 1.42 mmol), and the mixture was stirred at room temperature for 1 hr. Completion of dedimethoxytritylation was confirmed by LC/MS, and the mixture was neutralized with 1-methylimidazole (118 μL, 1.49 mmol). To the reaction mixture was added a solution of 5'-(4,4'-dimethoxytrityl)-$N^4$-benzoyl-2'-deoxyadenosine-3'-[(2-cyanoethyl)-N,N-diisopropyl] phosphoramidite (2.53 g, 2.95 mmol) and 4,5-dicyanoimidazole (0.526 g, 4.03 mmol) in dehydrated acetonitrile (10.0 mL) and the mixture was stirred at room temperature for 2 hr. Successively, 3-[(N,N-dimethylaminomethylidene)amino]-3H-1,2,4-dithiazole-5-thione (0.638 g, 3.11 mmol) was added and the mixture was stirred for 10 min to sulfurate phosphite intermediate. To the reaction mixture were added acetic anhydride (89.2 μL, 0.943 mmol), 2,4,6-trimethylpyridine (125 μL, 0.943 mmol), 1-methylimidazole (74.7 μL, 0.943 mmol) and the mixture was stirred for 10 min. To the reaction mixture was added acetonitrile (200 mL) to precipitate a mixture of oligonucleic acid trimer and 2,4,6-tris(octadecyloxy)benzylacetate. The suspension was filtered and washed to give the object nucleic acid trimer and 3,4,6-tris(octadecyloxy)benzylacetate in a mixture (3.59 g of which nucleic acid was 1.20 g, 0.916 mmol, 97.1% yield). The sample was dissolved in tetrahydrofuran, the cyanoethyl-protecting group on phosphoric acid was made to fall off with DBU, and the object product was identified by LC/MS.

LC/MS m/z: calcd 1145.09, found 1145.09 $[M-2H]^{2-}$.

(3) Synthesis of $N^4$-benzoyldeoxyadenosine 3'-[O-(2-cyanoethyl)]phosphorothionyl-deoxythymidine 3'-[O-(2-cyanoethyl)]phosphorothionyl-deoxythymidin-3'-yl-3,4,5-tris(octadecyloxy)benzylsuccinate (d[$A^{Bz}$TT]-suc-TOB) (de-DMTr-lation)

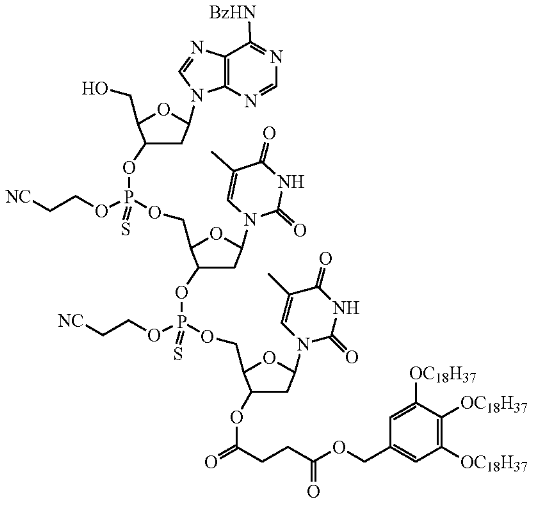

DMTr-d[$A^{Bz}$TT]-suc-TOB (2.49 g, 1.00 mol) obtained in (2) and 5-methoxyindole were dissolved in dehydrated dichloromethane (50 mL). Trifluoroacetic acid (76.5 μL, 1.00 mmol) was added, and the mixture was stirred at room temperature for 2 hr. Completion of dedimethoxytritylation was confirmed by LC/TOF MS, and 2,4,6-trimethylpyridine (265 μL, 2.00 mmol) was added. Acetonitrile (250 mL) was added and the object product was precipitated. Slurry was filtered using a hirsch funnel, washed and dried in vacuo to give the object compound (2.10 g, 0.999 mmol, 99.5%) as a white solid.

The sample was dissolved in tetrahydrofuran, the cyanoethyl-protecting group on phosphoric acid was made to fall off with DBU, and the object product was identified by LC/MS. LC/MS: calcd 1989.06, found 1989.09 $[M-H]^-$.

(4) Synthesis of 5'-O-(4,4'-dimethoxytrityl)-$N^2$-isobutyryldeoxyguanosine 3'-[O-(2-cyanoethyl)]phosphorothionyl-$N^4$-benzoyldeoxyadenosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxyadenosine 3'-[O-(2-cyanoethyl)]phosphorothionyl-deoxythymidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxyadenosine 3'-[O-(2-cyanoethyl)]phosphorothionyl-deoxythymidine 3'-[O-(2-cyanoethyl)]phosphorothionyl-deoxythymidin-3'-yl-3,4,5-tris(octadecyloxy)benzylsuccinate (DMTr-d[$G^{iBu}A^{Bz}C^{Bz}A^{Bz}TG^{iBu}C^{Bz}A^{Bz}$TT] (SEQ ID NO: 2)-suc-TOB)

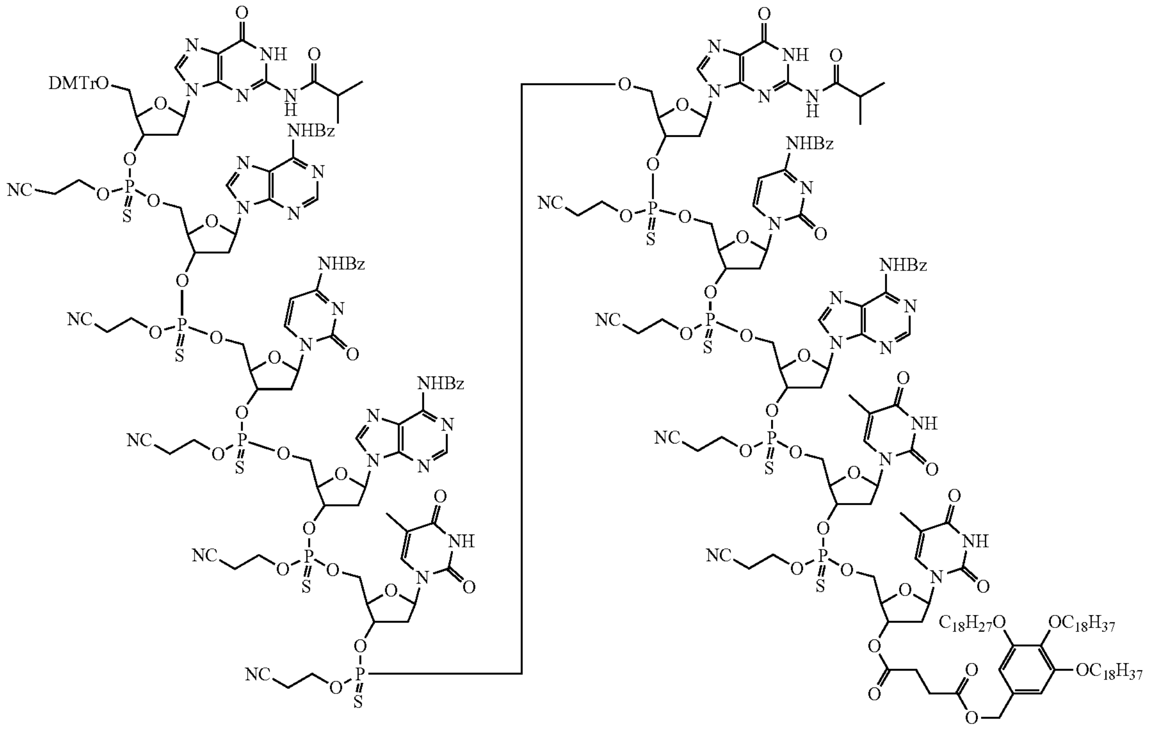

A mixture of d[$A^{Bz}$TT]-suc-TOB obtained in (3) and 3,4,5-tris(octadecyloxy)benzylacetate was elongated by successively using nucleoside amidite corresponding to a desired sequence in the same manner as in (1). As the nucleoside amidite, the following were used.

$dA^{Bz}$: 5'-(4,4'-dimethoxytrityl)-$N^4$-benzoyl-2'-deoxyadenosine-3'-[(2-cyanoethyl)-N,N-diisopropyl]phosphoramidite $dC^{Bz}$: 5'-(4,4'-dimethoxytrityl)-$N^4$-benzoyl-2'-deoxycytidine-3'-[(2-cyanoethyl)-N,N-diisopropyl]phosphoramidite $dG^{iBu}$: 5'-(4,4'-dimethoxytrityl)-$N^2$-isobutyryl-2'-deoxyguanosine-3'-[(2-cyanoethyl)-N,N-diisopropyl]phosphoramidite dT: 5'-(4,4'-dimethoxytrityl)-2'-deoxythymidine-3'-[(2-cyanoethyl)-N,N-diisopropyl]phosphoramidite The yield of each step is shown below.

TABLE 2

| monomer | resultant product | yield (%) |
|---|---|---|
| 5'-(4,4'-dimethoxytrityl )-2'-deoxythymidine-3'-[(2-cyanoethyl)-N,N-diisopropyl]phosphoramidite | DMTr-d[TT]-suc-TOB | 96.9 |
| 5'-(4,4'-dimethoxytrityl)-$N^4$-benzoyl-2'-deoxyadenosine-3'-[(2-cyanoethyl)-N,N-diisopropyl]phosphoramidite | DMTr-d[$A^{Bz}$TT]-suc-TOB | 97.2 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}A^{Bz}$TT]-suc-TOB | 100 |
| 5'-(4,4'-dimethoxytrityl)-$N^2$-isobutyryl-2'-deoxyguanosine-3'-[(2-cyanoethyl)-N,N-diisopropyl]phosphoramidite | DMTr-d[$G^{iBu}C^{Bz}A^{Bz}$TT]-suc-TOB | 98.0 |
| 5'-(4,4'-dimethoxytrityl)-2'-deoxythymidine-3'-[(2-cyanoethyl)-N,N-diisopropyl]phosphoramidite | DMTr-d[T$G^{iBu}C^{Bz}A^{Bz}$TT]-suc-TOB | 97.9 |
| 5'-(4,4'-dimethoxytrityl)-$N^4$-benzoyl-2'-deoxyadenosine-3'-[(2-cyanoethyl)-N,N-diisopropyl]phosphoramidite | DMTr-d[$A^{Bz}$T$G^{iBu}C^{Bz}A^{Bz}$TT]-suc-TOB | 99.5 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}A^{Bz}$T$G^{iBu}C^{Bz}A^{Bz}$TT]-suc-TOB | 99.0 |
| 5'-(4,4'-dimethoxytrityl)-$N^4$-benzoyl-2'-deoxyadenosine-3'-[(2-cyanoethyl)-N,N-diisopropyl]phosphoramidite | DMTr-d[$A^{Bz}C^{Bz}A^{Bz}$T$G^{iBu}C^{Bz}A^{Bz}$TT]-suc-TOB | 100 |
| 5'-(4,4'-dimethoxytrityl)-$N^2$-isobutyryl-2'-deoxyguanosine-3'-[(2-cyanoethyl)-N,N-diisopropyl]phosphoramidite | DMTr-d[$G^{iBu}A^{Bz}C^{Bz}A^{Bz}$T$G^{iBu}C^{Bz}A^{Bz}$TT] (SEQ ID NO: 2))-suc-TOB | 99.5 |

The sample was dissolved in tetrahydrofuran, the cyanoethyl-protecting group on phosphoric acid was made to fall off with DBU, and the object product was identified by LC/MS. LC/MS m/z: calcd 1280.64, found 1280.66 $[M-4H]^{4-}$.

(5) Synthesis of $N^2$-isobutyryldeoxyguanosine 3'-[O-(2-cyanoethyl)]phosphorothionyl-$N^4$-benzoyldeoxyadenosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxyadenosine 3'-[O-(2-cyanoethyl)] phosphorothionyl-deoxythymidine 3'-[O-(2-cyanoethyl)]phosphorothionyl-$N^2$-isobutyryldeoxyguanosine 3'-[O-(2-cyanoethyl)] phosphorothionyl-$N^4$-benzoyldeoxycytidine 3'-[O-(2-cyanoethyl)]phosphorothionyl-$N^4$-deoxyadenosine 3'-[O-(2-cyanoethyl)] phosphorothionyl-deoxythymidine 3'-[O-(2-cyanoethyl)]phosphorothionyl-deoxythymidin-3'-yl-3,4,5-tris(octadecyloxy)benzylsuccinate (H-d[$G^{iBu}A^{Bz}C^{Bz}A^{Bz}TG^{iBu}C^{Bz}A^{Bz}TT$] (SEQ ID NO: 2)-suc-TOB) (de-DMTr-lation)

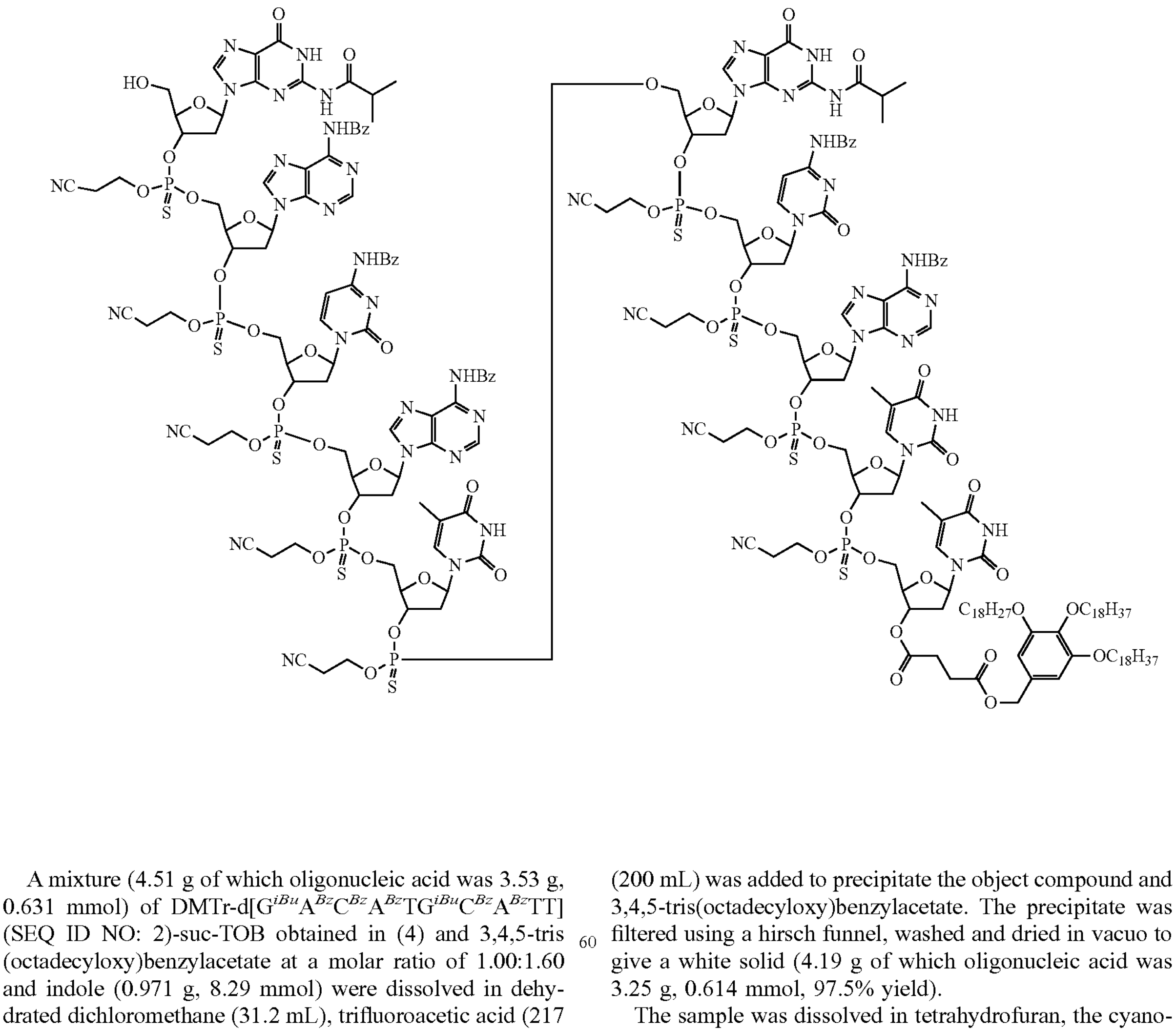

A mixture (4.51 g of which oligonucleic acid was 3.53 g, 0.631 mmol) of DMTr-d[$G^{iBu}A^{Bz}C^{Bz}A^{Bz}TG^{iBu}C^{Bz}A^{Bz}TT$] (SEQ ID NO: 2)-suc-TOB obtained in (4) and 3,4,5-tris (octadecyloxy)benzylacetate at a molar ratio of 1.00:1.60 and indole (0.971 g, 8.29 mmol) were dissolved in dehydrated dichloromethane (31.2 mL), trifluoroacetic acid (217 μL, 2.84 mmol) was added, and the mixture was stirred at room temperature for 2 hr. Completion of dedimethoxytritylation was confirmed by LC/TOF MS. After neutralization with 1-methylimidazole (236 μL, 2.98 mmol), acetonitrile (200 mL) was added to precipitate the object compound and 3,4,5-tris(octadecyloxy)benzylacetate. The precipitate was filtered using a hirsch funnel, washed and dried in vacuo to give a white solid (4.19 g of which oligonucleic acid was 3.25 g, 0.614 mmol, 97.5% yield).

The sample was dissolved in tetrahydrofuran, the cyanoethyl-protecting group on phosphoric acid was made to fall off with 1,8-diazabicyclo[5.4.0]undec-7-ene (hereinafter DBU), and the object product was identified by LC/MS.

LC/MS m/z: calcd 1205.11, found 1205.13 $[M-4H]^{4-}$.

Example 12: Synthesis of 5'-O-(4,4'-dimethoxytrityl)deoxythymidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-deoxythymidine 3'-[O-(2-cyanoethyl)]phosphorothionyl-$N^2$-isobutyryldeoxyguanosine 3'-[O-(2-cyanoethyl)]phosphorothionyl-$N^3$-[3,4,5-tris(octadecyloxy)benzoyl]thymidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxyadenosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxyadenosine 3'-[O-(2-cyanoethyl)]phosphorothionyl-deoxythymidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxyadenosine 3'-[O-(2-cyanoethyl)]phosphorothionyl-deoxythymidine 3'-[O-(2-cyanoethyl)]phosphorothionyl-deoxythymidin-3'-yl-3,4,5-tris(octadecyloxy)benzylsuccinate (DMTr-d[$TC^{Bz}C^{Bz}C^{Bz}G^{iBu}C^{Bz}C^{Bz}TG^{iBu}T^{CO\text{-}TOP}G^{iBu}A^{Bz}C^{Bz}A^{Bz}TG^{iBu}C^{Bz}A^{Bz}TT$] (SEQ ID NO: 3)-suc-TOB)

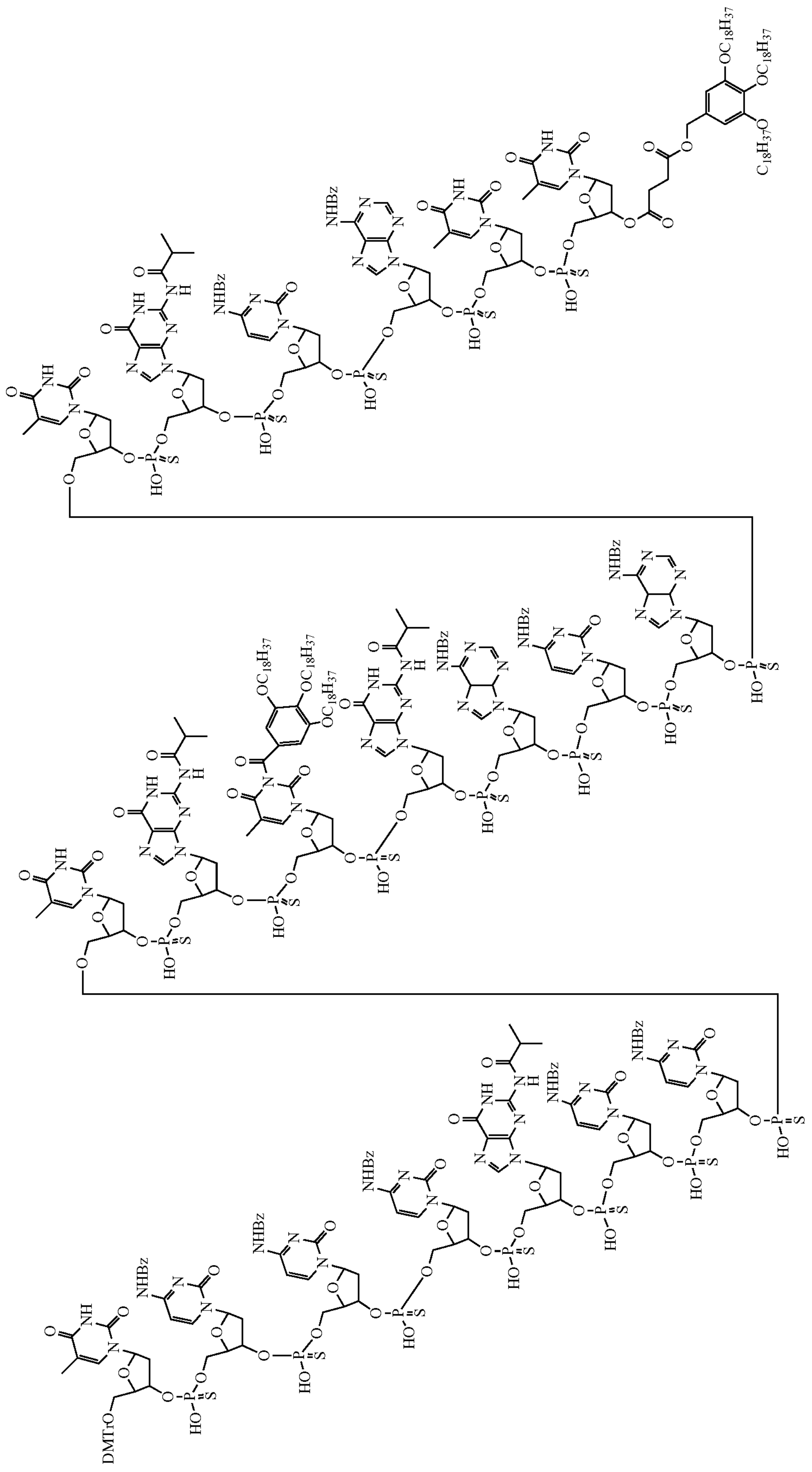

A mixture (0.0862 g, 0.121 mmol) of DMTr-d[$TC^{Bz}C^{Bz}C^{Bz}G^{iBu}C^{Bz}C^{Bz}TG^{iBu}T^{CO\text{-}TOP}$]-PA obtained in Example 11 and 3,4,5-tris(octadecyloxy)benzylacetate at a molar ratio of 1.00:1.60 and a mixture (0.0678 g, 0.0100 mmol) of H-d[$G^{iBu}A^{Bz}C^{Bz}A^{Bz}TG^{iBu}C^{Bz}A^{Bz}TT$]-suc-TOB obtained in Preparation Example 1 and 3,4,5-tris(octadecyloxy)benzylacetate at a molar ratio of 1.00:1.61 were dissolved in dehydrated dichloromethane (1.0 mL) and dehydrated with molecular sieve 3A (0.0588 g). The solution (0.6 mb) was filtered through a 0.45 μm membrane filter and obtained in a dry 5φ NMR tube. To the solution was added 5-(benzylthio)-1H-tetrazole (2.88 mg, 0.0149 mmol) and as the mixture was stirred at room temperature for 3 hr. Completion of condensation was confirmed by $^{31}P\{^1H\}$NMR, pyridine (9.7 μL, 0.12 mmol) and then 3-[(N,N-dimethylaminomethylidene)amino]-3H-1,2,4-dithiazole-5-thione (2.82 mg, 0.0137 mmol) were added, and the mixture was stirred at room temperature for 30 min to sulfurate_phosphite intermediate. To the reaction mixture was added methanol (4 mL) to precipitate the object product. The product was filtered using a hirsch funnel, washed and dried in vacuo to give a white solid (0.0931 g) as a coupling resultant product.

The sample was dissolved in tetrahydrofuran, the cyanoethyl-protecting group on phosphoric acid was made to fall off with DBU, and the object product was identified by LC/MS. LC/MS m/z: calcd 1095.76, found 1095.66 $[M-5H]^{5-}$.

Example 13: Synthesis of 5'-(4,4'-dimethoxytrityl)-3'-tert-butyldimethylsilyl-4-[3,4,5-tris(octadecyloxy)benzoyl]deoxythymidine (DMTr-d$T^{CO\text{-}TOP}$-TBDMS)

(1) Synthesis of 5'-(4,4'-dimethoxytrityl)-3'-tert-butyldimethylsilyldeoxythymidine (DMTr-dT-TBDMS)

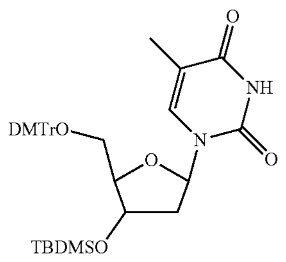

5'-(4,4'-Dimethoxytrityl)deoxythymidine (3.24 g, 5.95 mmol) and imidazole (1.03 g, 15.1 mmol) were dissolved in dehydrated N,N-dimethylformamide (12 mL). Thereto was added tert-butyldimethylsilylchloride (1.35 g, 8.95 mmol) and the mixture was stirred under argon at 45° C. for 1.5 hr. The reaction mixture was cooled to room temperature, dichloromethane (10 mL), 5% aqueous sodium hydrogen carbonate solution (10 mL) were added and the mixture was stirred. After partitioning, the aqueous layer was extracted with 10 mL of dichloromethane and the combined organic layer was washed with water (10 mL×2) and saturated brine (10 mL). Dichloromethane solution was dehydrated over anhydrous sodium sulfate, filtered and concentrated under reduced pressure. The obtained pale-yellow transparent oil was purified by silica gel column chromatography (hexane: ethyl acetate=2:1-3:2) to give the object DMTr-dT-TBDMS as a white solid (3.29 g, 4.9 mmol, 84.0%).

(2) Synthesis of 5'-(4,4'-dimethoxytrityl)-3'-tert-butyldimethylsilyl-4-[3,4,5-tris(octadecyloxy)benzoyl]thymidine (DMTr-d$T^{CO\text{-}TOP}$-TBDMS)

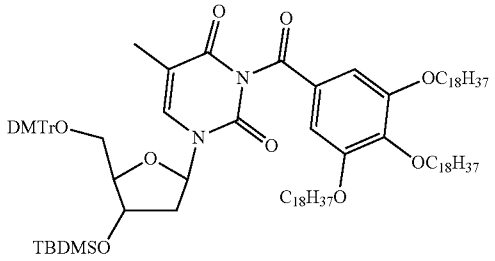

DMTr-dT-TBMDS (3.28 g, 4.98 mmol) obtained in (1) was dissolved in dehydrated pyridine (45 mL). Thereto was added 3,4,5-tris(octadecyloxy)benzoyl chloride (6.91 g, 7.3 mmol), diisopropylethylamine (3.9 mL, 22.4 mmol), and the mixture was stirred at 65° C. for 6 hr. The reaction mixture was cooled to room temperature, dichloromethane (100 mL) was added and the mixture was washed with saturated aqueous sodium hydrogen carbonate solution (100 mL), water (50 mL), brine (50 mL) and dehydrated over anhydrous sodium sulfate. The dichloromethane-pyridine solution was concentrated under reduced pressure. To the obtained brown solid was added dichloromethane (30 mL) and the mixture was filtered. The soluble part was concentrated again and purified by silica gel column chromatography (hexane:tetrahydrofuran=14:1-7:1) to give the object DMTr-d$T^{CO\text{-}TOP}$-TBDMS (2.21 g, 1.41 mmol, 28.3%) as a white solid. $^1H$ NMR (400 MHZ, $CDCl_3$) δ: −0.03 (s, 3H, $Si^tBu(CH_3)(CH_3)$), 0.02 (s, 3H, $Si^tBu(CH_3)(CH_3)$), 0.82 (s, 9H, $Si^tBu(CH_3)(CH_3)$), 0.85-0.91 (t, J=6.8 Hz, 9H, octadecyl-$CH_3$), 1.18-1.47 (m, 90H, $OCH_2CH_2(CH_2)_{15}CH_3$), 1.52 (d, J=0.6 Hz, 3H, thymine 5-$CH_3$), 1.72 (quint, J=6.8 Hz, 2H, 4-$OCH_2CH_2(CH_2)_{15}CH_3$), 1.78 (quint, J=6.8 Hz, 4H, 3,5-$OCH_2CH_2(CH_2)_{15}CH_3$), 2.24 (ddd, J=13.6, 6.8, 6.8 Hz, 1H, 2'-CHH), 2.36 (ddd, J=13.6, 5.8, 3.2 Hz, 1H, 2'-CHH), 3.30 (dd, J=10.7, 3.6 Hz, 1H, 5'-CHH); 3.49 (dd, J=10.7, 2.6 Hz, 1H), 3.80 (two singlets, 6H, 4,4'-OMe), 3.98 (t, J=6.5 Hz, 4H, 3,5-$OCH_2CH_2(CH_2)_{15}CH_3$), 4.04 (t, J=6.5 Hz, 2H, 3,5-$OCH_2CH_2(CH_2)_{15}CH_3$), 3.95-4.05 (probably m, 1H), 4.51 (m, 1H), 6.33 (m, 1H), 6.84 (d, 1.2 Hz, 2H), 6.84-6.87 (m, 4H), 7.13 (s, 2H); 7.24-7.271 (m, 1H), 7.28-7.33 (m, 6H), 7.41 (d, J=7.2 Hz, 2H); 7.76 (s, 1H).

Example 14: Synthesis of 5'-O-(4,4'-dimethoxytrityl)deoxythymidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-deoxythymidine 3'-[O-(2-cyanoethyl)]phosphorothionyl-$N^2$-isobutyryldeoxyguanosine 3'-[O-(2-cyanoethyl)]phosphorothionyl-$N^3$-[3,4,5-tris(octadecyloxy)benzoyl]-3'-tert-butyldimethylsilyldeoxythymidine (DMTr-d[$TC^{Bz}C^{Bz}C^{Bz}G^{iBu}C^{Bz}C^{Bz}TG^{iBU}T^{CO\text{-}TOP}$] (SEQ ID NO: 1)-TBDMS)

DMTr-$dT^{CO\text{-}TOP}$-TBDMS obtained in Example 13 was elongated in the same manner as in Example 9 to give the object 10 mer.

The yield of each step is shown below.

TABLE 3

| monomer | resultant product | yield (%) |
|---|---|---|
| 5'-(4,4'-dimethoxytrityl)-$N^2$, isobutyryl-2'-deoxyguanosine-3'-[(2-cyanoethyl)-N,N-diisopropyl]phosphoramidite | DMTr-d[$G^{iBu}T^{CO\cdot TOP}$]-TBDMS | 100 |
| 5'-(4,4'-dimethoxytrityl)-2'-deoxythymidine-3'-[(2-cyanoethyl)-N,N-diisopropyl]phosphoramidite | DMTr-d[$TG^{iBu}T^{CO\cdot TOP}$]-TBDMS | 100 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}TG^{iBu}T^{CO\cdot TOP}$]-TBDMS | 99.1 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}C^{Bz}TG^{iBu}T^{CO\cdot TOP}$]-TBDMS | 100 |
| 5'-(4,4'-dimethoxytrityl)-$N^2$-isobutyryl-2'-deoxyguanosine-3'-[(2-cyanoethyl)-N,N-diisopropyl]phosphoramidite | DMTr-d[$G^{iBu}C^{Bz}C^{Bz}TG^{iBu}T^{CO\cdot TOP}$]-TBDMS | 90.5 |
| 5'-(4,4'dimethoxytrityl)-$N^4$-benzoyl-2'-deoxycytidine-3'-[(2-cyanoethyl)-N,N-diisopropyl]phosphoramidite | DMTr-d[$C^{Bz}G^{iBu}C^{Bz}C^{Bz}TG^{iBu}T^{CO\cdot TOP}$]-TBDMS | 98.1 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}C^{Bz}G^{iBu}C^{Bz}C^{Bz}TG^{iBu}T^{CO\cdot TOP}$]-TBDMS | 96.1 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}C^{Bz}C^{Bz}G^{iBu}C^{Bz}C^{Bz}TG^{iBu}T^{CO\cdot TOP}$]-TBDMS | 96.7 |
| 5'-(4,4'-dimethoxytrityl)-2'-deoxythymidine-3'-[(2-cyanoethyl)-N,N-diisopropyl]phosphoramidite | DMTr-d[$TC^{Bz}C^{Bz}C^{Bz}G^{iBu}C^{Bz}C^{Bz}TG^{iBu}T^{CO\cdot TOP}$] (SEQ ID NO: 1)-TBDMS | 97.1 |

Example 15: Desilylation of DMTr-d[TC$^{Bz}$C$^{Bz}$C$^{Bz}$G$^{iBu}$C$^{Bz}$C$^{Bz}$TG$^{iBU}$T$^{CO-TOP}$]-TBDMS (1) Desilylation at the Same Fluoride Ion Concentration and Temperature Raising Conditions as in Example 10

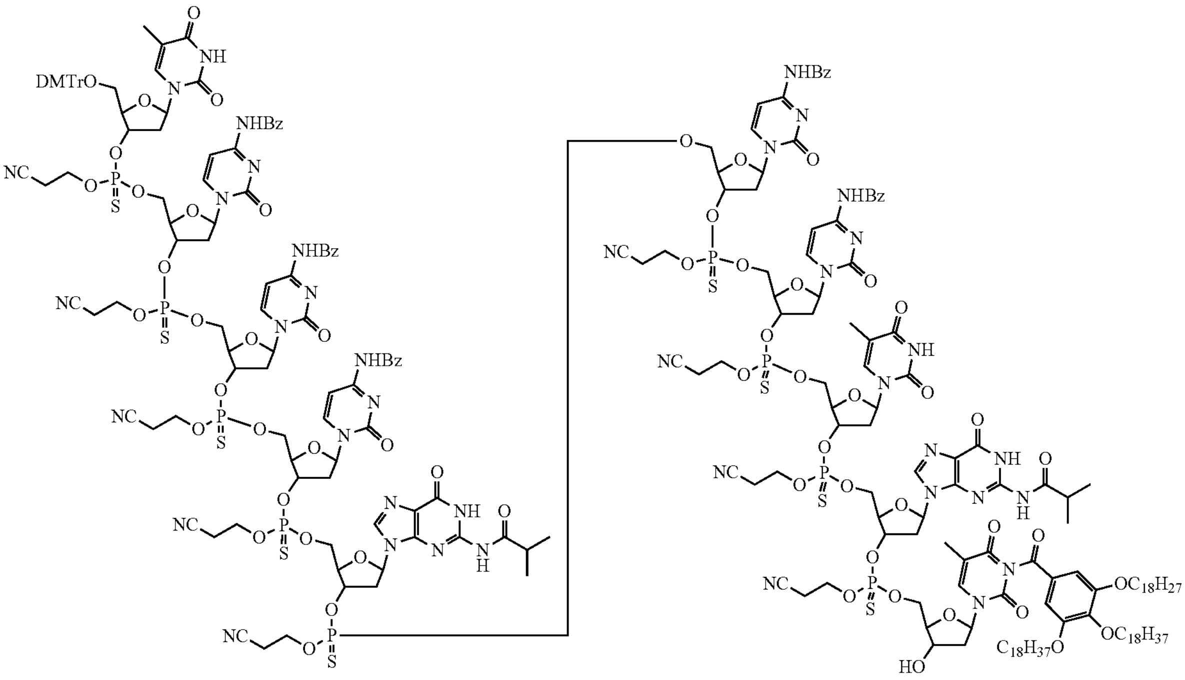

A mixture (0.141 g, 0.0199 mmol) of DMTr-d[TC$^{Bz}$C$^{Bz}$C$^{Bz}$G$^{iBu}$C$^{Bz}$C$^{Bz}$TG$^{iBu}$TG$^{iBu}$T$^{CO-TOP}$]-TBDMS obtained in Example 14 and 3,4,5-tris(octadecyloxy)benzylacetate at a molar ratio of 1.00:1.60 was dissolved in dichloromethane (0.6 mL) and the mixture was cooled to 20° C. Thereto was added a solution of triethylamine trihydrofluoride (16.7 μL, 0.100 mmol), pyridine (32.3 μL, 0.40 mmol) in tetrahydrofuran (1.2 mL) and they were mixed. The reaction was progressed at 20° C. for 24 hr to find that desilylation was not completed.

(2) Conditions that Improved Fluoride Ion Concentration

A mixture (0.350 g, 0.0493 mmol) of DMTr-d[TC$^{Bz}$C$^{Bz}$C$^{Bz}$G$^{iBu}$C$^{Bz}$C$^{Bz}$TG$^{iBu}$T$^{CO-TOP}$]-TBDMS obtained in Example 14 and 3,4,5-tris(octadecyloxy)benzylacetate at a molar ratio of 1.00:1.60 was dissolved in dichloromethane (1.5 mL) and the mixture was cooled to 20° C. Thereto was added a solution of triethylamine trihydrofluoride (0.167 mb, 1.00 mmol), pyridine (0.324 mL, 4.01 mmol) in tetrahydrofuran (3.0 mL). The reaction mixture was stirred at 20° C. for 24 hr and completion of desilylation was confirmed by LC/MS. To the reaction mixture was added acetonitrile (18 mL) to precipitate a mixture of the object DMTr-d[TC$^{Bz}$C$^{Bz}$C$^{Bz}$G$^{iBu}$C$^{Bz}$C$^{Bz}$TG$^{iBu}$T$^{CO-TOP}$]-OH and 3,4,5-tris(octadecyloxy)benzylacetate. The solid was obtained by filtration using a hirsch funnel, washed with acetonitrile and dried in vacuo to give a white solid (0.216 g, of which oligonucleic acid was 0.168 g, 0.310 mmol, 62.8% yield).

The sample was dissolved in tetrahydrofuran, the cyanoethyl-protecting group on phosphoric acid was made to fall off with DBU, and the object product was identified by LC/MS. Analysis by HPLC showed a peak of short chain in the subsequent retention time of the object compound, and the area ratio of the peak of the object compound was 62.0%.

Example 16: Synthesis of 5'-O-(4,4'-dimethoxytrityl)-N$^{4}$-[3,4,5-tris(octadecyloxy)benzyl]succinyl-3'-O-(tert-butyldimethylsilyl)deoxycytidine (DMTr-dC$^{suc-TOB}$-TBDMS)

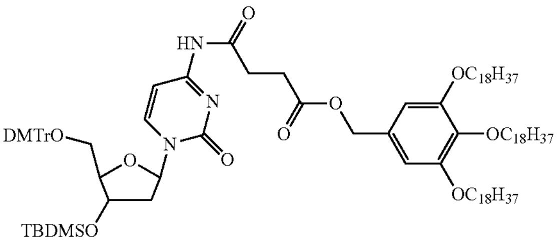

3,4,5-Tris (octadecyloxy)benzylsuccinate triethylammonium salt (1.11 g, 1.0 mmol) was dissolved in dehydrated chloroform (3.3 mL). Thereto was added diisopropylethylamine (0.512 mL, 3.00 mmol) and 2-(1H benzotriazol-1-yl)-1,1,3,3-tetramethyluroniumhexafluorophosphate (HBTU) (0.759 g, 2.00 mmol) was added at 0° C. The reaction mixture was stirred at room temperature for 30 min, 3'-O-(tert-butyldimethylsilyl)-5'-O-(4,4'-dimethoxytrityl)-2'-deoxycytidine (0.966 g, 1.50 mmol) was added and the mixture was stirred at 40° C. for 17 hr. Completion of the reaction was confirmed by thin layer chromatography, and the mixture was cooled to room temperature. To the reaction mixture was added acetonitrile (5 mL) and the object product was precipitated and filtered. The obtained cake was washed with 5 mL of acetonitrile and dried in vacuo to give the object product (1.64 g, 1.00 mmol, 100%).

$^1$H NMR (400 MHZ, $CDCl_3$) δ: −0.06 (s, 3H, Si—$CH_3$), 0.00 (s, 3H, Si—$CH_3$), 0.81 (s, 9H, $^t$Bu), 0.88 (t, J=6.8 Hz, 9H, $OCH_2CH_2(CH_2)_{15}CH_3$), 1.2-1.5 (m, 90H, $OCH_2CH_2(CH_2)_{15}CH_3$), 1.73 (quint, J=8.0 Hz, 2H, 4-$OCH_2CH_2(CH_2)_{15}CH_3$), 1.78 (quint, J=8.0 Hz, 4H, 2,5-$OCH_2CH_2(CH_2)_{15}CH_3$), 2.19 (ddd, J=13.6, 6.0, 4.4 Hz, 2'-CHH), 2.55 (ddd, J=13.6, 6.4, 6.4, 2'-CHH), 2.68-2.75 (m, 4H, —$COCH_2CH_2CO$—), 3.32 (dd, J=10.8, 3.2 Hz, 1H, 5'-CHH), 3.52 (dd, J=10.8, 2.8 Hz, 1H, 5'-CHH), 3.79 (s, 6H, $OCH_3$ Of DMTr), 3.91-3.97 (m, 4H, —$OCH_2(CH_2)_{16}CH_3$), 4.00 (ddd, J=5.6, 3.2, 2.8 Hz, 1H, 4'-H), 4.42 (ddd, J=6.4, 6.0, 5.6 Hz, 1H, 3'-H), 5.02 (s, 2H, suc-$OCH_2Ar$), 6.22 (dd, J=6.4, 4.4 Hz, 1H, 1'-H), 6.54 (s, 2H, 2,6-H of tri(octadecyloxy)phenyl), 6.84 (d, J=8.8 Hz, 4H, 3,5-H of methoxyphenyl), 7.06 (d, 7.2 Hz, 1H, 6H of cytosine), 7.20-7.30 (m, 7H, Ar), 7.38 (d, J=7.2 Hz, 2H, 2,6-of phenyl), 8.19 (brs, 1H, N—H), 8.37 (d, J=7.2 Hz, 5-H of cytosine).

Example 17: Synthesis of 5'-O-(4,4'-dimethoxytrityl)-deoxythymidine 3'-[O-(2-cyanoethyl)]phosphorothionyl-N$^2$-isobutyryl-deoxyguanosine 3'-[O-(2-cyanoethyl)]phosphorothionyl-N$^4$-[3,4,5-tris(octadecyloxy)benzyl]succinyl-3'-tert-butyldimethylsilyldeoxycytidine (DMTr-d[TG$^{iBu}$C$^{suc\text{-}TOB}$]-TBDMS)

(1) Synthesis of 5'-O-(4,4'-dimethoxytrityl)-N$^2$-isobutyryl-deoxyguanosine 3'-[O-(2-cyanoethyl)]phosphorothionyl-N$^4$-[3,4,5-tris(octadecyloxy)benzyl] succinyl-3'-tert-butyldimethylsilyldeoxycytidine (DMTr-d[G$^{iBu}$C$^{suc\text{-}TOB}$]-TBMDS)

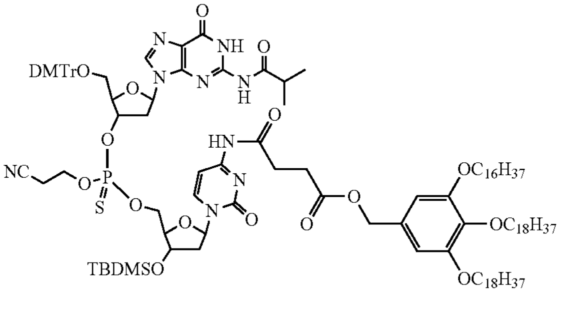

Under an argon atmosphere, DMTr-dC$^{suc\text{-}TOB}$-TBDMS (820 mg, 0.500 mmol) obtained in Example 16 was dissolved in dehydrated dichloromethane (23 mL), 5-methoxyindole (1.47 g, 10.0 mmol), trifluoroacetic acid (55.7 μL, 0.750 mmol) were added, the mixture was stirred at room temperature for 30 min, and completion of the reaction was confirmed by UPLC. The reaction mixture was neutralized with 2,4,6,-trimethylpyridine, a solution of 5'-O-(4,4'-dimethoxytrityl)-N$^2$butyryl-deoxyguanosine-3'-[O-(2-cyanoethyl) (N,N-diisopropyl)]phosphoramidite (1.88 g, 2.24 mmol), 5-(benzylthio)-1H-tetrazole (0.432 g, 2.25 mmol) in acetonitrile (3.00 mb) was added, and the mixture was stirred at room temperature for 2 hr. 3-[(N,N-dimethylaminomethylidene)amino]-3H-1,2,4-dithiazole-5-thione (0.620 g, 3.02 mmol) was added, and the mixture was stirred at room temperature for 45 min to sulfurate_phosphite intermediate. Acetonitrile (120 mL) was added at room temperature to precipitate the object compound. The reaction mixture was filtered using a hirsch funnel, washed with acetonitrile and dried in vacuo to give the object DMTr-d[G$^{iBu}$C$^{suc\text{-}TOB}$]-TBMDS (1.00 g, 0,471 mmol, 94%) as a white solid, The sample was dissolved in tetrahydrofuran, the cyanoethyl-protecting group on phosphoric acid was made to fall off with DBU, and the object product was identified by LC/MS. LC/MS m/z: calcd 2052.26, found 2052.26 [M-H]$^-$.

(2) Synthesis of 5'-O-(4,4'-dimethoxytrityl)-deoxythymidine 3'-[O-(2-cyanoethyl)]phosphorothionyl-N$^2$-isobutyryl-deoxyguanosine 3'-[O-(2-cyanoethyl)] phosphorothionyl-N$^4$-[3,4,5-tris(octadecyloxy) benzyl]succinyl-3'-tert-butyldimethylsilyldeoxycytidine (DMTr-d [TG$^{iBu}$C$^{suc\text{-}TOB}$]-TBDMS)

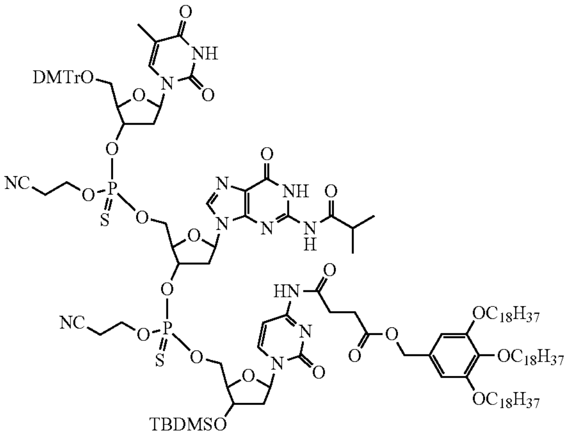

Under an argon atmosphere, DMTr-d[G$^{iBu}$C$^{suc\text{-}TOB}$]-TBMDS (974 is mg, 0.458 mmol) obtained in (1) was dissolved in dehydrated dichloromethane (23 mL), 5-methoxyindole (1.47 g, 10.0 mmol), trifluoroacetic acid (47.6 μL, 0.750 mmol) were added, the mixture was stirred at room temperature for 30 min, and completion of the reaction was confirmed by LC/MS. The reaction mixture was neutralized with 2,4,6,-trimethylpyridine (325 μL, 2.45 mmol), a solution of 5'-O-(4,4'-dimethoxytrityl)-thymidine-3'-[O-(2-cyanoethyl) (N,N-diisopropyl)]phosphoramidite (1.02 g, 1.37 mmol), 5-(benzylthio)-1H-tetrazole (0.264 g, 1.37 mmol) in acetonitrile (3.00 mL) was added, and the mixture was stirred at room temperature for 2 hr. Completion of the reaction was confirmed by LC/MS, after which 3-[(N,N-dimethylaminomethylidene)amino]-3H-1,2,4-dithiazole-5-thione (0.311 g, 1.51 mmol) was added, and the mixture was stirred at room temperature for 45 min to sulfurate_phosphite intermediate. Acetonitrile (120 mL) was added at room temperature to precipitate the object compound. The reaction mixture was filtered using a hirsch funnel, washed with acetonitrile and dried in vacuo to give the object DMTr-d[TG$^{iBu}$C$^{suc\text{-}TOB}$]-TBDMS (1.05 g, 0.419 mmol, 92%) as a white solid.

The sample was dissolved in tetrahydrofuran, the cyanoethyl-protecting group on phosphoric acid was made to fall off with DBU, and the object product was identified by LC/MS. LC/MS m/z: calcd 1185.64, found 1185.64 $[M-2H]^{2-}$.

Example 18-1: Synthesis of 5'-O-(4,4'-dimethoxytrityl)-deoxythymidine 3'-[O-(2-cyanoethyl)]phosphorothionyl-$N^2$-isobutyryl-deoxyguanosine 3'-[O-(2-cyanoethyl)]phosphorothionyl-$N^4$-[3,4,5-tris(octadecyloxy)benzyl]succinyldeoxycytidine (DMTr-d[$TG^{iBu}C^{suc\text{-}TOB}$]-H) (desilylation)

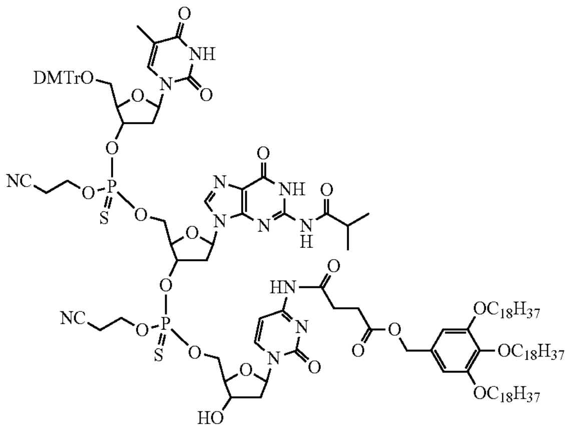

DMTr-d[$TG^{iBu}C^{suc\text{-}TOB}$]-TBDMS (0.748 g, 0.301 mmol) obtained in Example 17 was dissolved in dichloromethane (9.0 ml) and the mixture was cooled to 15° C. Thereto was added a solution of trimethylamine trihydrofluoride (875 mg, 5.42 mmol), pyridine (1.75 mL, 22.1 mmol) in tetrahydrofuran (18.0 mb), and the mixture was stirred at 15° C. for 30 hr. To the reaction mixture was added acetonitrile (108 mL) to allow for precipitation, and the precipitate was filtered using a hirsch funnel, washed and dried in vacuo to give the object DMTr-d[$TG^{iBu}C^{suc\text{-}TOB}$]-H (0.686 g, 2.29 mmol, 96.6%).

The sample was dissolved in tetrahydrofuran, the as cyanoethyl-protecting group on phosphoric acid was made to fall off with DBU, and the object product was identified by LC/MS. LC/MS m/z: calcd 2258.20, found 2258.21 $[M-H]^-$.

Example 18-2: Synthesis of 5'-O-(4,4'-dimethoxytrityl)-deoxythymidine 3'-[O-(2-cyanoethyl)]phosphorothionyl-$N^2$-isobutyryldeoxyguanosine-3'-[O-(2-cyanoethyl)]phosphorothionyl-$N^4$-[3,4,5-tris(octadecyloxy)benzyl]succinyldeoxycytidine-3'-yl-[O-(2-cyanoethyl)]-N,N-diisopropylphosphoramidite (DMTr-d[$TG^{iBu}C^{suc\text{-}TOB}$]-PA)

DMTr-d[$TG^{iBu}C^{suc\text{-}TOB}$] obtained in Example 18-1 was phosphitylated in the same manner as in Example 6-(5) to give DMTr-d[$TG^{iBu}C^{suc\text{-}TOB}$]-PA.

Example 19: Synthesis of 5'-O-(4,4'-dimethoxytrityl)-deoxythymidine-3'-[O-(2-cyanoethyl)]phosphorothionyl-$N^2$-isobutyryldeoxyguanosine-3'-[O-(2-cyanoethyl)]phosphorothionyl-$N^4$-[3,4,5-tris(octadecyloxy)benzyl]succinyldeoxycytidin-3'-yl-[O-(2-cyanoethyl)]phosphorothionyl-$N^4$-benzoyldeoxyadenosine 3'-[O-(2-cyanoethyl)]phosphorothionyl-deoxythymidine 3'-[O-(2-cyanoethyl)]phosphorothionyl-deoxythymidin-3'-yl-3,4,5-tris(octadecyloxy)benzylsuccinate (DMTr-d[$TG^{iBu}C^{suc\text{-}TOB}A^{Bz}TT$]-suc-TOB) by Condensation of 5'-O-(4,4'-dimethoxytrityl)-deoxythymidine 3'-[O-(2-cyanoethyl)]phosphorothionyl-$N^2$-isobutyryldeoxyguanosine-3'-[O-(2-cyanoethyl)]phosphorothionyl-$N^4$-[3,4,5-tris(octadecyloxy)benzyl]succinyldeoxycytidin-3'-yl-[O-(2-cyanoethyl)]-N,N-diisopropylphosphoramidite (DMTr-d[$TG^{iBu}C^{suc\text{-}TOB}$]-PA) and $N^4$-benzoyldeoxyadenosine 3'-[O-(2-cyanoethyl)]phosphorothionyl-deoxythymidine 3'-[O-(2-cyanoethyl)]phosphorothionyl-deoxythymidin-3'-yl-3,4,5-tris(octadecyloxy)benzylsuccinate

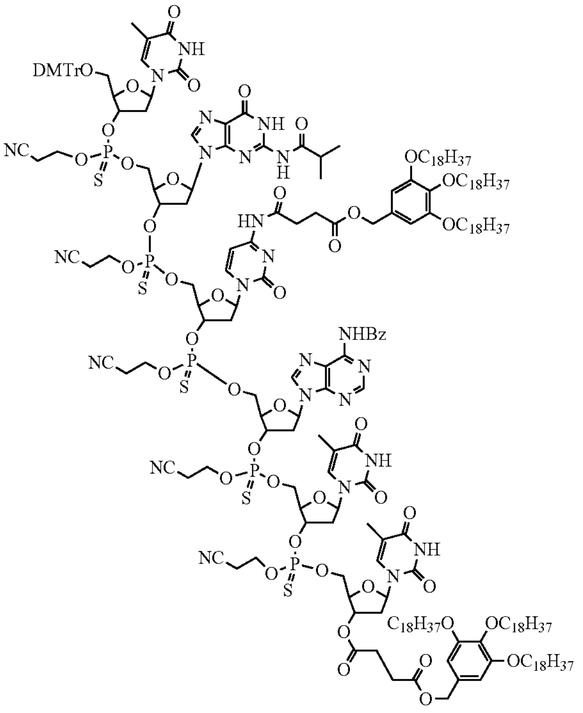

DMTr-d[$TG^{iBu}$(suc-TOB]-PA (0.156 g, 0.0606 mmol) obtained in Example 18-2 and d[$A^{Bz}TT$]-suc-TOB (0,103 g, 0,492 mmol) obtained in Preparation Example 1-(3) were dissolved in dichloromethane (5.0 mb), and the mixture was dehydrated by molecular sieve 3A (0.229 g), The solution (4.5 mL) was filtered through a 0.45 μm membrane filter. To the filtered solution was added 5-(benzylthio)-1H-tetrazole (20.5 mg, 0.107 mmol) and the mixture was stirred at room temperature for 1 hr 30 min. Completion of condensation was confirmed by LC/MS, after which pyridine (48.5 μL, 0.600 mmol) and then 3-[(N,N-dimethylaminomethylidene)amino]-3H-1,2,4-dithiazole-5-thione (0.311 g, 1.51 mmol) were added, and the mixture was stirred at room temperature for 30 min to sulfurate phosphite intermediate. To the reaction mixture was added methanol (20 mL) to precipitate the object product, and the object product was filtered using a hirsch funnel and washed to give a solid (0.221 g) containing the object product.

The sample was dissolved in tetrahydrofuran, the cyanoethyl-protecting group on phosphoric acid was made to fall off with DBU, and the object product was identified by LC/MS. LC/MS m/z: calcd 1441.40, found 1441.40 $[M-3H]^{3-}$.

Example 20: Comparison of Deprotection of 6-Mer Oligonucleic Acid DMTr-d[$TG^{iBu}C^{suc\text{-}TOB}A^{Bz}TT$]-suc-TOB and DMTr-d[$TG^{iBu}C^{CO\text{-}TOP}A^{Bz}TT$]-suc-TOB, which are Produced by Fragment Condensation, in Aqueous Ammonia

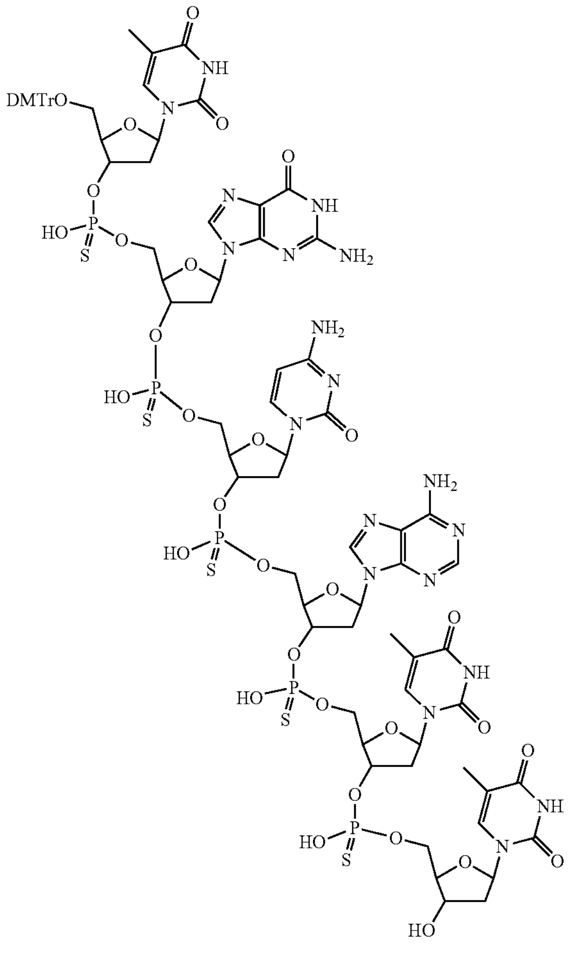

(1) Deprotection of DMTr-d[$TG^{iBu}C^{suc\text{-}TOP}A^{Bz}TT$]-suc-TOB

The resultant product (6.05 mg) of Example 19 was dispersed in 1.5 ml of aqueous ammonia. The dispersion solution was stirred at 23° C. with a magnetic stirrer. The reaction mixture was sampled every 2 hr up to 12 hr and every 12 hr thereafter and analyzed by LC/MS In the resultant product of Example 19, dissociation of cyanoethyl group, acetyl group, benzoyl group, succinyl group was completed within 2 hr and a part of isobutyryl group remained. The deprotection of isobutyryl group was completed in 36 hr.

(2) Deprotection of DMTr-d[$TG^{iBu}C^{CO\text{-}TOP}A^{Bz}TT$]-suc-TOB

The resultant product (6.01 mg) of Example 7 was dispersed in 1.5 mL of aqueous ammonia. The dispersion solution was stirred at 23° C. with a magnetic stirrer. The reaction mixture was sampled every 2 hr up to 12 hr and every 12 hr thereafter and analyzed by LC/MS.

In the resultant product of Example 7, dissociation of cyanoethyl group, acetyl group, benzoyl group, succinyl group was completed within 2 hr and a part of 3,4,5-tris (octadecyloxy)benzoyl group and isobutyryl group remained. A part of 3,4,5-tris(octadecyloxy)benzoyl group still remained even at the time point of 12 hr and complete dissociation was confirmed at 24 hr. The deprotection of isobutyryl group was completed in 36 hr.

Example 21: Diamidite Activation and Phosphitylation Using 4,5-dichloroimidazole (1) Determination of pKa by titration of 4,5-dichloroimidazole 4,5-Dichloroimidazole (0.2396 g, 1.749 mmol) was dissolved in ion exchange water deaerated by boiling to 50.0 mL (0.0350 M). This solution (20 mL) was titrated at 25° C. with 0.10 M NaOH.

By non-log linearization plot of titration results (Benet, L. Z.; Goyan, J. E. J. Pharm. Sci. 1967, 56, 665-680.), pKa of dichloroimidazole in water at 25° C. was determined to be 9.09.

(2) Diamidite Activation and Phosphitylation Using 4,5-Dichloroimidazole

2-Cyanoethyl-N,N,N',N'-tetraisopropylphosphordiamidite (0.120 g, 0.40 mmol) was dissolved in dry toluene: cyclohexane=1:1 (v/v) solvent (1.5 mL). Thereto was added 4,5-dichloroimidazole (0.138 g, 1.00 mmol) and the mixture was stirred at under dry argon for 17 hr to prepare a solution containing a phosphitylating agent. The total amount of this solution was filtered through a 0.45 μm membrane filter. N-methylmorpholine (0.881 mL, 8.0 mmol) was added to the filtrate, a mixture of DMTY-d[$TG^{iBu}C^{CO\text{-}TOP}$]-H (0.229 g, 0.100 mmol) obtained in the same manner as in Example 6-(1) and $MeOCOC_6H_2(OC_{18}H_{37})_3$ (0.162 g) and N-methylimidazole (0.040 mL, 0.50 mmol) were added at 15° C. to give a suspension. Dichloromethane (10.0 mL) was added at the same temperature to give a uniform solution and the solution was stirred for 43 hr. After cooling to 0° C., 2,4,6-trimethylpyridine (0.53 mL, 4.9 mmol) was added, and acetonitrile (60 mL) was added to precipitate the resultant product. The precipitate was filtered using a hirsch funnel, washed and dried in vacuo to give a white solid (0.386 g) containing DMTr-d[$TG^{iBu}C^{CO\text{-}TOP}$]-$P(N^iPr_2)(OCH_2CH_2CN)$. As a result of analysis by $^{31}P\{^1H\}$NMR, an amidite introduction rate into the 3'-terminal was 50%. A decyanoethylated form on phosphoric acid of internucleotide was not observed.

Example 22: Synthesis of 5'-O-(4,4'-dimethoxytrityl)-deoxythymidine 3'-[O-(2-cyanoethyl)]phosphorothionyl-$N^2$-isobutyryldeoxyguanosine 3'-[O-(2-cyanoethyl)]phosphorothionyl-$N^4$-[3,4,5-tris (octadecyloxy)benzoyl]-3'-isopropoxydiisopropylsilyldeoxycytidine (DMTr-d [$TG^{iBu}C^{CO\text{-}TOP}$]-IPODIPS)

(1) Synthesis of Isopropoxydiisopropylsilane

Under a dry argon atmosphere, imidazole (3.27 g, 48.1 mmol) was dissolved in dry N,N-dimethylformamide (40 mL). Thereto were added dropwise 2-propanol (3.70 mL, 52.2 mmol) and diisopropylchlorosilane (4.00 mL, 23.4 mL). The mixture was stirred at 40° C. for 11 hr. The reaction mixture was cooled to room temperature, hexane (40 mL) was added, and saturated aqueous sodium hydrogen carbonate solution (20 mL) and ion exchange water (20 mL) were successively added, and the mixture was stirred until development of air foams ceased. The hexane phase was separated, washed successively with water (40 mL), saturated brine (40 mL) and dried over anhydrous sodium sulfate. The solvent was evaporated by a rotary evaporator (100 mmHg, water bath 35° C.) to give isopropoxydiisopropylsilane (2.69 g) as a colorless transparent liquid. The resultant product was used without purification in the next step.

(2) Synthesis of 5'-O-(4,4'-dimethoxytrityl)-3'-O-(isopropoxydiisopropylsilyl)deoxycytidine Isopropoxydiisopropylsilane (1.40 g, 8.01 mmol) obtained in (1) was dissolved in dry dichloromethane (8.0 mL), and molecular sieve 3A (0.1 g) activated under heating was added. After dehydrating, the solution was filtered. Dichloromethane (20 mL) was further added. To the solution was added 1,3-dichloro-5,5-dimethylhydantoin (1.58 g, 8.00 mmol), and the mixture was stirred at room temperature for 1 hr. Pyridine (0.65 mL, 8.03 mmol), 5'-(4,4'-dimethoxytrityl) thymidine (2.18 g, 4.00 mmol), imidazole (2.74 g, 40.2 mmol) were added and the mixture was stirred at room temperature for 5 hr. To the reaction mixture was added saturated aqueous sodium thiosulfate solution (40 mL) to quench the reaction, and the mixture was partitioned. The organic layer was washed with water and then saturated brine, and further washed with aqueous sodium hydrogen carbonate solution. The organic layer was dehydrated over sodium sulfate, and the solvent was evaporated under reduced pressure to give a yellow solid (3.45 g) containing the title compound. This was used without purification in the next step.

(3) Synthesis of $N^4$-[3,4,5-tris(octadecyloxy)benzoyl]-5'-O-(4,4'-dimethoxytrityl)-3'-O-(isopropoxydiisopropylsilyl)deoxycytidine 5'-O-(4,4'-dimethoxytrityl)-3'-O-(isopropoxydiisopropylsilyl) deoxycytidine obtained in (2) was subjected together with 3,4,5-tris(octadecyloxy)benzoic acid (1.85 g, 2.00 mmol) to condensation conditions similar to those in Example 1-(2) to give a pale-yellow solid (2.57 g) containing the title compound. This was purified by silica gel column chromatography (hexane:ethyl acetate=5:1-3:1) to give the title compound (1.20 g, 0.744 mmol, 37% yield). $^1H$ NMR (400 MHZ, $CDCl_3$) δ: 0.88 (t, J=6.8 Hz, 9H, $O(CH_2)_{17}CH_3$), 0.94-1.00 (m, 12H, $SiCH(CH_3)_2$), 1.11 (d, J=6.4 Hz, 2H, $—OCH(CH_3)(CH_3)$), 1.13 (d, J=6.4 Hz, 2H, $—OCH(CH_3)(CH_3)$), 1.20-1.50 (m, 92H, $OCH_2CH_2(CH_2)_{15}CH_3$ and $SiCH(CH_3)_2$), 1.74 (quint, J=6.8 Hz, 2H, 4-$OCH_2CH_2(CH)_2CH_3$), 1.85 (quint, J=6.8 Hz, 4H, 3,5-$OCH_2CH_2(CH)_{15}CH_3$), 2.22 (ddd, J=13.6, 6.0, 4.8 Hz, 1H, 2'-CHH), 2.70 (ddd, J=13.6, 6.4, 6.4 Hz, 1H, 2'-CHH), 3.35 (dd, J=10.8, 3.6 Hz, 1H, 5'-CHH), 3.51 (dd, J=10.8, 2.8 Hz, 1H, 5'-CHH), 3.798 (s, 3H, DMTr 4-$OCH_3$), 3.803 (s, 3H, DMTr 4'-$OCH_3$), 3.99-4.04 (m, 6H, 3'-H and $OCH_2(CH_2)_{16}CH_3$), 4.09 (sep, J=6.0 Hz, 1H, $OCHMe_2$), 4.65 (ddd, J=6.4, 6.0, 6.0, 1H, 4'-H), 6.32 (dd, J=6.0, 6.0 Hz, 1H, 1'-H), 6.68 (d, J=9.2 Hz, 4H, 3, 3', 5, 5'-H of p-methoxyphenyl), 7.04 (brs, 2H, 2,6-H of 3,4,5-tris(octadecyloxy) benzoyl), 7.26-7.31 (m, 8H, 2,2',6,6'-H of p-methoxyphenyl, 3,4,5-H of phenyl and 6-H of cytosine), 7.40 (d, J=7.2 Hz, 2H, 2,6-H of phenyl), 8.31 (d, J=7.2 Hz, 1H, 5-H of cytosine), 8.50 (s, 1H, cytosine N—H).

(4) Synthesis of 5'-O-(4,4'-dimethoxytrityl)-deoxythymidine 3'-[O-(2-cyanoethyl)]phosphorothionyl-$N^2$-isobutyryldeoxyguanosine 3'-[O-(2-cyanoethyl)] phosphorothionyl-$N^4$-[3,4,5-tris(octadecyloxy) benzoyl]-3'-isopropoxydiisopropylsilyldeoxycytidine (DMTr-d[$TG^{iBu}C^{CO-TOP}$]-IPODIPS)

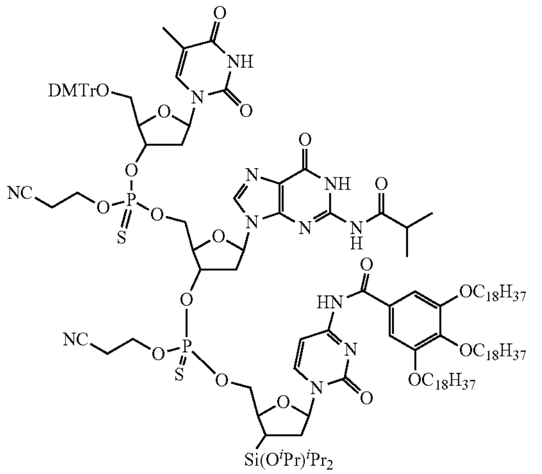

$N^4$-[3,4,5-tris(octadecyloxy)benzoyl]-5'-O-(4,4'-dimethoxytrityl)-3'-O-(isopropoxydiisopropylsilyl)deoxycytidine obtained in (3) as a starting material was elongated in the same manner as in Example 2.

The sample was dissolved in tetrahydrofuran, the cyanoethyl-protecting group on phosphoric acid was made to fall off with DBU, and the object product was identified by LC/MS. LC/MS m/z: calcd 2346.31, found 2346.30 $[M-H]^-$.

Example 23: Comparison of Efficiency of 3'-Silyl Group Deprotection (1) Desilylation of DMTr-d[$TG^{iBu}C^{CO-TOP}$]-IPODIPS DMTr-d[$TG^{iBu}C^{CO-TOP}$]-IPODIPS (0.4915 g, 0.200 mmol) obtained in Example 22 was dissolved in dichloromethane (6.0 ml). A solution of 3HF-TEA (146 mg, 0.906 mmol) and pyridine (146 μL, 1.80 mmol) in THF (12 mb) was added and the mixture was preserved at 15° C. The reaction mixture was sampled and analyzed by HPLC and the progress of 3'-desilylation was tracked. The half-life of the 3'-silyl form was 30 min and the 3'-silyl form was below detection limit in 8 hr.

(2) Desilylation of DMTr-d[$TG^{iBu}C^{CO-TOP}$]-TBDMS

When DMTr-d[$TG^{iBu}C^{CO-TOP}$]-TBDMS obtained in the same manner as in Example 2 was subjected to the same desilylation conditions as in (1), the progress of desilylation was 53% in 8 hr.

Example 24: Synthesis of 5'-O-(4,4'-dimethoxytrityl)deoxythymidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-deoxythymidine 3'-[O-(2-cyanoethyl)]phosphorothionyl-$N^2$-isobutyryldeoxyguanosine 3'-[O-(2-cyanoethyl)]phosphorothionyl-$N^4$-[3,4,5-tris(octadecyloxy)benzoyl]-3'-diisopropylphenylsilyldeoxycytidine (DMTr-d[$TC^{Bz}C^{Bz}C^{Bz}G^{iBu}C^{Bz}C^{Bz}TG^{iBu}C^{CO\text{-}TOP}$] (SEQ ID NO: 4)-DIPPS)

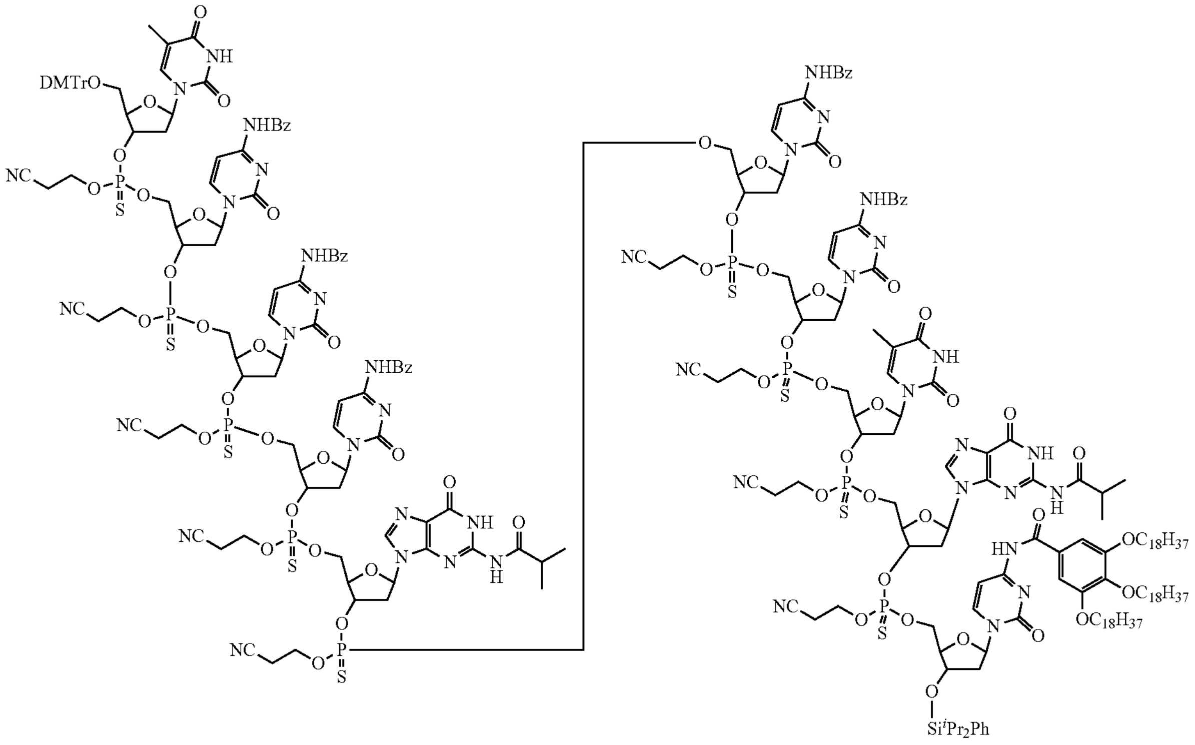

(1) Synthesis of 4-[3,4,5-tris(octadecyloxy)benzoyl]-5'-O-(4,4'-dimethoxytrityl)-3'-O-diisopropylphenylsilyldeoxycytidine (DMTr-d$C^{CO\text{-}TOP}$-DIPPS)

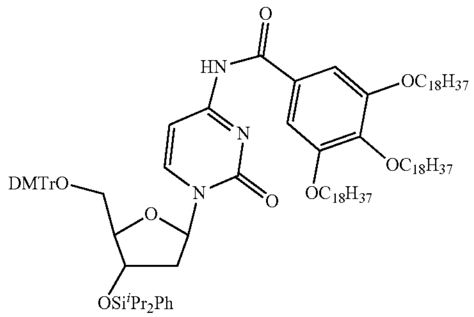

In the same manner as in Example 8-(1), (2), 5'-O-(4,4'-dimethoxytrityl)-3'-O-diisopropylphenylsilyldeoxycytidine was prepared from diisopropylchlorosilane and 5'-O-(4,4'-dimethoxytrityl)deoxycytidine. The resultant product without is purification was subjected to condensation conditions together with 3,4,5-tris(octadecyloxy)benzoic acid in the same manner as in Example 1-(2) to give the title compound as a white solid (yield 43% based on amount used of 3,4,5-tris(octadecyloxy)benzoic acid).

$^1$H NMR (400 MHZ, $CDCl_3$) δ: 0.88 (t, J=6.8 Hz, 9H, $O(CH_2)_{17}CH_3$), 0.95-1.01 (m, 12H, $SiCH(CH_3)_2$), 1.20-1.50 (m, 92H, $OCH_2CH_2(CH_2)_{15}CH_3$ and $SiCH(CH_3)_2$), 1.82 (quint, J=6.8 Hz, 2H, 4-$OCH_2CH_2(CH)_2CH_3$), 1.85 (quint, J=6.8 Hz, 4H, 3,5-$OCH_2CH_2(CH)_{15}CH_3$), 2.18 (ddd, J=13.6, 6.0, 4.8 Hz, 1H, 2'-CHH), 2.76 (m, 1H, 2'-CHH), 3.31 (dd, J=10.8, 3.6 Hz, 1H, 5'-CHH), 3.50 (dd, J=10.8, 2.8 Hz, 1H, 5'-CHH), 3.790 (s, 3H, DMTr 4-$OCH_3$), 3.794 (s, 3H, DMTr 4'-$OCH_3$), 3.99-4.07 (m, 7H, 3'-H and $OCH_2(CH_2)_{16}CH_3$), 4.59 (ddd, J=6.4, 6.0, 6.0, 1H, 4'-H), 6.32 (dd, J=6.0, 6.0 Hz, 1H, 1'-H), 6.80-6.83 (d, J=9.2 Hz, 4H, 3, 3', 5, 5'-H of DMTr), 7.04 (brs, 2H, 2,6-H of 3,4,5-tris(octadecyloxy)benzoyl), 7.22-7.40 (m, 8H, 2, 2', 6, 6'-H of p-methoxyphenyl, 3,4,5-H of phenyl and 6-H of cytosine), 7.46 (dd, J=6.4, 2.0 Hz, 2H, 2,6-H of C-phenyl), 8.29 (d, J=7.2 Hz, 1H, 5-H of cytosine), 8.48 (s, 1H, cytosine N—H).

(2) To DMTr-d$C^{CO\text{-}TOP}$-DIPPS (1.63 g, 1.00 Mmol) Obtained in (1) Was Added Methyl 3,4,5-Tris(Octadecyloxy)Benzoate (1.65 g, 1.75 mmol) and Elongation was Performed in the Same Manner as in Example 9 to Give the Titled Oligonucleic Acid Having 10 Residues

TABLE 4

| monomer | resultant product | yield (%) |
|---|---|---|
| 5'-(4,4-dimethoxytrityl)-$N^2$-isobutyryl-2'-deoxyguanosine-3'-[(2-cyanoethyl)-N,N-diisopropyl]phosphoramidite | DMTr-d[$G^{iBu}C^{CO\cdot TOP}$]-DIPPS | 98 |
| 5'-(4,4'-dimethoxytrityl)-2'-deoxythymidne-3'-[(2-cyanoethyl)-N,N-diisopropyl]phosphoramidite | DMTr-d[$TG^{iBu}C^{CO\cdot TOP}$]-DIPPS | 98 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{BZ}TG^{iBu}C^{CO\cdot TOP}$]-DIPPS | 96 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}C^{BZ}TG^{iBu}C^{CO\cdot TOP}$]-DIPPS | 96 |
| 5'-(4,4'-dimethoxytrityl)-$N^2$-isobutyryl-2'-deoxyguanosine-3'-[(2-cyanoethyl)-N,N-diisopropyl]phosphoramidite | DMTr-d[$G^{iBu}C^{Bz}C^{BZ}TG^{iBu}C^{CO\cdot TOP}$]-DIPPS | 95 |
| 5'-(4,4-dimethoxytrityl)-$N^4$-benzoyl-2'-deoxycytidine-3'-[(2-cyanoethyl)-N,N-diisopropyl]phosphoramidite | DMTr-d[$C^{Bz}G^{iBu}C^{Bz}C^{BZ}TG^{iBu}C^{CO\cdot TOP}$]-DIPPS | 98 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}C^{Bz}G^{iBu}C^{Bz}C^{BZ}TG^{iBu}C^{CO\cdot TOP}$]-DIPPS | 96 |
| 5'-(4,4'-dimethoxytrityl)-$N^4$-benzoyl-2'-deoxycytidine-3'-[(2-cyanoethyl)-N,N-diisopropyl]phosphoramidite | DMTr-d[$C^{Bz}C^{Bz}C^{Bz}G^{iBu}C^{Bz}C^{BZ}TG^{iBu}C^{CO\cdot TOP}$]-DIPPS | 97 |
| 5'-(4,4'-dimethoxytrityl)-2'-deoxythymidine-3'-[(2-cyanoethyl)-N,N-diisopropyl]phosphoramidite | DMTr-d[$TC^{Bz}C^{Bz}C^{Bz}G^{iBu}C^{Bz}C^{BZ}TG^{iBu}C^{CO\cdot TOP}$]-(SEQ ID NO: 4)-DIPPS | 98 |

The sample was dissolved in tetrahydrofuran, the cyanoethyl-protecting group on phosphoric acid was made to fall off with DBU, and the object product was identified by LC/MS. LC/MS m/z: calcd 965.70, found 965.79 $[M-5H]^{5-}$.

Example 25: Synthesis of 5'-O-(4,4'-dimethoxytrityl)deoxythymidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-deoxythymidine 3'-[O-(2-cyanoethyl)]phosphorothionyl-$N^2$-isobutyryldeoxyguanosine 3'-[O-(2-cyanoethyl)]phosphorothionyl-$N^4$-[3,4,5-tris(octadecyloxy)benzoyl]deoxycytidine (DMTr-d[$TC^{Bz}C^{Bz}C^{Bz}G^{iBu}C^{Bz}C^{Bz}TG^{iBu}C^{CO\text{-}TOP}$] (SEQ ID NO: 4)-H) (Desilylation)

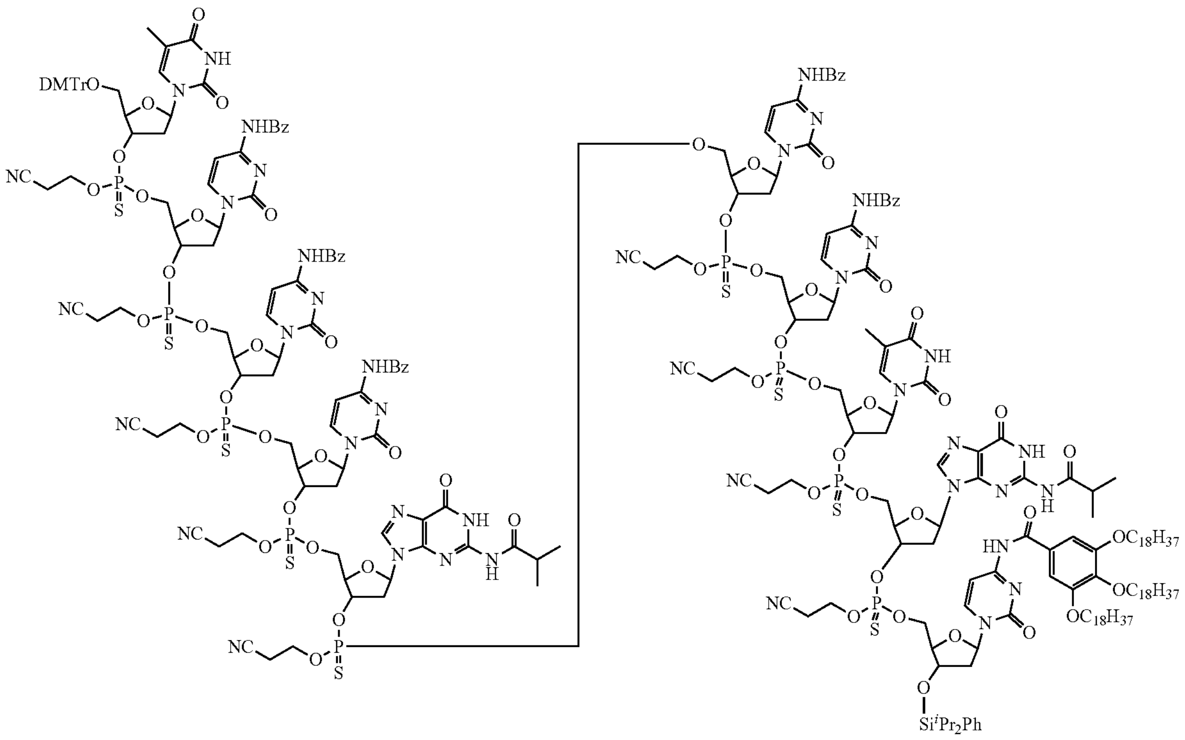

A mixture (4.88 g, 0.70 mmol) of 76 wt % of DMTr-d[$TC^{Bz}C^{Bz}C^{Bz}G^{iBu}C^{Bz}C^{Bz}TG^{iBu}C^{CO\text{-}TOP}$]-DIPPS obtained in Example 24 and methyl 3,4,5-tris(octadecyloxy)benzoate was subjected to the same desilylation conditions as in Example 10 for 26 hr to give a mixture (4.40 g, 0.650 mmol, 93% yield) of methyl 3,4,5-tris(octadecyloxy)benzoate containing the title compound at a content of 75 wt %.

The sample was dissolved in tetrahydrofuran, the cyanoethyl-protecting group on phosphoric acid was made to fall off with DBU, and the object product was identified by LC/MS. LC/MS m/z: calcd 927.68, found 927.68 $[M-5H]^{5-}$.

Example 26: Synthesis of 5'-O-(4,4'-dimethoxytrityl)deoxythymidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-$N^2$-isobutyryldeoxyguanosine 3'-[O-(2-cyanoethyl)]phosphorothionyl-$N^4$-benzoyldeoxycytidine 3'-[O-(2-cyanoethyl)]phosphorothionyl-$N^4$-benzoyldeoxycytidine 3'-[O-(2-cyanoethyl)]phosphorothionyl-deoxythymidine 3'-[O-(2-cyanoethyl)]phosphorothionyl-$N^2$-isobutyryldeoxyguanosine 3'-[O-(2-cyanoethyl)]phosphorothionyl-$N^4$-[3,4,5-tris(octadecyloxy)benzoyl]cytidine-3'-[(2-cyanoethyl)-N,N-diisopropyl]phosphoramidite (DMTr-d[$TC^{Bz}C^{Bz}C^{Bz}G^{iBu}C^{Bz}C^{Bz}TG^{iBu}C^{CO\text{-}TOP}$]-PA)

DMTr-d[$TC^{Bz}C^{Bz}C^{Bz}G^{iBu}C^{Bz}C^{Bz}TG^{iBu}C^{CO\text{-}TOP}$]-H (4.09 g) obtained in Example 25 (content 75.71 wt %, 0.606 mmol) was subjected to the same phosphitylation conditions as in Example 11 to give a white solid (4.10 g) (0.430 mmol, 71% yield) containing the title compound at a content of 56 wt % together with methyl 3,4,5-tris(octadecyloxy)benzoate.

The sample was dissolved in tetrahydrofuran, the cyanoethyl-protecting group on phosphoric acid was made to fall off with DBU, and the object product was identified by LC/MS. Decyanoethylation proceeded only on phosphoric acid between oligonucleotides of the object product, the cyanoethyl group on the 3'-terminal phosphoramidite was retained, and the chemical species in which the phosphorus was oxidized under the ionization condition was observed as the main peak.

LC/MS m/z: calcd 970.90, found 970.85 $[M-5H]^{5-}$.

Preparation Example 2: Synthesis of $N^2$-isobutyryldeoxyguanosine 3'-[O-(2-cyanoethyl)]phosphorothionyl-$N^4$-dimethylaminoethylidenedeoxyadenosine 3'-[O-(2-cyanoethyl)]phosphorothionyl-$N^4$-(2-hexyldecanoyl)deoxycytidine 3'-[O-(2-cyanoethyl)]phosphorothionyl-$N^4$-dimethylaminoethylidenedeoxyadenosine 3'-[O-(2-cyanoethyl)]phosphorothionyl-deoxythymidine 3'-[O-(2-cyanoethyl)]phosphorothionyl-$N^2$-isobutyryldeoxyguanosine 3'-[O-(2-cyanoethyl)]phosphorothionyl-$N^4$-(2-hexyldecanoyl)deoxycytidine 3'-[O-(2-cyanoethyl)]phosphorothionyl-$N^4$-dimethylaminoethylidenedeoxyadenosine 3'-[O-(2-cyanoethyl)]phosphorothionyl-deoxythymidine 3'-[O-(2-cyanoethyl)]phosphorothionyl-deoxythymidin-3'-yl-[3,4,5-tris(octadecyloxy)benzyl]succinate (H-d[$G^{iBu}A^{dma}C^{HO}A^{dma}TG^{iBu}C^{MD}A^{dma}TT$] (SEQ ID NO: 5)-suc-TOB)

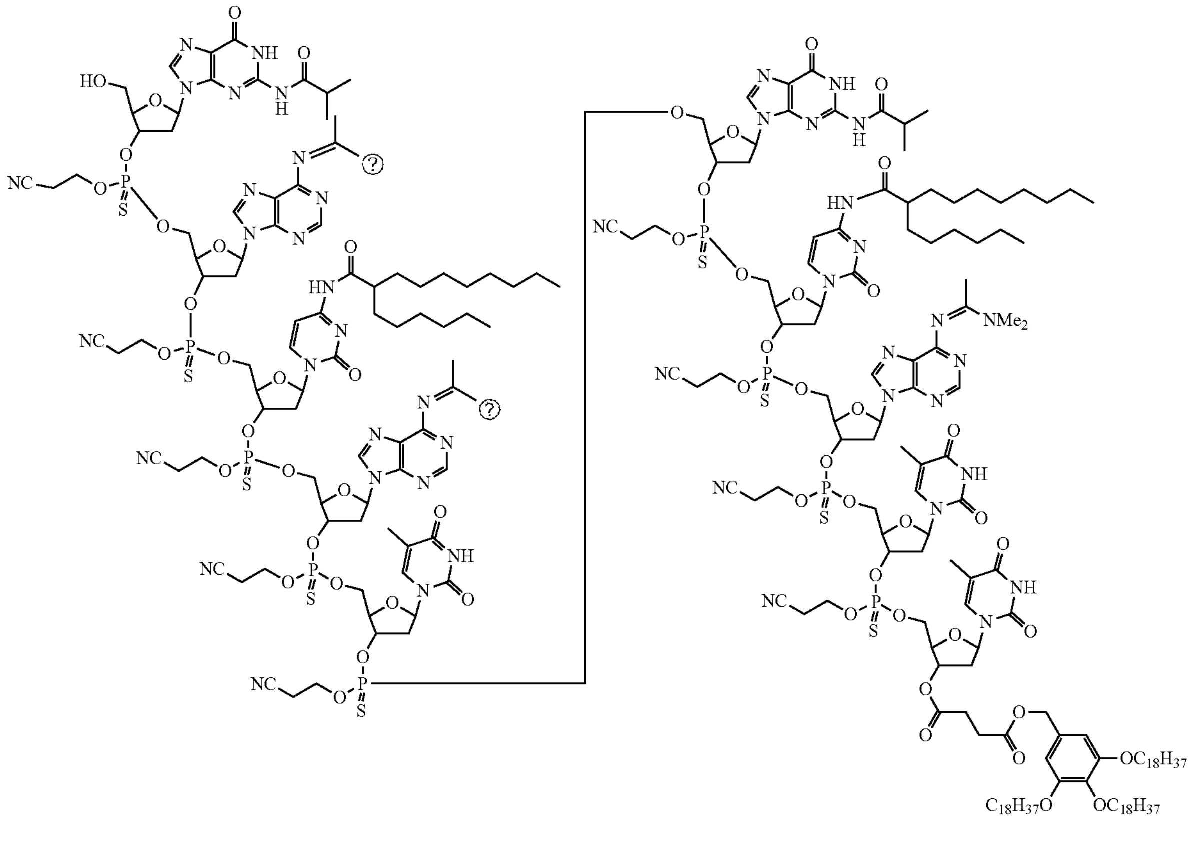

Elongation·de-DMTr-lation of a mixture of 5'-(4,4'-dimethoxytrityl)-deoxythymidin-3'-yl-[3,4,5-tris(octadecyloxy) benzyl]succinate (1.24 g, 0.80 mmol), methyl 3,4,5-tris (octadecyloxy)benzoate (1.23 g, 1.31 mmol) was performed in the same manner as in Preparation Example 1 to give the title compound.

As the nucleoside amidite, the following were used.

- $dA^{dma}$: 5'-(4,4'-dimethoxytrityl)-$N^4$-dimethylaminoethylidene-2'-deoxyadenosine-3'-[(2-cyanoethyl)-N,N-diisopropyl] phosphoramidite
- $dC^{HD}$: 5'-(4,4'-dimethoxytrityl)-$N^4$-(2-hexyldecanoyl)-2'-deoxycytidine-3'-[(2-cyanoethyl)-N,N-diisopropyl] phosphoramidite
- $dG^{iBu}$: 5'-(4,4'-dimethoxytrityl)-$N^2$-isobutyryl-2'-deoxyguanosine-3'-[(2-cyanoethyl)-N,N-diisopropyl] phosphoramidite
- dT: 5'-(4,4'-dimethoxytrityl)-2'-deoxythymidine-3'-[(2-cyanoethyl)-N,N-diisopropyl]phosphoramidite The sample was dissolved in tetrahydrofuran, the cyanoethyl-protecting group on phosphoric acid was made to fall off with DBU, and the object product was identified by LC/MS. LC/MS m/z: calcd 996.58, found 996.54 $[M-5H]^{5-}$.

Example 27: Synthesis of 5'-O-(4,4'-dimethoxytrityl)deoxythymidine 3'-phosphorothionyldeoxycytidine 3'-phosphorothionyldeoxycytidine 3'-phosphorothionyldeoxycytidine 3'-phosphorothionyldeoxyguanosine 3'-phosphorothionyldeoxycytidine 3'-phosphorothionyldeoxycytidine 3'-phosphorothionyldeoxythymidine 3'-phosphorothionyldeoxyguanosine 3'-phosphorothionyldeoxycytidine 3'-phosphorothionyldeoxyguanosine 3'-[phosphorothionyldeoxyadenosine 3'-[phosphorothionyldeoxycytidine 3'-phosphorothionyldeoxyadenosine 3'-phosphorothionyldeoxythymidine 3'-phosphorothionyldeoxyguanosine 3'-phosphorothionyldeoxycytidine 3'-phosphorothionyldeoxyadenosine 3'-phosphorothionyldeoxythymidine 3'-phosphorothionyldeoxythymidine (DMTr-d [TCCCGCCTGCGACATGCATT] (SEQ ID NO: 6)-H) by 10+10 Fragment Condensation and Deprotection

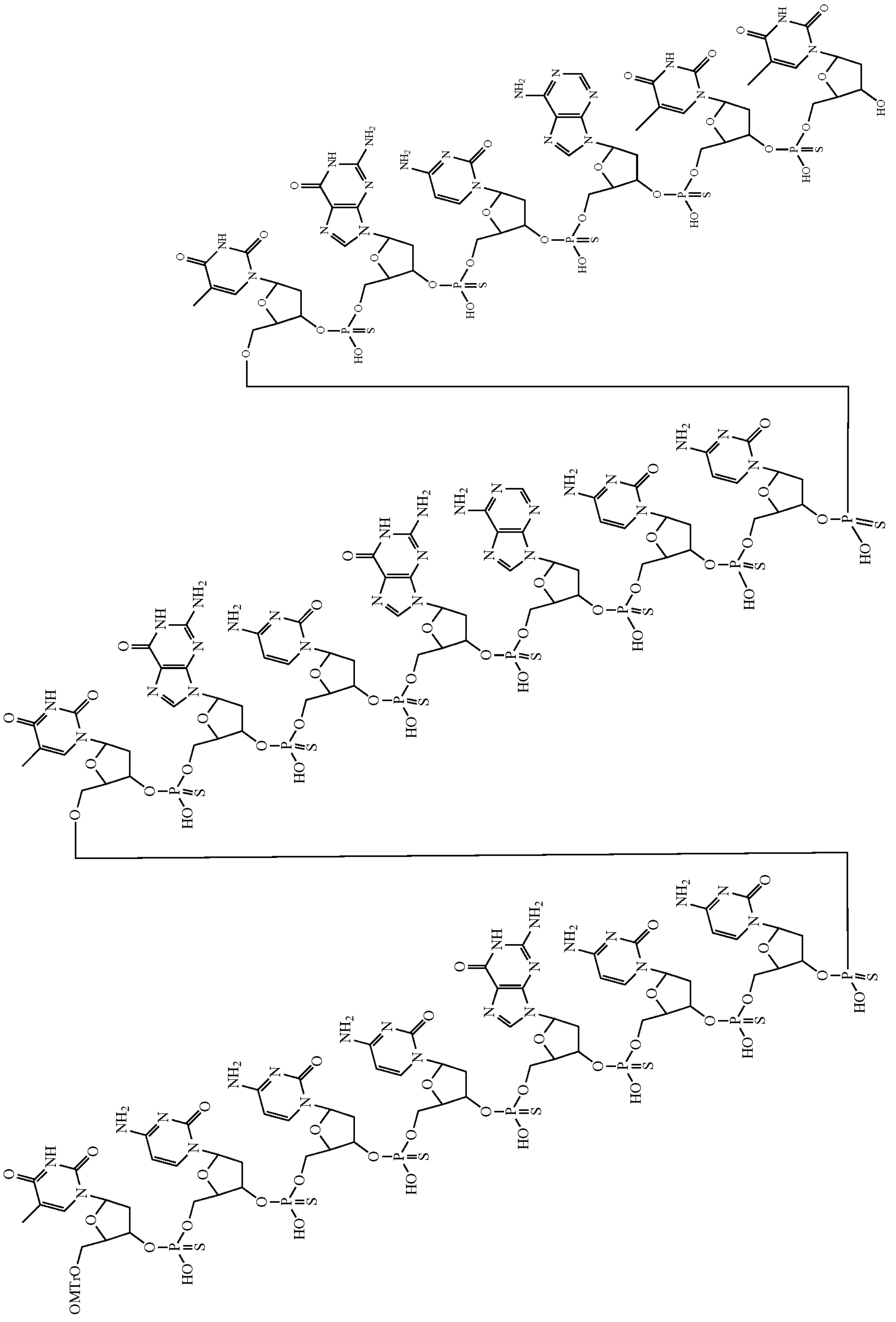

The solid (1.00 g, 0.100 mmol) obtained in Example 26 containing DMTr-d[TC$^{Bz}$C$^{Bz}$C$^{Bz}$G$^{iBu}$C$^{Bz}$C$^{Bz}$TG$^{iBu}$C$^{CO\text{-}TOP}$]-PA at a content of 56 wt % together with methyl 3,4,5-tris(octadecyloxy)benzoate and the solid (0.556 g, 0.083 mmol) obtained in Preparation Example 2 containing H-d[G$^{iBu}$A$^{dma}$C$^{HD}$A$^{dma}$TG$^{iBu}$C$^{HD}$A$^{dma}$TT]-suc-TOB at a content of 82 wt % together with methyl 3,4,5-tris(octadecyloxy)benzoate were stirred for 1 hr in dehydrated dichloromethane (7.5 mL) together with molecular sieve 3A powder (0.544 g) previously dehydrated with a strong heat to give a dehydration solution, To this suspension was added dehydrated acetonitrile (0.75 mL), the total amount was filtered through a 0.45 μm membrane filter and obtained in a 20 mL Schlenk tube. Thereto was added 5-(benzylthio)-1H-tetrazole (47.2 mg, 0.245 mmol) and the mixture was stirred under dry argon for 3 hr. To the reaction mixture were added pyridine (80 μL, 1.0 mmol) and ethanol (5.84 μL) to quench the system. Thereto was added 3-[(N,N-dimethylaminomethylidene)amino]-3H-1,2,4-dithiazole-5-thione (33.7 mg, 0.164 mmol) and the mixture was stirred for 30 min to sulfurate phosphite intermediate. Acetonitrile (42 mL) was added to precipitate the compound group having an anchor. The precipitate was obtained by filtration, washed with acetonitrile (42 mL) and dried in vacuo to give 1.34 g of a solid. 10.6 mg from the sample together with methanol (250 μL) and 28% aqueous ammonia (1.0 mL) were placed in a 2 mL glass vial containing stirrer chips, tightly sealed and stirred in an oil bath at 45° C. for 18 hr to perform deprotection. The aqueous solution was cooled to room temperature, and ammonia was removed in a centrifugation evaporator at 35° C. for 10 min. The mixture was measured up with 2 M triethylamine-acetate buffer to 5.0 mL, filtered through a 0.45 μm membrane filter, insoluble matter was removed and the remaining was analyzed by liquid chromatography. Separately, accurately-measured 10.6 mg of a solid containing H-d[G$^{iBu}$A$^{dma}$C$^{HD}$A$^{dma}$TG$^{iBu}$C$^{HD}$A$^{dma}$TT]-suc-TOB at a content of 82 wt % together with methyl 3,4,5-tris(octadecyloxy)benzoate was similarly deprotected and diluted. Using the obtained sample as the reference standard, unreacted H-d[G$^{iBu}$A$^{dma}$C$^{HD}$A$^{dma}$TG$^{iBu}$C$^{HD}$A$^{dma}$TT]-suc-TOB in the coupling mixture was quantified. As a result, H-d[G$^{iBu}$A$^{dma}$C$^{HD}$A$^{dma}$TG$^{iBu}$C$^{HD}$A$^{dma}$TT]-suc-TOB was contained in an amount corresponding to 137 mg of the mixture (82 w/w %) used actually with a crystallization adjuvant, and the conversion ratio of H-d[G$^{iBu}$A$^{dma}$C$^{HD}$A$^{dma}$TG$^{iBu}$C$^{HD}$A$^{dma}$TT]-suc-TOB by the condensation reaction was determined to be 76%.

The sample subjected to the aforementioned deprotection and dilution was analyzed by LC/MS and the title compound was identified.

LC/MS m/z: calcd 2209.57, found 2209.55 $[M\text{-}3H]^{3-}$.

Example 28: Phosphitylation of 5'-terminal

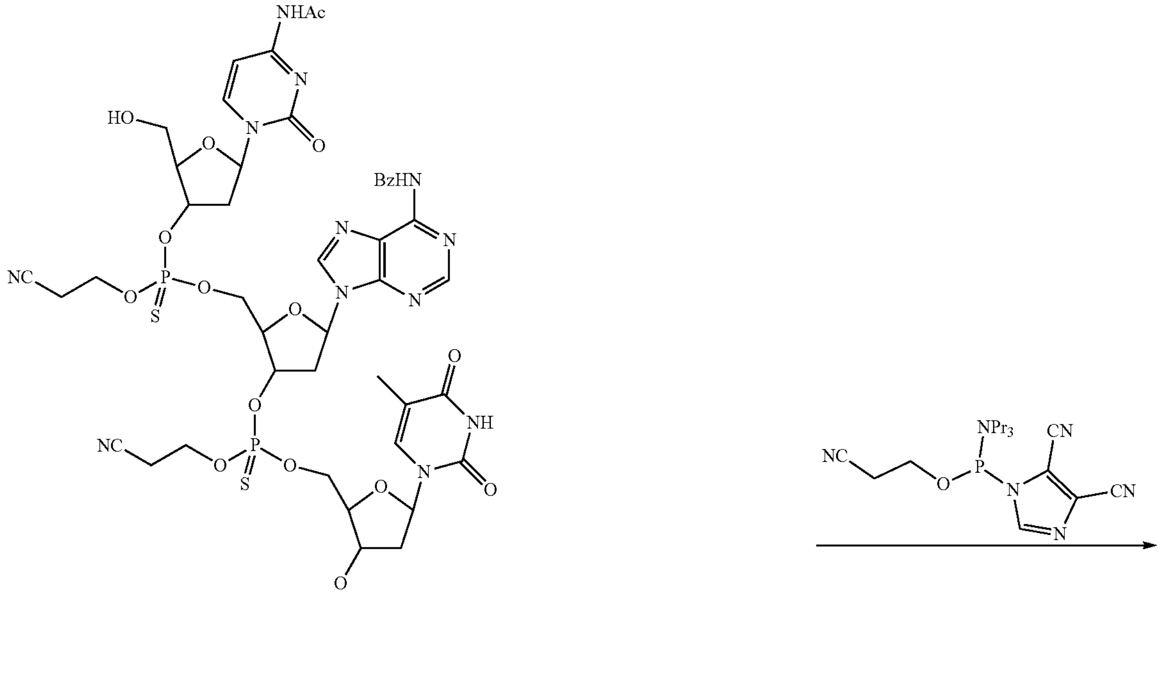

-continued
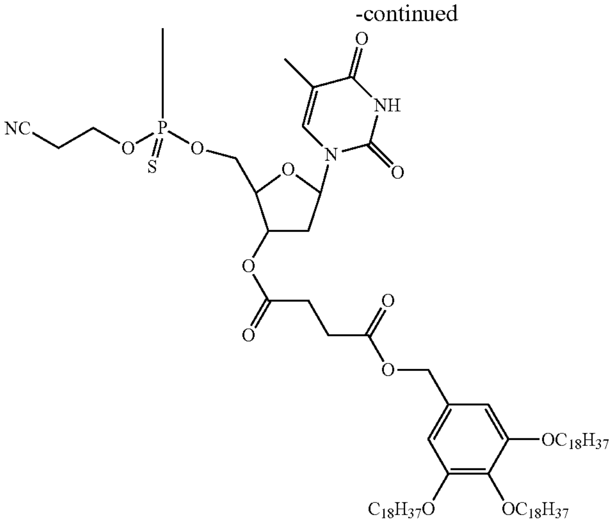
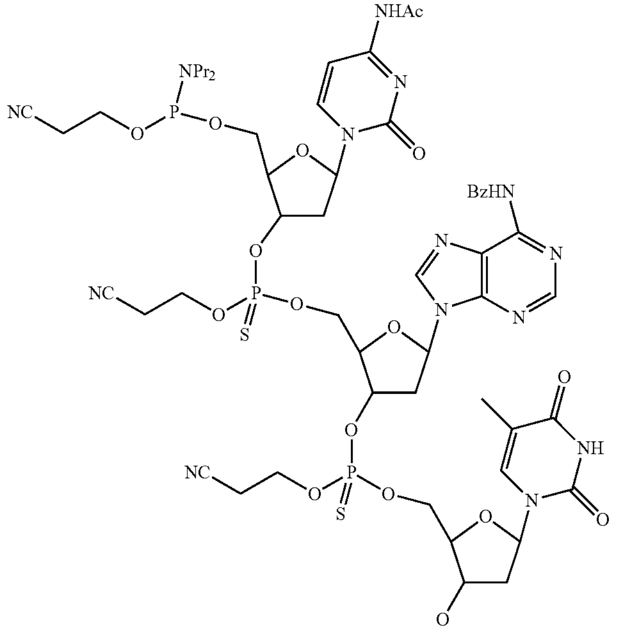
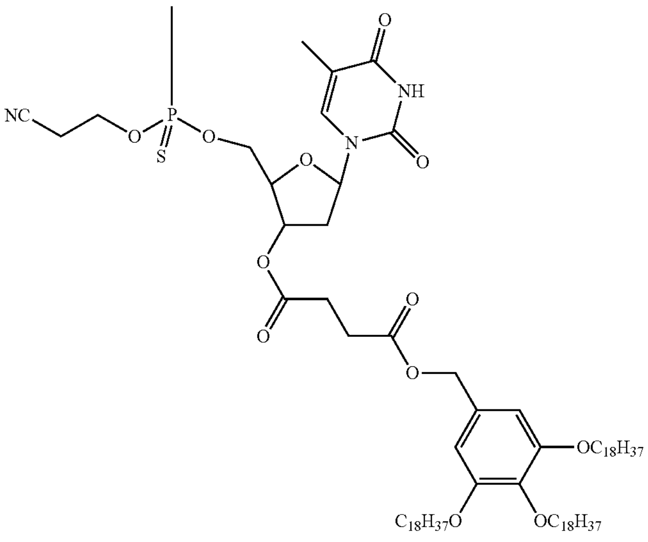

In the same manner as in Example 6, in dehydrated toluene, to a phosphitylating agent solution (1.5 mL, 0.60 mmol as filtrate) prepared from 2-cyanoethyl-N,N,N',N'-tetraisopropylphosphordiamidite and 4,5-dicyanoimidazole was added N-methylmorpholine (0.66 mL, 6.0 mmol). H-d[$C^{Ac}A^{Bz}$TT]-suc-TOB (0,496 g, 0.20 mmol) was added thereto at 10° C. to give a suspension. Dichloromethane (10.0 mL) was added at the same temperature to give a uniform solution, and the solution was stirred for 2 hr. Complete conversion of the starting material was confirmed by LC/MS, and the reaction was discontinued with 2,4,6-trimethylpyridine (0.79 mL, 6.0 mmol). The reaction mixture was cooled to 0° C., acetonitrile was added, and the resultant product was precipitated. The precipitate was filtered using a hirsch funnel, washed and dried in vacuo to give ($^{i}Pr_2N$)($NCCH_2CH_2O$)P-d[$C^{Ac}A^{Bz}$TT]-suc-TOB (0.4227 g, 0.16 mmol, 79% yield) as a white solid. H-d[$C^{Ac}A^{Bz}$TT]-suc-TOB was prepared by condensing d[$A^{Bz}$TT]-suc-TOB obtained in the same manner as in Preparation Example 1-(3) and nucleosidephosphoramidite and further de-DMTr-lation. The nucleosidephosphoramidite used was as follows.

d$C^{Ac}$: 5'-(4,4'-dimethoxytrityl)-$N^4$-acetyl-2'-deoxycytidine-3'-[(2-cyanoethyl)-N,N-diisopropyl]phosphoramidite The resultant product was analyzed by $^{31}P\{^{1}H\}$NMR. H-phosphonate diester was detected at 9% of the object product, but a decyanoethylated form on internucleotide phosphoric acid was not detected, and phosphite in which two oligonucleic acid 5'-terminals were linked via phosphorus introduced by this reaction was below detection limit.

Using phosphoramidite with phosphitylated 5'-terminal, oligonucleotide having a functional group linked to the 5'-terminal side directly or via a linker can be obtained.

INDUSTRIAL APPLICABILITY

According to the method of the present invention, a phosphitylating agent can be prepared from diamidites stable during storage and falling off of a protecting group on phosphoric acid during phosphitylation reaction can be suppressed. Therefore, 3'-terminal phosphoramidited oligonucleotide can be produced more stably and efficiently. According to the method of the present invention, moreover, a 3'-terminal silyl-protecting group can be eliminated without falling off of a cyanoethyl-protecting group on phosphoric acid between nucleotides. Using these methods, therefore, more efficient production of oligonucleotide and fragment condensation using same become possible.

This application is based on a patent application No. 2015-250665 filed in Japan (filing date: Dec. 22, 2015), the contents of which are incorporated in full herein.

The invention claimed is:

1. A method for producing n-mer oligonucleotide, wherein n is an integer between two and 50, wherein a 5'-position hydroxyl group or 5'-position phosphoric acid group of the n-mer oligonucleotide is protected and a 3'-position hydroxyl group of the n-mer oligonucleotide is not protected, said method comprising:

mixing an n-mer oligonucleotide of formula (I) with a fluoride ion source in a solvent in the presence of not less than 2 kinds of organic bases, selected from a strong organic base and a weak organic base, wherein said strong organic base has a pKa≥8 and said weak organic base has a pKa of 4≤pKa<8, wherein the fluoride ion source is a salt of at least one of the not less than 2 kinds of organic bases and hydrogen fluoride:

(I)

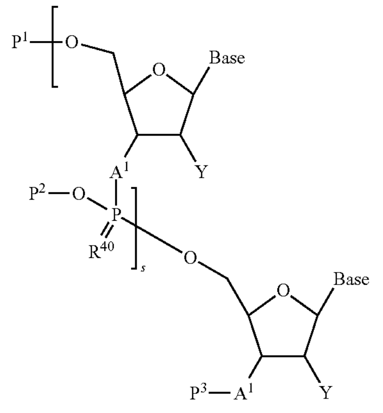

wherein:

each $A^1$ in the number of s or outside s is independently an oxygen atom, each Base in the number of s or outside s is a nucleic acid base which is not protected or protected by an amino-protecting group selected from the group consisting of pivaloyl group, pivaloyloxymethyl group, trifluoroacetyl group, phenoxyacetyl group, 4-isopropylphenoxyacetyl group, 4-tert-butylphenoxyacetyl group, acetyl group, benzoyl group, isobutyryl group, dimethylformamidinyl group and 9-fluorenylmethyloxycarbonyl group or by, a protecting group of the following (1), (2), or (3), provided that the nucleic acid base is protected by the protecting group when the nucleic acid base is adenine (A), guanine (G), or cytosine (C):

(1) a protecting group having $C_{5-30}$ straight chain or branched chain alkyl group and/or $C_{5-30}$ straight chain or branched chain alkenyl;

(2) a protecting group having the formula: $-L-Y^L—Z$, wherein:

L is a group (linker) having the formula (a1):

(a1)

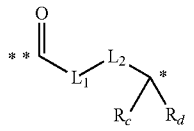

wherein ** is the bonding position to nucleic acid base,

* is the bonding position to $Y^L$, $L_1$ is a saturated or substituted divalent $C_{1-22}$ hydrocarbon group, an oxygen atom or —NR— (wherein R is an alkyl group or an aralkyl group), $L_2$ is a single bond or a group having the formula: $*C(R^{3a})(R^{3b})—O—R^1**$, formula: $*C(=O)N(R^2)—R^1—N(R^{3a})**$ or formula: $*C(=O)N(R^2)—R^1—C(R^{3a})(R^{3b})**$ wherein * of $L_2$ is the bonding position to $L_1$, ** is the bonding position to to $CR_dR_d$ of formula (a1) $R^1$ is a saturated or substituted $C_{1-22}$ alkylene group, $R^2$ and $R^{3a}$ are each independently a hydrogen atom or a saturated or substituted $C_{1-22}$ alkyl group, or $R^2$ and $R^{3a}$ are joined to form a saturated or substituted $C_{1-22}$ alkylene bond, provided that $R^{3a}$ in the formula: *C(=O)N($R^2$)—$R^1$—N($R^{3a}$)** is not a hydrogen atom, $R^{3b}$ is a hydrogen atom or a saturated or substituted $C_{1-22}$ alkyl group, $R_c$ and $R_d$ are each independently a hydrogen atom, an a saturated or substituted $C_{1-22}$ alkyl group or $R_c$ and $R_d$ are optionally joined to form a single carbonyl group, $Y^L$ is a single bond, an oxygen atom, or —NR— (wherein R is an alkyl group or an aralkyl group), or a sulfur atom; and Z is (i) a group having the formula (a2):

(a2)

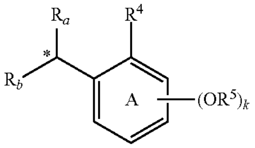

wherein * of formula (a2) is the bonding position to $Y^L$;

$R^4$ is a hydrogen atom, or when $R_b$ is a group having the following formula (a3), Z is a group having the following formula:

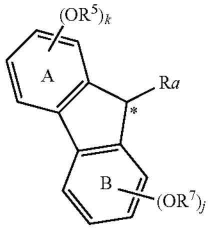

or

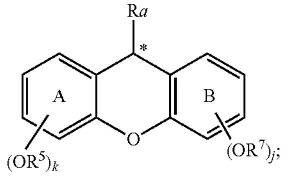

each $R^5$ in the number of k is independently a $C_{10-40}$ alkyl group;

k is an integer of 1 to 4;

ring A optionally has, in addition to $OR^5$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;

$R_a$ is a hydrogen atom or a phenyl group optionally substituted by a halogen atom; and $R_b$ is a hydrogen atom, or a group having the formula (a3):

(a3)

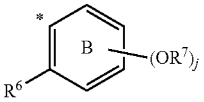

wherein * of formula (a3) is the bonding position to C—$R_a$;

j is an integer of 0 to 4;

each $R^7$ in the number of j is independently a $C_{10-40}$ alkyl group;

$R^6$ is a hydrogen atom, or is optionally a single bond or —O— in combination with $R^4$ to form a group having the following formula together with ring A;

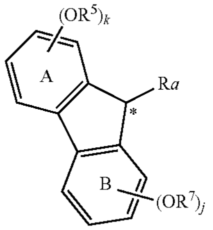

or

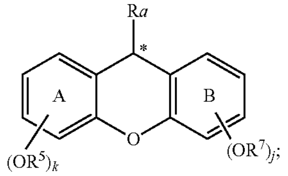

and ring B optionally has, in addition to $OR^7$ in the number of j, a substituent selected from the group consisting of a halogen atom, a $C_{1-6}$ alkyl group optionally substituted by a halogen atom, and a $C_{1-6}$ alkoxy group optionally substituted by a halogen atom;

or $R_a$ and $R_b$ are joined to form a single carbonyl group;

(ii) a group having the formula (a2'):

(a2')

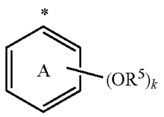

wherein * of formula (a2') is the bonding position to $Y^L$; and other symbols are each as defined for the formula (a2), or a group having the formula (a2"):

(a2")

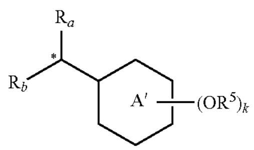

wherein * of formula (a2") is the bonding position to $Y^L$;

ring A' optionally has, in addition to $OR^5$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;

each symbol is as defined for the formula (a2), (3) a protecting group having the formula: (—Z')

[[Z']] (Z')

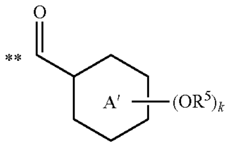

wherein ** of formula (Z') is the bonding position to nucleic acid base; and each symbol is as defined for the formula (a2"), $P^1$ is a hydroxyl-protecting group, or a phosphoric acid group as —O—$P^1$ in which one of the hydroxyl groups is replaced by any one of the following formulas (in the following formulas, * shows the bonding position to phosphorus atom and Ac is an acetyl group);

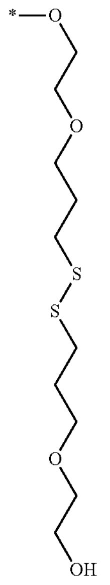

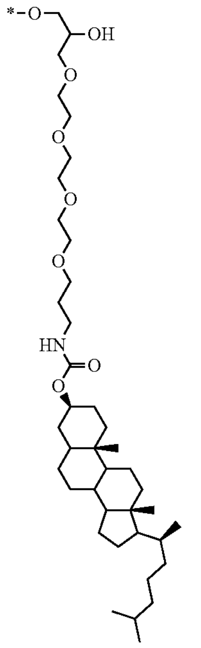

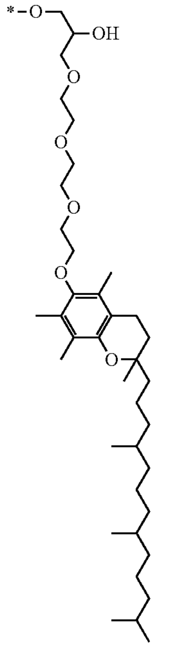

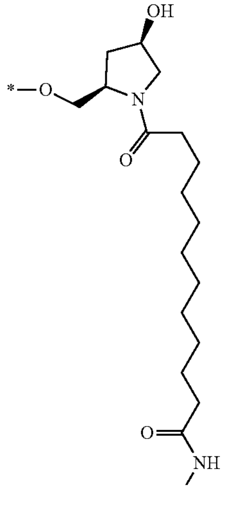

-continued

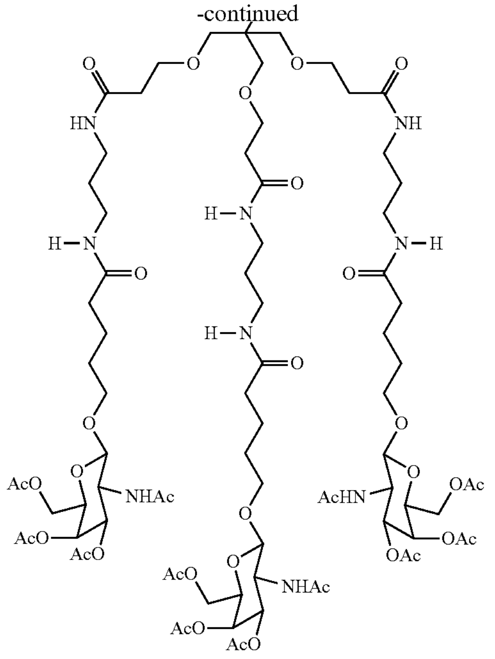

each $P^2$ in the number of s is independently a phosphoric acid-protecting group, each $R^{40}$ in the number of s is independently an oxygen atom or a sulfur atom, each Y in the number of s or outside s is independently a hydrogen atom, a protected hydroxyl group, a halogen atom, or an organic group that crosslinks to the 4-position carbon atom of the ribose, wherein the organic group that crosslinks to the 4-position carbon atom is —O—$CH_2$—, —O—$CH_2$—$CH_2$—, —O—$NR^{37}$—$CH_2$— (wherein $R^{37}$ is a $C_{1-6}$ alkyl group) or —O—$CH_2$—O—$CH_2$—, $P^3$ is a silyl-protecting group, selected from the group consisting of tert-butyldimethylsilyl (TBDMS), diisopropylphenylsilyl (DIPPS), tert-butoxy diphenylsilyl (TBODPS) and isopropoxydiisopropylsilyl (IPODIPS), and s is an integer n−1, wherein in the n-mer oligonucleotide of formula (I), a 5'-position hydroxyl group or 5'-position phosphoric acid group is protected and a 3'-position hydroxyl group is protected by the silyl-protecting group $P^3$ before mixing with the fluoride ion source.

2. The method according to claim 1, wherein said organic bases are present in an amount of not less than 1 molar equivalent relative to the fluoride ion source.

3. The method according to claim 1, wherein said strong organic base is present in an amount of not more than ⅓ molar equivalents.

4. The method according to claim 1, wherein said strong organic base is one or two kinds selected from the group consisting of methylamine, dimethylamine, trimethylamine, ethylamine, diethylamine, triethylamine, propylamine, isopropylamine, diisopropylamine, diisopropylethylamine, butylamine, isobutylamine, tert-butylamine, 1,4-diazabicyclo[2.2.2]octane, and morpholine.

5. The method according to claim 1, wherein said weak organic base is one or two kinds selected from the group consisting of pyridine, 2,6-dimethylpyridine, 2,4,6-trimethylpyridine, piperazine, piperidine, imidazole, N-methylimidazole, N-methylmorpholine, N-ethylmorpholine, aniline, toluidine, dimethylaniline, ethylaniline, diethylaniline, ethylmethylaniline, and anisidine.

6. The method according to claim 1, wherein said organic base is a mixture of triethylamine and pyridine.

7. Method according to claim 1, wherein said fluoride ion source is one or more members selected from the group consisting of triethylamine pentahydrofluoride, triethylamine trihydrofluoride, and pyridine hydrofluoride.

8. The method according to claim 1, wherein Base at the 3'-terminal nucleoside of the n-mer oligonucleotide of formula (I) is protected by an amino-protecting group selected from the group consisting of pivaloyl group, pivaloyloxymethyl group, trifluoroacetyl group, phenoxyacetyl group, 4-isopropylphenoxyacetyl group, 4-tert-butylphenoxyacetyl group, acetyl group, benzoyl group, isobutyryl group, dimethylformamidinyl group and 9-fluorenylmethyloxycarbonyl group, or is protected by (2) the protecting group having the formula: -L-$Y^L$—Z, or is protected by (3) the protecting group having the formula: —Z'.

* * * * *

SEQUENCE LISTING

```
<160> NUMBER OF SEQ ID NOS: 6

<210> SEQ ID NO 1
<211> LENGTH: 10
<212> TYPE: DNA
<213> ORGANISM: Artificial Sequence
<220> FEATURE:
<223> OTHER INFORMATION: A sequence for test synthesis

<400> SEQUENCE: 1

tcccgcctgt                                                              10


<210> SEQ ID NO 2
<211> LENGTH: 10
<212> TYPE: DNA
<213> ORGANISM: Artificial Sequence
<220> FEATURE:
<223> OTHER INFORMATION: A sequence for test synthesis

<400> SEQUENCE: 2

gacatgcatt                                                              10


<210> SEQ ID NO 3
<211> LENGTH: 20
<212> TYPE: DNA
<213> ORGANISM: Artificial Sequence
<220> FEATURE:
<223> OTHER INFORMATION: A sequence for test synthesis

<400> SEQUENCE: 3

tcccgcctgt gacatgcatt                                                   20


<210> SEQ ID NO 4
<211> LENGTH: 10
<212> TYPE: DNA
<213> ORGANISM: Artificial Sequence
<220> FEATURE:
<223> OTHER INFORMATION: A sequence for test synthesis
```

-continued

```
<400> SEQUENCE: 4

tcccgcctgc                                                           10


<210> SEQ ID NO 5
<211> LENGTH: 10
<212> TYPE: DNA
<213> ORGANISM: Artificial Sequence
<220> FEATURE:
<223> OTHER INFORMATION: A sequence for test synthesis

<400> SEQUENCE: 5

gacatgcatt                                                           10


<210> SEQ ID NO 6
<211> LENGTH: 20
<212> TYPE: DNA
<213> ORGANISM: Artificial Sequence
<220> FEATURE:
<223> OTHER INFORMATION: A sequence for test synthesis

<400> SEQUENCE: 6

tcccgcctgc gacatgcatt                                                20
```